United States Patent
Shaw et al.

(10) Patent No.: US 11,479,543 B2
(45) Date of Patent: Oct. 25, 2022

(54) HETEROCYCLIC RIP1 KINASE INHIBITORS

(71) Applicant: Rigel Pharmaceuticals, Inc., South San Francisco, CA (US)

(72) Inventors: Simon Shaw, Oakland, CA (US); Somasekhar Bhamidipati, Foster City, CA (US); Vanessa Taylor, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 17/013,034

(22) Filed: Sep. 4, 2020

(65) Prior Publication Data

US 2021/0070744 A1    Mar. 11, 2021

Related U.S. Application Data

(60) Provisional application No. 62/897,223, filed on Sep. 6, 2019, provisional application No. 62/932,404, filed on Nov. 7, 2019, provisional application No. 63/001,016, filed on Mar. 27, 2020, provisional application No. 63/004,290, filed on Apr. 2, 2020, provisional application No. 63/004,301, filed on Apr. 2, 2020, provisional application No. 63/004,319, filed on Apr. 2, 2020.

(51) Int. Cl.

| | |
|---|---|
| *C07D 401/14* | (2006.01) |
| *C07D 401/12* | (2006.01) |
| *C07D 403/12* | (2006.01) |
| *C07D 403/14* | (2006.01) |
| *C07D 405/14* | (2006.01) |
| *C07D 471/08* | (2006.01) |
| *C07D 487/04* | (2006.01) |
| *C07D 491/107* | (2006.01) |
| *C07D 413/12* | (2006.01) |
| *C07D 413/14* | (2006.01) |
| *C07D 267/02* | (2006.01) |
| *C07D 493/04* | (2006.01) |
| *A61K 31/553* | (2006.01) |

(52) U.S. Cl.
CPC .......... *C07D 401/14* (2013.01); *A61K 31/553* (2013.01); *C07D 267/02* (2013.01); *C07D 401/12* (2013.01); *C07D 403/12* (2013.01); *C07D 403/14* (2013.01); *C07D 405/14* (2013.01); *C07D 413/12* (2013.01); *C07D 413/14* (2013.01); *C07D 471/08* (2013.01); *C07D 487/04* (2013.01); *C07D 491/107* (2013.01); *C07D 493/04* (2013.01)

(58) Field of Classification Search
CPC .................................................. C07D 413/14
See application file for complete search history.

(56) References Cited

U.S. PATENT DOCUMENTS

| | | | |
|---|---|---|---|
| 8,658,689 | B2 | 2/2014 | Cuny et al. |
| 9,556,152 | B2 | 1/2017 | Harris et al. |
| 9,624,202 | B2 | 4/2017 | Jeong |
| 9,815,850 | B2 | 11/2017 | Estrada et al. |
| 9,896,458 | B2 | 2/2018 | Estrada et al. |
| 2015/0353533 | A1 | 12/2015 | Bandyopadhyay et al. |
| 2017/0008877 | A1 | 1/2017 | Patel et al. |
| 2017/0226127 | A1 | 8/2017 | Estrada et al. |
| 2019/0337907 | A1 | 11/2019 | Masuda et al. |
| 2019/0337934 | A1 | 11/2019 | Taylor et al. |
| 2021/0070743 | A1 | 3/2021 | Shaw et al. |
| 2021/0070744 | A1 | 3/2021 | Chen et al. |
| 2021/0292340 | A1 | 9/2021 | Ma et al. |
| 2021/0317135 | A1 | 10/2021 | Darwish et al. |
| 2021/0371430 | A1 | 12/2021 | Zhou et al. |

FOREIGN PATENT DOCUMENTS

| | | |
|---|---|---|
| WO | WO 2014/125444 | 8/2014 |
| WO | WO 2014/145022 | 9/2014 |
| WO | WO 2016/027253 | 2/2016 |
| WO | WO 2016/128936 | 8/2016 |
| WO | WO 2017/064217 | 4/2017 |
| WO | WO 2017/069279 | 4/2017 |
| WO | WO 2017/109724 | 6/2017 |
| WO | WO 2017/13 6727 | 8/2017 |
| WO | WO 2018/073193 | 4/2018 |
| WO | WO 2018/109097 | 6/2018 |
| WO | WO 2018/154520 | 8/2018 |
| WO | 2020/001420 | 1/2020 |
| WO | 2020/088194 | 5/2020 |

OTHER PUBLICATIONS

Harris et al., "DNA-encoded library screening identifies benzo[b][1,4]oxazepin-4-ones as highly potent and mono-selective receptor interfacing protein 1 (RIP1) kinase inhibitors," *Journal of Medical Chemistry* 59(5):2163-2178, Mar. 10, 2016.

Harris et al., "Discovery of a First-in-Class Receptor Interacting Protein 1 (RIP1) Kinase Specific Clinical Candidate (GSK2982772) for the Treatment of Inflammatory Diseases," *Journal of Medicinal Chemistry* 60:1247-1261, 2017.

Harris et al., "Identification of a RIP1 Kinase Inhibitor Clinical Candidate (GSK3145095) for the Treatment of Pancreatic Cancer," *ACS Medicinal Chemistry Letters* 10:857-862, 2019.

Ishii et al., "CETSA quantitatively verifies in vivo target engagement of novel RIPK1 inhibitors in various biospecimens," *Scientific Reports* 7(1):13000, pp. 1-14, 2017.

Najjar et al., "Structure guided design of potent and selective ponatinib-based hybrid inhibitors for RIPK1," *Cell Reports* 12(11):1850-1860, Mar. 24, 2015.

(Continued)

*Primary Examiner* — Erich A Leeser

(74) *Attorney, Agent, or Firm* — Gabriel Magallanes

(57) ABSTRACT

Disclosed herein are kinase inhibitory compounds, such as a receptor-interacting protein-1 (RIP1) kinase inhibitor compounds, as well as pharmaceutical compositions and combinations comprising such inhibitory compounds. The disclosed compounds, pharmaceutical compositions, and/or combinations may be used to treat or prevent a kinase-associated disease or condition, particularly a RIP1-associated disease or condition.

3 Claims, No Drawings

(56) References Cited

OTHER PUBLICATIONS

Harris, et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase," Journal of Medicinal Chemistry, vol. 62, No. 10, pp. 5096-5110 (2019).

Yoshikawa, et al., "Discovery of 7-Oxo-2,4,5,7-tetrahydro-6 H-pyrazolo [3,4-C] pyridine Derivatives as Potent, Orally Available, and Brain-Penetrating Receptor Interacting Protein 1 (RIP1) Kinase Inhibitors Analysis of Structure-Kinetic Relationships," Journal of Medicinal Chemistry, vol. 61, No. 6, pp. 2384-2409 (2018).

HETEROCYCLIC RIP1 KINASE INHIBITORS

CROSS REFERENCE TO RELATED APPLICATIONS

This application claims the benefit of the earlier filing dates of U.S. Provisional Application No. 62/897,223, filed on Sep. 6, 2019, U.S. Provisional Application No. 62/932,404, filed on Nov. 7, 2019, U.S. Provisional Application No. 63/001,016, filed on Mar. 27, 2020, U.S. Provisional Application No. 63/004,290, filed on Apr. 2, 2020, U.S. Provisional Application No. 63/004,301, filed on Apr. 2, 2020, and U.S. Provisional Application No. 63/004,319, filed on Apr. 2, 2020.

FIELD

The present disclosure concerns compounds and methods of making and using the compounds, such as for inhibiting receptor-interacting protein-1 ("RIP1") kinase, and for treating diseases and/or conditions related to RIP1.

BACKGROUND

Receptor-interacting protein-1 kinase (referred to herein as "RIP1") belongs to the tyrosine kinase-like family and is a serine/threonine protein kinase involved in innate immune signaling. RIP1 plays a central role in regulating cell signaling and its role in programmed cell death has been linked to various inflammatory diseases, such as inflammatory bowel disease, psoriasis, and other diseases and/or conditions associated with inflammation and/or necroptotic cell death.

SUMMARY

Disclosed compounds according to the present disclosure may have a Formula I

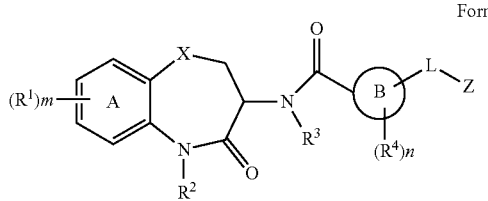

Formula I or a pharmaceutically acceptable salt, N-oxide, solvate, tautomer, or stereoisomer thereof. With respect to Formula I, ring B is heteroaryl, and may be a monocyclic heteroaryl. In some embodiments, ring B is a 5-membered or 6-membered heteroaryl, and may be pyrazolyl or pyridinyl.

Each $R^1$ independently is halogen or -linker-$R^6$ group, wherein the linker is a bond or $R^a$, provided that $R^a$ is not H or D, and $R^6$ is heterocyclyl, $R^b$, —C($R^f$)$_3$, or —C($R^f$)=C($R^f$)$_2$; $R^2$ is $R^a$; $R^3$ is $R^a$ and may be H; if present, each $R^4$ independently is $R^e$; and L is a heteroatom or $R^a$, provided that $R^a$ is not H or D.

$R^a$ is independently for each occurrence H or D, except for embodiments where L is $R^a$, $C_{1-10}$aliphatic, $C_{1-10}$haloaliphatic, $C_{5-10}$aromatic, $C_{3-6}$heterocyclic, or $C_{3-10}$spiroheterocyclic; $R^b$ is independently for each occurrence —OH, —SH, —OR$^c$, —SR$^c$, —NR$^d$R$^d$, —Si(R$^a$)$_3$, —C(O)OH, —C(O)OR$^c$, —C(O)NR$^d$R$^d$, —OC(O)NR$^d$R$^d$, —OC(O)$C_{1-10}$alkyl substituted with one or two NR$^d$R$^d$, carboxyl, or a combination thereof, and optionally further substituted with an aromatic moiety, —SH, —O-acyl, or —C(O)NH$_2$; $R^c$ is independently for each occurrence $C_{1-10}$alkyl, which can be substituted with 1, 2 or 3 $R^e$, $C_{2-10}$alkenyl, which can be substituted with 1, 2 or 3 $R^e$, $C_{2-10}$alkynyl, which can be substituted with 1, 2 or 3 $R^e$, $C_{3-6}$cycloalkyl, which can be substituted with 1, 2 or 3 $R^e$, or $C_{5-10}$aromatic, which can be substituted with 1, 2 or 3 $R^e$; $R^d$ is independently for each occurrence H; $C_{1-6}$alkyl, which can be substituted with 1, 2 or 3 $R^e$ or a $C_{3-9}$heterocyclyl; $C_{3-6}$cycloalkyl, which can be substituted with 1, 2 or 3 $R^e$; $C_{3-6}$heterocyclic, which can be substituted with 1, 2 or 3 $R^e$; $C_{5-10}$aryl, which can be substituted with 1, 2 or 3 $R^b$; $C_{5-10}$heteroaryl, which can be substituted with 1, 2 or 3 $R^e$; or two $R^d$ groups together with the nitrogen bound thereto provide a $C_{3-9}$heterocyclic, which can be substituted with one or more $R^e$), or a $C_{5-10}$heteroaryl, which can be substituted with one or more $R^e$; $R^e$ is independently for each occurrence halogen, $C_{1-6}$alkyl, $C_{2-10}$alkenyl, $C_{2-10}$alkynyl, $C_{1-6}$haloalkyl, $C_{3-6}$cycloalkyl, $C_{5-10}$heteroaryl, or —OR$^a$; and $R^f$ is independently for each occurrence -alkyl-phosphate, $R^a$, $R^b$, or $R^e$, or two $R^f$ groups together with the carbon atom bound thereto provide a $C_{2-6}$alkenyl group, a $C_{3-6}$cycloalkyl group, which can be substituted with one or more $R^e$, or a $C_{3-10}$heterocyclic, which can be substituted with one or more $R^e$ or acyl.

Also with respect to Formula I, X is CH$_2$ or O; Z is heteroaryl; m is 1, 2, 3, or 4; and n is 0, 1 or 2. In some embodiments, m is 1, and/or n is 0 or n is 1.

In some embodiments, $R^2$ is $C_{1-6}$alkyl, and may be CH$_3$ or CD$_3$.

In certain embodiments, n is 0, but in other embodiments, n is 1. In such embodiments, $R^4$ may be $C_{1-6}$alkyl, such as methyl.

In certain embodiments, L is a heteroatom, such as O, but in other examples, L is $C_{1-6}$alkyl, such as CH$_2$.

In some embodiments, Z may be a 6-membered heteroaryl, and may be pyridinyl, pyrimidinyl, or pyridazinyl. In any embodiments, Z may be unsubstituted or Z may be substituted, such as with halogen, $C_{1-6}$alkyl, $C_{1-6}$haloalkyl, or OH. In some embodiments, Z is

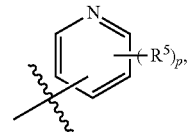

p is 0, 1, 2, 3, or 4, and if present, each $R^5$ independently is $R_e$. Each $R^5$ independently may be OH, halogen, $C_{1-6}$alkyl, or $C_{1-6}$haloalkyl, such as OH, CF$_3$, methyl or fluoro. And/or in some embodiments, p is 1, but in other embodiments, p is 0.

And in any embodiments, the -L-Z moiety may be (6-fluoropyridin-2-yl)methyl, (6-methylpyridin-2-yl)methyl, (2-methylpyridin-5-yl)oxy, (2-fluoropyridin-5-yl)oxy, pyridin-2-ylmethyl, (6-trifluoromethylpyridin-2-yl)methyl, (6-hydroxypyridin-2-yl)methyl, pyridin-3-ylmethyl, pyridazin-3-ylmethyl, (2-methylpyridin-5-yl)methyl, (2-fluoropyridin-5-yl)methyl, (2-fluoropyridin-3-yl)methyl, (2,6-difluoropyridin-3-yl)methyl, pyrimidin-2-ylmethyl, or pyridin-4-ylmethyl.

In some embodiments, ring B is pyrazolyl and in some embodiments, the —N($R^3$)C(O)-moiety is attached to ring B at a ring nitrogen atom on ring B.

At least one $R^1$ may be halogen, such as Br, and/or at least one $R^1$ may be -linker-$R^6$. In some embodiments, at least one $R^1$ is 8- to 12-membered spiroheterocyclyl, $C_{1-10}$alkyl or a $C_{2-10}$alkyne. And in certain embodiments, at least one $R^1$ is

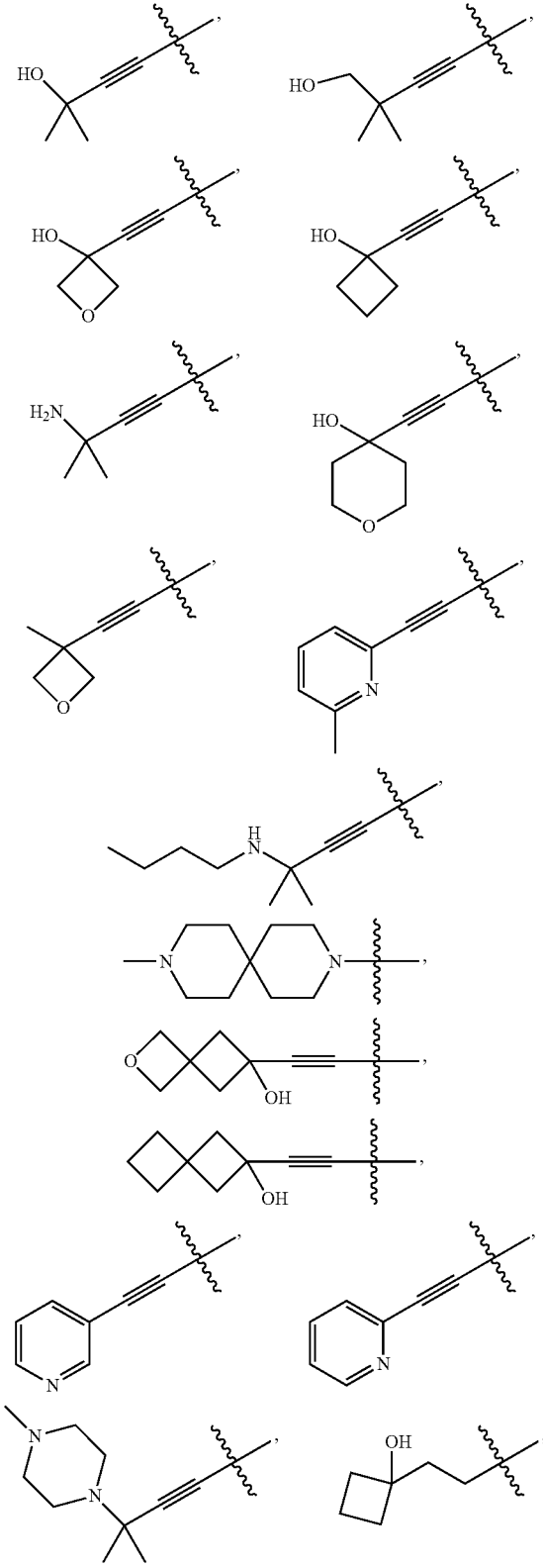

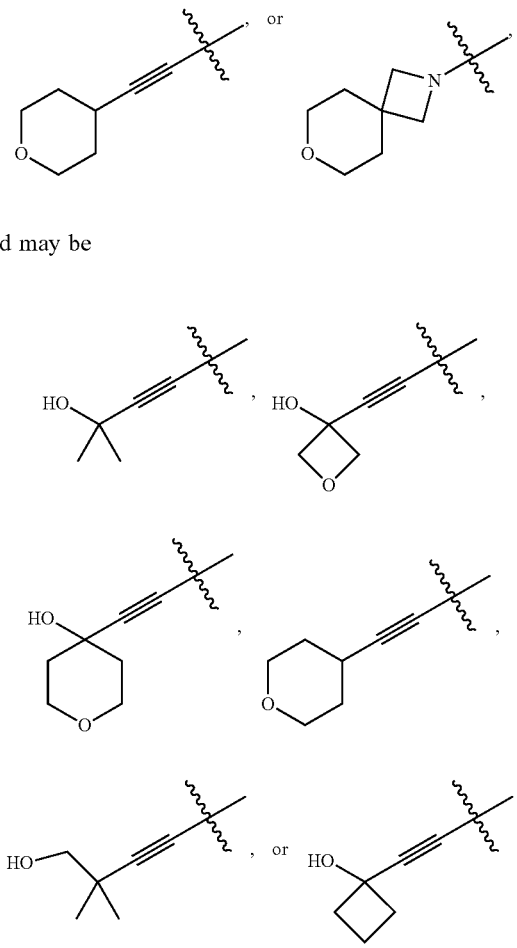

and may be

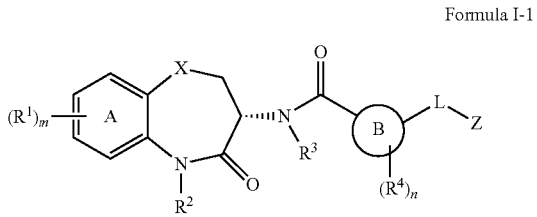

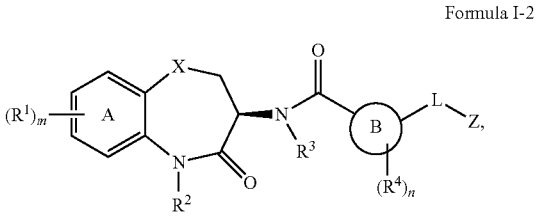

A person of ordinary skill will appreciate that compounds of all stereoisomers are included in Formula 1, including but not limited to, compounds having a formula Formula I-1

Formula I-2 or a pharmaceutically acceptable salt, N-oxide, solvate, tautomer, or stereoisomer thereof. In particular embodiments of the compounds according to Formula I, the compound may have a formula as indicated below, including any and all stereoisomers thereof:

Formula I-3
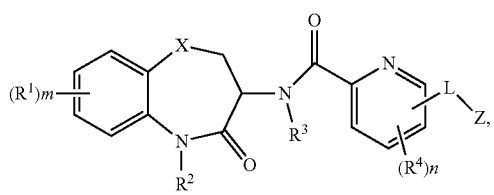

Formula I-4
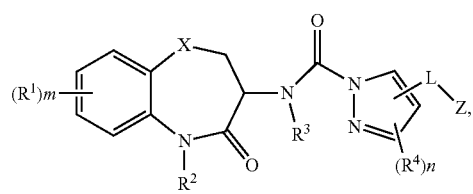

Formula I-5
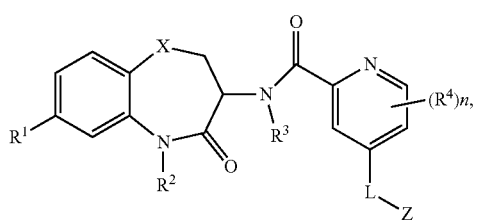

Formula I-6
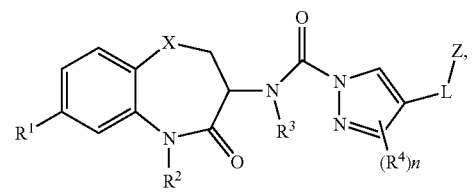

Formula I-7
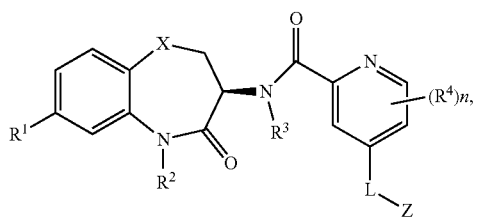

Formula I-8
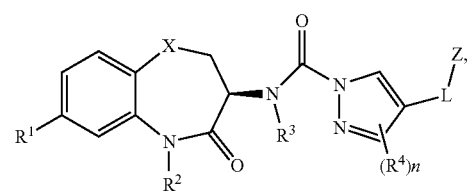

Formula I-9
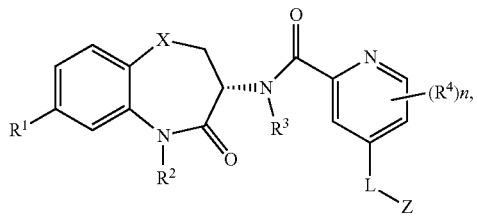

Formula I-10
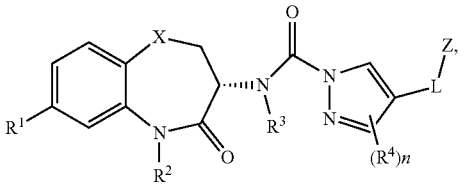

Formula I-11
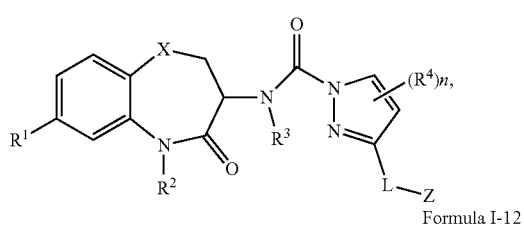

Formula I-12
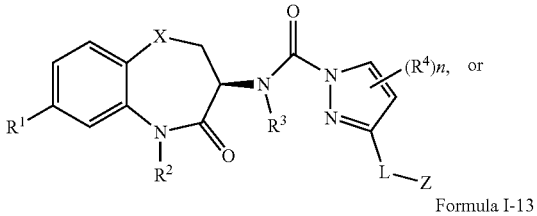

Formula I-13 or a pharmaceutically acceptable salt, N-oxide, solvate, tautomer, or stereoisomer thereof.

Also disclosed herein are embodiments of a composition comprising one or more of the disclosed compounds. The composition may further comprise an excipient, a therapeutic agent, or combinations thereof.

Embodiments of a method of using the disclosed compounds, or composition thereof, also are disclosed herein. In some embodiments, the method may comprise administering one or more of the disclosed compounds, or a composition thereof, to a subject. The method may be a method for treating a disease in a subject and/or may comprise administering to the subject (i) a therapeutically effective amount of a disclosed compound or a pharmaceutically acceptable salt, a stereoisomer, an N-oxide, a tautomer, a hydrate, a solvate, an isotope, or a prodrug thereof, or (ii) a therapeutically effective amount of a pharmaceutical composition of the compound. In some embodiments, the subject may have, or may be suspected of having or developing, the disease, such as a disease involving a receptor-interacting protein-1 (RIP1) kinase. Examples of diseases that can be treated according to this method embodiment include diseases or disorders associated with inflammation, necroptosis, or both. In certain embodiments, diseases to be treated with the present compounds are inflammatory or immune-regulatory disorders, including autoimmune and proliferative disorders. Exemplary diseases are disclosed herein.

Also disclosed herein are embodiments of a method comprising contacting a receptor-interacting protein-1

(RIP1) kinase with one or more disclosed compound a pharmaceutical composition thereof. The method may be an in vitro method or an in vivo method, such as when the RIP1 kinase is in a subject.

The foregoing and other objects and features of the present disclosure will become more apparent from the following detailed description.

DETAILED DESCRIPTION

I. Overview of Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

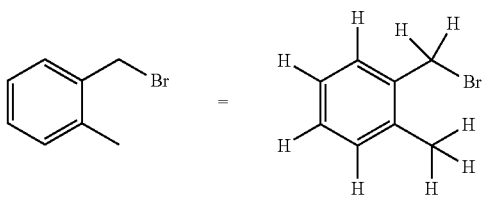

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If an R group is depicted as "floating" on a ring system, as for example with R$^1$ in the group:

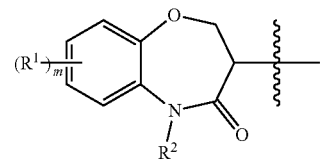

then, unless otherwise defined, a substituent R (e.g., R$^1$ above) can reside on any atom of the fused bicyclic ring system, excluding the atom carrying the bond with the "⁓" symbol, so long as a stable structure is formed.

When a group R is depicted as existing on a ring system containing saturated carbons, as for example in the formula:

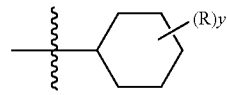

where, in this example, y can be more than one, assuming each replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can be included in a ring, thus creating a spirocyclic ring (a "spirocyclyl" group) structure.

As used herein, the term "substituted" refers to all subsequent modifiers in a term, for example in the term "substituted arylC$_{1-8}$alkyl," substitution may occur on the "C$_{1-8}$ alkyl" portion, the "aryl" portion or both portions of the arylC$_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety can be, unless otherwise specified, —R$^{60}$, halo, =O, —OR$^{70}$, —SR$^{70}$, —N(R$^{80}$)$_2$, haloalkyl, perhaloalkyl, —CN, —NO$_2$, =N$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S) R$^{70}$, —C(NR$^{70}$)R$^{70}$, —CO$_2$M$^+$, —CO$_2$R$^{70}$, —C(S)OR$^{70}$, —C(O)N($R^{80}$)$_2$, —C(N$R^{70}$)($R^{80}$)$_2$, —OC(O)$R^{70}$, —OC(S)$R^{70}$, —OCO$_2^-$M$^+$, —O CO$_2R^{70}$, —OC(S)O$R^{70}$, —N$R^{70}$C(O)$R^{70}$, —N$R^{70}$C(S)$R^{70}$, —N$R^{70}$, CO$_2^-$M$^+$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$ is $C_{1-10}$aliphatic, heteroaliphatic, or cycloaliphatic, typically, $C_{1-6}$aliphatic, more typically $C_{1-6}$alkyl, where $R^{60}$ optionally may be substituted; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has $R^{70}$ substitution, such as H or $C_1$-$C_3$alkyl substitution; and each M$^+$ is a counter ion with a net single positive charge. Each M$^+$ is independently for each occurrence, for example, an alkali metal ion, such as K$^+$, Na$^+$, Li$^+$; an ammonium ion, such as $^+$N($R^{60}$)$_4$; a protonated amino acid ion, such as a lysine ion, or an arginine ion; or an alkaline metal earth ion, such as [Ca$^{2+}$]$_{0.5}$, [Mg$^{2+}$]$_{0.5}$, or [Ba$^{2+}$]$_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N($R^{80}$)$_2$ includes —NH$_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =N$R^{70}$, =N—O$R^{70}$, =N$_2$ or =S.

Substituent groups for replacing hydrogen atoms on unsaturated carbon atoms in groups containing unsaturated carbons are, unless otherwise specified, —$R^{60}$, halo, —O$^-$M$^+$, —O$R^{70}$, —S$R^{70}$, —S$^-$M$^+$, —N($R^{80}$)$_2$, perhaloalkyl, —CN, —OCN, —SCN, —NO, —NO$_2$, —N$_3$, —SO$_2R^{70}$, —SO$_3^-$M$^+$, —SO$_3R^{70}$, —OSO$_2R^{70}$, —OSO$_3^-$M$^+$, —OSO$_3R^{70}$, —PO$_3^{-2}$(M$^+$)$_2$, —PO$_3^{-2}$M$^{2+}$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —CO$_2^-$M$^+$, —CO$_2R^{70}$, —C(S)O$R^{70}$, —C(O)N$R^{80}R^{80}$, —C(N$R^{70}$)N($R^{80}$)$_2$, —OC(O)$R^{70}$, —OC(S)$R^{70}$, —OCO$_2^-$M$^+$, —OCO$_2R^{70}$, —OC(S)O$R^{70}$, —N$R^{70}$C(O)$R^{70}$, —N$R^{70}$C(S)$R^{70}$, —N$R^{70}$CO$_2^-$M$^+$, —NRCO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined. In an independent embodiment, the substituents are not —O$^-$M$^+$, —O$R^{70}$, —S$R^{70}$, or —S$^-$M$^+$.

Substituent groups for replacing hydrogen atoms on nitrogen atoms in groups containing such nitrogen atoms are, unless otherwise specified, —$R^{60}$, —O$^-$M$^+$, —O$R^{70}$, —S$R^{70}$, —S$^-$M$^+$, —N($R^{80}$)$_2$, perhaloalkyl, —CN, —NO, —NO$_2$, —S(O)$_2R^{70}$, —SO$_3^-$M$^+$, —SO$_3R^{70}$, —OS(O)$_2R^{70}$, —OSO$_3^-$M$^+$, —OSO$_3R^{70}$, —PO$_3^{2-}$(M$^+$)$_2$, —PO$_3^{2-}$M$^{2+}$, —P(O)(O$R^{70}$)O$^-$M$^+$, —P(O)(O$R^{70}$)(O$R^{70}$), —C(O)$R^{70}$, —C(S)$R^{70}$, —C(N$R^{70}$)$R^{70}$, —CO$_2R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OCO$_2R^{70}$, —OC(S)O$R^{70}$, —N$R^{70}$C(O)$R^{70}$, —N$R^{70}$C(S)$R^{70}$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, or aromatic (including both aryl and heteroaryl). Exemplary acyl moieties include, but are not limited to, —C(O)H, —C(O)alkyl, —C(O)$C_1$-$C_6$alkyl, —C(O)$C_1$-$C_6$haloalkyl, —C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups (as well as alkylene, alkenylene, or alkynylene groups), cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl or a substituted or unsubstituted cycloalkyl group; —CH$_2$CH$_2$—O—CH$_2$CH$_3$ is an exemplary alkoxyalkyl group.

"Alkyl" refers to a saturated aliphatic hydrocarbyl group having from 1 to at least 25 (C$_{1-25}$) carbon atoms, more typically 1 to 10 (C$_{1-10}$) carbon atoms such as 1 to 6 (C$_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH (CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

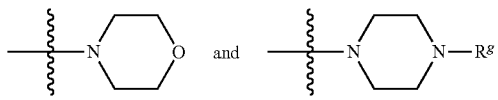

wherein R$^g$ is R$^{70}$, —C(O)R$^{70}$, —C(O)OR$^{60}$ or —C(O)N (R$^{80}$)$_2$.

"Amide" refers to the group —N(R)acyl, wherein R is hydrogen, heteroaliphatic, or aliphatic, such as alkyl, particularly C$_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

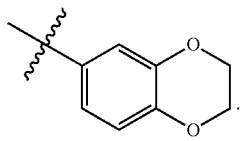 [SMILES: *c1ccc2c(c1)OCCO2]

However, in certain examples, context or express disclosure may indicate that the point of attachment is through a non-aromatic portion of the condensed ring system. For example,

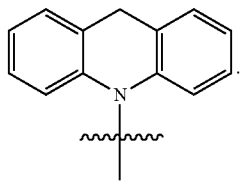 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" refers to —CO$_2$H.

"Carboxamide" refers to —C(O)amino.

"Carboxyl ester" or "carboxy ester" refers to the group —C(O)OR, where R is aliphatic, heteroaliphatic, or aromatic (including both aryl and heteroaryl).

"Carboxylate" refers to —C(O)O— or salts thereof.

"Cyano" refers to the group —CN.

"Cycloaliphatic" refers to a cyclic aliphatic group having a single ring (e.g., cyclohexyl), or multiple rings, such as in a fused, bridged or spirocyclic system, the ring or at least one of the rings in the system is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaliphatic" refers to an aliphatic compound or group having at least one heteroatom and at least one carbon atom, i.e., at least one carbon atom from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety having, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —$NO_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as +N(R")$_4$ where R" is H, aliphatic, heteroaliphatic, or aromatic (including both aryl and heteroaryl); or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" may refer generally to any living being, but more typically refers to mammals and other animals, particularly humans. Thus disclosed methods are applicable to both human therapy and veterinary applications.

"Pharmaceutically acceptable excipient" refers to a substance, other than the active ingredient, that is included in a composition comprising the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is a component that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as amino acids, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or pharmaceutical composition refers to an amount of the compound or pharmaceutical composition sufficient to achieve a particular desired result, such as to inhibit a protein or enzyme. In particular embodiments, an "effective amount" is an amount sufficient to inhibit RIP1; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the size, age, and gender of the patient to be treated and the like, as will be understood by a person of ordinary skill in the art.

"Prodrug" refers to compounds that are transformed in vivo to yield a biologically active compound, or a compound more biologically active than the parent compound. In vivo transformation may occur, for example, by hydrolysis or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—$P(O)(OR')_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, or aromatic (including both aryl and heteroaryl).

"Sulfanyl" refers to the group or —SH, —S-aliphatic, —S-heteroaliphatic, —S-aromatic, (including both -S-aryl and —S-heteroaryl).

"Sulfinyl" refers to the group or moiety —S(O)H, —S(O)aliphatic, —S(O)heteroaliphatic, or —S(O)aromatic (including both —S(O)aryl and —S(O)heteroaryl).

"Sulfonyl" refers to the group: —SO$_2$H, —SO$_2$aliphatic, —SO$_2$heteroaliphatic, —SO$_2$aromatic (including both —SO$_2$aryl and —SO$_2$heteroaryl).

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing diminution of a symptom or regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate enantiomers and/or stereoisomer using techniques known to those of ordinary skill in the art, particularly with the benefit of the present disclosure. In cases of limited rotation, e.g. around the amide bond or between two directly attached rings such as pyridinyl rings, biphenyl groups, and the like, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl refers to both $C_2H_5$ or $C_2H_5$ where from 1 to 5 hydrogens are replaced by deuterium, such as in $C_2D_xH_{5-x}$.

II. RIP1-Active Compounds and Pharmaceutical Compositions Comprising RIP1-Active Compounds A. Compounds Disclosed herein are compounds and pharmaceutical compositions comprising such compounds that are useful for inhibiting RIP1 and/or for treating diseases and/or conditions associated with RIP1. In some embodiments, the compounds are selective kinase inhibitors. For example, exemplary compounds are able to selectively inhibit RIP1 over RIP2, RIP3, or both RIP2 and RIP3.

In some embodiments, a compound of the present disclosure has a structure according to Formula I

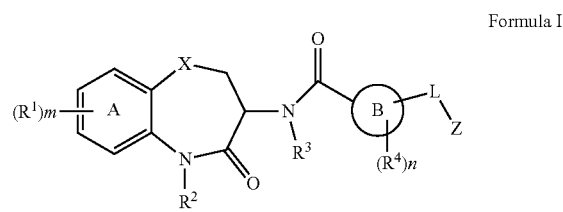

Formula I or a pharmaceutically acceptable salt thereof. A person of ordinary skill in the art will appreciate that compounds within the scope of Formula I also include stereoisomers, N-oxides, tautomers, hydrates, solvates, isotopes, and/or prodrugs thereof, unless otherwise specified. With respect to Formula I, ring B is heteroaryl, and may be a monocyclic heteroaryl. In some embodiments, ring B is a 5-membered or 6-membered heteroaryl. In some embodiments, ring B is a 5-membered or 6-membered heteroaryl where the heteroaryl has one or two ring nitrogen atoms and the remainder of the ring atoms are carbon, that is, ring B is not a triazole, triazine, or a heteroaryl comprising an oxygen or sulfur ring atom, such as oxazole, thiazole or isoxazole.

In certain embodiments, ring B is pyrazolyl, and in other particular embodiments, ring B is pyridinyl.

Each $R^1$ independently is halogen or -linker-$R^6$ group, wherein the linker is a bond or $R^a$, provided that $R^a$ is not H or D, and $R^6$ is heterocyclyl, $R^b$, —C($R^f$)$_3$, or —C($R^f$)=C($R^f$)$_2$. In some embodiments, $R^1$ is halogen, such as fluoro, chloro, bromo, or iodo, typically bromo. In certain other embodiments, each $R^1$ independently is -linker-$R^6$.

$R^2$ is $R^a$. In some embodiments, $R^2$ is H or $C_{1-10}$aliphatic, such as H or $C_{1-6}$alkyl, and in certain embodiments, $R^2$ is $C_{1-6}$alkyl, such as $CH_3$ or $CD_3$.

$R^3$ is $R^a$. In some embodiments, $R^3$ is H or $C_{1-10}$aliphatic, such as H or $C_{1-6}$alkyl, and in certain embodiments, $R^3$ is H.

If present, each $R^4$ independently is $R^e$, and may be halogen, such as F, Cl, Br, or I, or $C_{1-10}$aliphatic, such as $C_{1-6}$alkyl, for example, methyl.

L is a heteroatom or $R^a$, provided that $R^a$ is not H or D. In some embodiments, L is oxygen or $C_{1-10}$alkyl, such as $C_{1-6}$alkyl, more particularly methylene (—CH$_2$—).

X is CH$_2$ or O.

Z is heteroaryl, and may be a monocyclic heteroaryl.

m is 1, 2, 3, or 4. In some embodiments, m is 1, 2 or 3, and may be 1 or 2, and in certain embodiments, m is 1.

n is 0, 1 or 2, and may be 0 or 1.

$R^a$ is independently for each occurrence H or D, except for embodiments where L is $R^a$; $C_{1-10}$aliphatic; $C_{1-10}$haloaliphatic; $C_{5-10}$aromatic; $C_{3-6}$heterocyclic; or $C_{3-10}$spiroheterocyclic.

$R^b$ is independently for each occurrence —OH, —SH, —OR$^c$, —SR$^c$, —NR$^d$R$^d$, —Si(R$^a$)$_3$, —C(O)OH, —C(O)OR$^c$, —C(O)NR$^d$R$^d$, —OC(O)NR$^d$R$^d$, —OC(O)C$_{1-10}$alkyl substituted with one or two NR$^d$R$^d$, carboxyl, or a combination thereof, and optionally further substituted with an aromatic moiety, —SH, —O-acyl, or —C(O)NH$_2$.

$R^c$ is independently for each occurrence $C_{1-10}$alkyl, which can be substituted with 1, 2 or 3 $R^e$, $C_{2-10}$alkenyl, which can be substituted with 1, 2 or 3 $R^e$, $C_{2-10}$alkynyl, which can be substituted with 1, 2 or 3 $R^e$, $C_{3-6}$cycloalkyl, which can be substituted with 1, 2 or 3 $R^e$, or $C_{5-10}$aromatic, which can be substituted with 1, 2 or 3 $R^e$.

$R^d$ is independently for each occurrence H; $C_{1-6}$alkyl, which can be substituted with 1, 2 or 3 $R^e$ or a $C_{3-9}$heterocyclyl; $C_{3-6}$cycloalkyl, which can be substituted with 1, 2 or 3 $R^e$; $C_{3-6}$heterocyclic, which can be substituted with 1, 2 or 3 $R^e$; $C_{5-10}$aryl, which can be substituted with 1, 2 or 3 $R^b$; $C_{5-10}$heteroaryl, which can be substituted with 1, 2 or 3 $R^e$; or two $R^d$ groups together with the nitrogen bound thereto provide a $C_{3-9}$heterocyclic, which can be substituted with one or more $R^e$), or a $C_{5-10}$heteroaryl, which can be substituted with one or more $R^e$.

$R^e$ is independently for each occurrence halogen, $C_{1-6}$alkyl, $C_{2-10}$alkenyl, $C_{2-10}$alkynyl, $C_{1-6}$haloalkyl, $C_{3-6}$cycloalkyl, $C_{5-10}$heteroaryl, or —OR$^a$.

And $R^f$ is independently for each occurrence -alkylphosphate, $R^a$, $R^b$, or $R^e$, or two $R^f$ groups together with the carbon atom bound thereto provide a $C_{2-6}$alkenyl group, a $C_{3-6}$cycloalkyl group, which can be substituted with one or more $R^e$, or a $C_{3-10}$heterocyclic, which can be substituted with one or more $R^e$ or acyl.

In some embodiments, n is 0. In other embodiments, n is 1, and in such embodiment, R may be $C_{1-6}$alkyl, such as methyl.

In certain embodiments of Formula I, ring B is pyridinyl or pyrazolyl; L is a heteroatom or $C_{1-10}$alkyl; Z is heteroaryl; each $R^1$ is heterocyclyl, or $C_{1-10}$aliphatic; $R^2$ is H or $C_{1-6}$alkyl; $R^3$ is H, $C_{1-6}$alkyl; m is 1; and n is 0.

In any embodiments, Z may be a 5-membered or 6-membered heteroaryl, such as a 5-membered or 6-membered nitrogen-containing heteroaryl, for example, pyridinyl, pyridazinyl, pyrimidinyl, pyrazinyl, pyrazolyl, imidazolyl, pyrrolyl, or triazolyl. In certain such embodiments, Z is a 6-membered heteroaryl, such as a 6-membered nitrogen-containing heteroaryl, and may be pyridinyl, pyrimidinyl or pyridazinyl.

In any embodiments, Z may be unsubstituted, or Z may be substituted as defined herein. In some embodiments, Z is substituted with halogen, $C_{1-6}$alkyl, $C_{1-6}$haloalkyl, or OH, and in particular embodiments, Z is unsubstituted or substituted with OH, CH$_3$, F, or CF$_3$.

In any embodiments, ring B may be a 5-membered heteroaryl ring with at least one ring nitrogen atom, such as one, two or three, preferably one or two, more preferably two ring nitrogen atoms, and the remaining ring atoms being carbon. In some embodiments, the —N(R$^3$)C(O)— moiety is attached to ring B at a ring nitrogen atom on ring B.

In some embodiments, ring B is pyrazolyl and the —N(R$^3$)C(O)— moiety is attached to ring B at a ring nitrogen atom on ring B.

In some embodiments, X is O. And in some other embodiments, X is CH$_2$.

In any embodiments, each $R^1$ independently may be heterocyclyl, unsubstituted $C_{1-10}$aliphatic, or $C_{1-10}$aliphatic substituted with one or two substituents selected from —OH, halogen, carboxyl, carboxyl ester, heterocyclyl, amino, alkoxy, phosphate, cycloalkyl, alkenyl, —OC(O)NH($C_{1-4}$alkyl)-amino, —OC(O)R$^8$, or —OC(O)(CHR$^9$)$_2$CO$_2$H. The —OC(O)—R$^8$ moiety is derived from an amino acid where the —OC(O)— moiety of —OC(O)—R$^8$ corresponds to an acid moiety on the amino acid and R$^8$ comprises —N(R$^{10}$)$_2$ or a nitrogen-containing nonaromatic heterocyclyl, where R$^{10}$ is H or carboxyl ester. And each R$^9$ independently is H or —O-acyl.

With respect to the —OC(O)—R$^8$ moiety, the nitrogen-containing nonaromatic heterocyclyl may be a 5- or 6-membered unsaturated nitrogen-containing heterocyclyl, for example, pyrrolidinyl. The amino acid can be any amino acid, such as a naturally occurring amino acid, and may be an amino acid selected from glycine, valine, alanine, leucine, isoleucine, methionine, phenylalanine, tryptophan, tyrosine, serine, threonine, asparagine, glutamine, arginine, histidine, lysine, aspartic acid, glutamic acid, cysteine, or proline. A person of ordinary skill in the art will understand that where the amino acid comprises one or more chiral center, all enantiomers, diastereomers and/or mixtures thereof are contemplated. For example, the amino acid may be the L-amino acid, the D-amino acid or a mixture thereof. In some embodiments, the amino acid is the L-amino acid. And in certain embodiments, —OC(O)—R$^8$ is —OC(O)CH(NH$_2$)R$^{11}$,

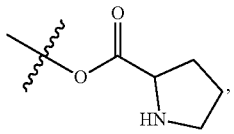 [SMILES: *OC(=O)C1CCCN1]

or —OC(O)—(CH$_2$)$_{1-2}$C(NH$_2$)CO$_2$H, where R$^{11}$ is an amino acid side chain, and/or may be H, —CH$_3$, isopropyl, —CH$_2$CH(CH$_3$)$_2$, —CH(CH$_3$)Et, —CH$_2$CH$_2$SCH$_3$,

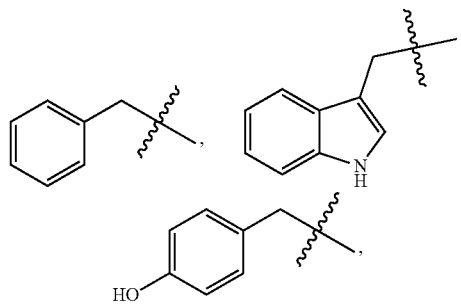

—CH$_2$OH, —CH(OH)CH$_3$, —CH$_2$C(O)NH$_2$, —CH$_2$CH$_2$C(O)NH$_2$, —CH$_2$SH, —CH$_2$CH$_2$CH$_2$NHC(O)(NH)NH$_2$,

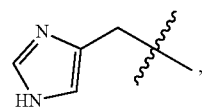 [SMILES: *Cc1c[nH]cn1]

CH$_2$CH$_2$CH$_2$CH$_2$NH$_2$, —CH$_2$CO$_2$H, or CH$_2$CH$_2$CO$_2$H.

Also with respect to $R^1$, at least one $R^1$ may be an 8- to 12-membered spiroheterocyclyl, $C_{1-10}$alkyl or a $C_{2-10}$alkyne. The $C_{1-10}$alkyl or the $C_{2-10}$alkyne may be linear, branched, and/or cyclic, and have one or two substituents. One substituent may be OH. In some embodiments, one substituent is oxetanyl, azetidinyl, pyridinyl, pyrrolidinyl, piperidinyl, tetrahydropyranyl, amino, or phosphate, and/or in some embodiments, one substituent is —OC(O)—$R^8$. The $C_{1-10}$alkyl or the $C_{2-10}$alkyne may comprise a linear and/or branched section and a cyclic section, for example, as in

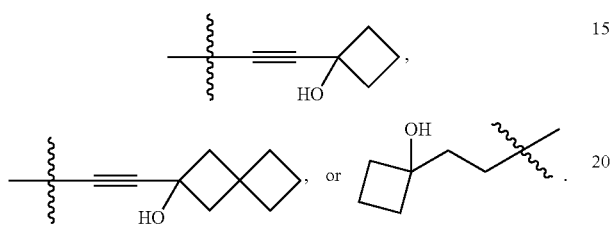

In some embodiments, Z is

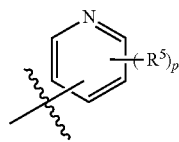

where if present, each $R^5$ independently is $R^e$, and p is 0, 1, 2, 3, or 4, typically, 0, 1 or 2, more typically 0 or 1, and in some embodiments, p is 0 and in other certain embodiments, p is 1. In any embodiments, each $R^5$ independently may be OH, halogen, $C_{1-6}$alkyl, or $C_{1-6}$haloalkyl, such as OH, $CF_3$, methyl or fluoro. In some embodiments, p is 1, but in other embodiments, p is 0. And in certain embodiments, the -L-Z moiety is (6-fluoropyridin-2-yl)methyl, (6-methylpyridin-2-yl)methyl, (2-methylpyridin-5-yl)oxy, (2-fluoropyridin-5-yl)oxy, pyridin-2-ylmethyl, (6-trifluoromethylpyridin-2-yl)methyl, (6-hydroxypyridin-2-yl)methyl, pyridin-3-ylmethyl, pyridazin-3-ylmethyl, (2-methylpyridin-5-yl)methyl, (2-fluoropyridin-5-yl)methyl, (2-fluoropyridin-3-yl)methyl, (2,6-difluoropyridin-3-yl)methyl, pyrimidin-2-ylmethyl, or pyridin-4-ylmethyl.

In some embodiments of Formula I, the compound may have a structure according to formulas I-1 or I-2:

Formula I-1

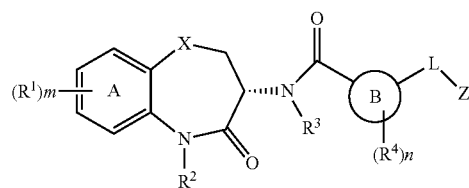

-continued

Formula I-2

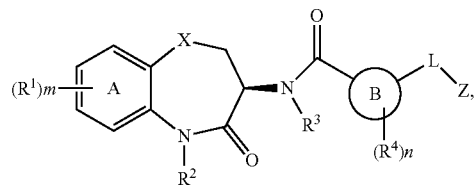

or a pharmaceutically acceptable salt, N-oxide, solvate, tautomer, or stereoisomer thereof.

In some embodiments, the compound may have a structure according to one or more of the following formulas Formula I-3

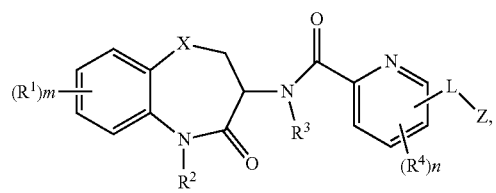

Formula I-4

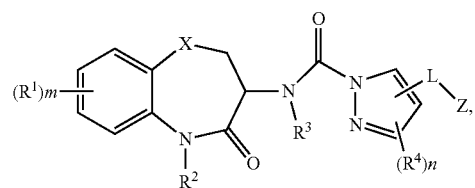

Formula I-5

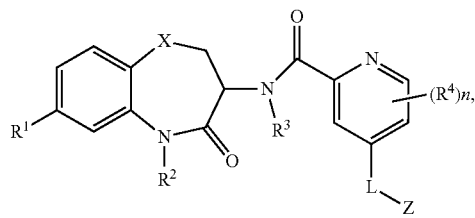

Formula I-6

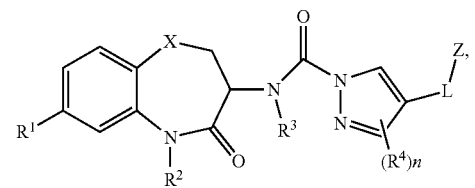

Formula I-7

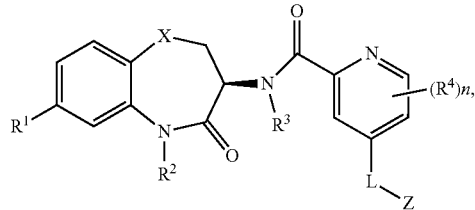

-continued

Formula I-8
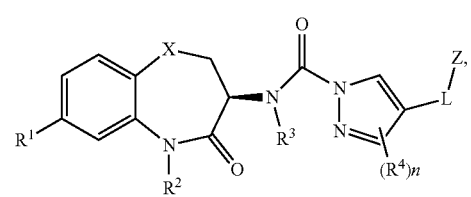

Formula I-9
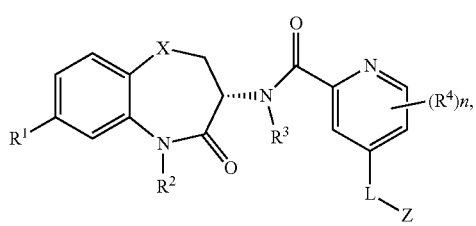

Formula I-10
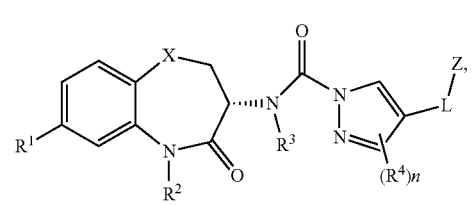

Formula I-11
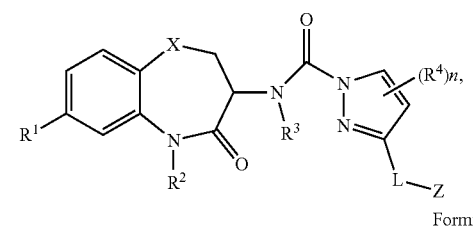

Formula I-12
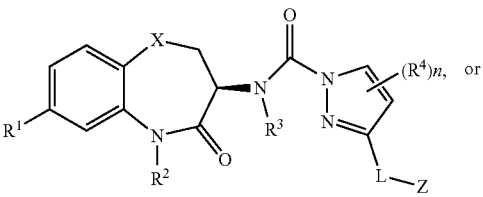

Formula I-13
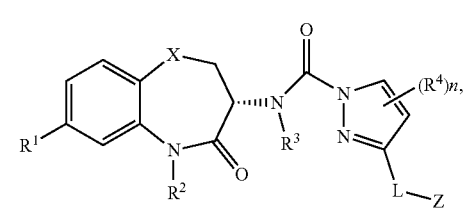

or a pharmaceutically acceptable salt, N-oxide, solvate, tautomer, or stereoisomer thereof. With respect to Formulas I-1 to I-13, ring B, L, X, Z, $R^1$, $R^2$, $R^3$, $R^4$, m and n, if present, are as defined herein for Formula I.

In any of the above embodiments concerning Formula I and/or Formulas I-1 through I-13, $R^1$ may be selected from any of the following:

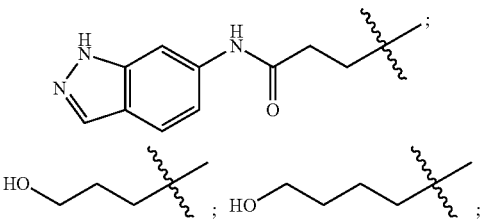

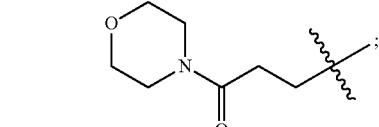

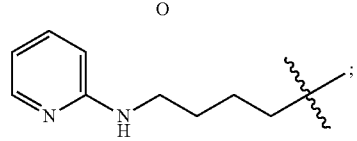

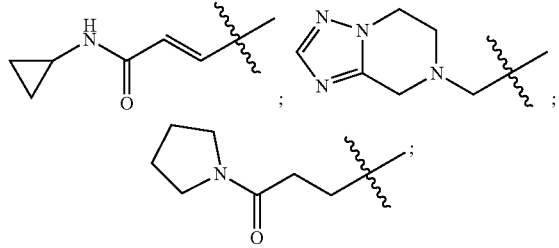

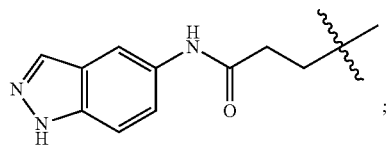

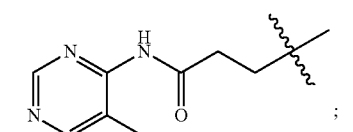

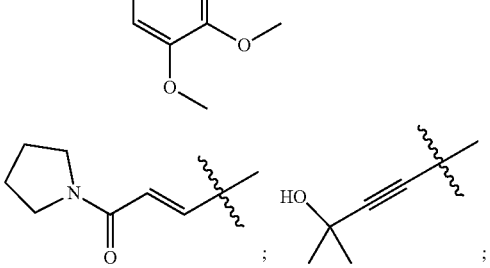

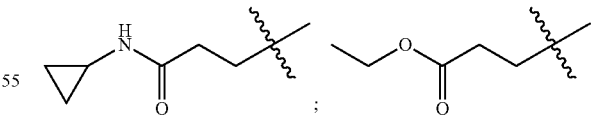

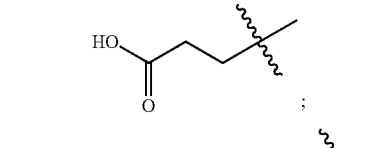

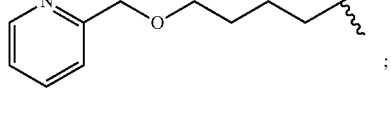

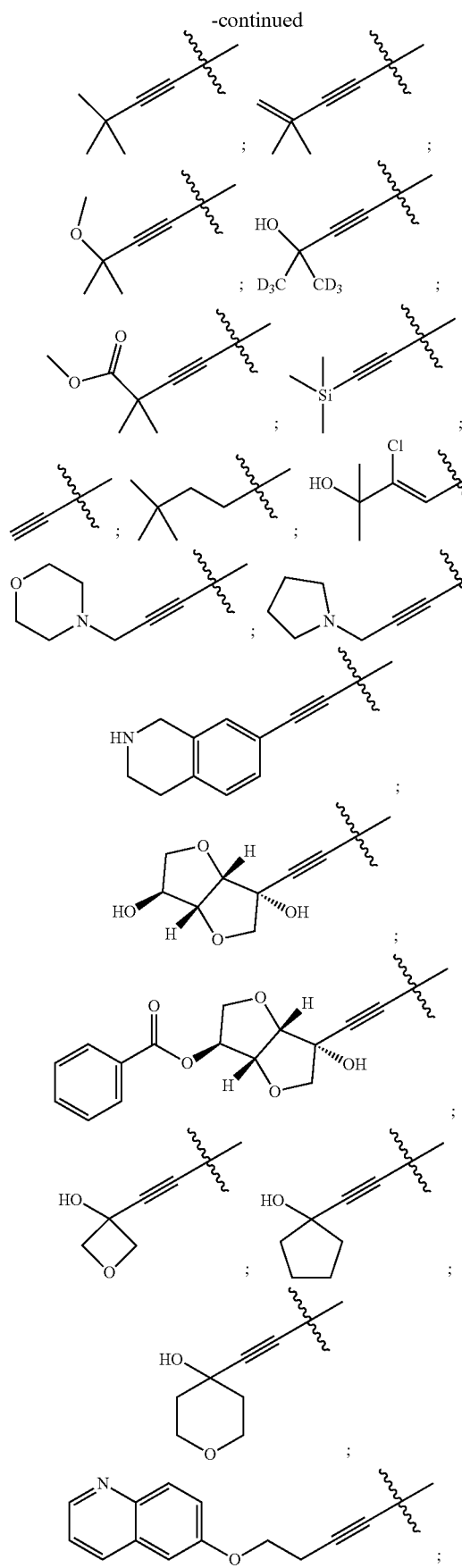
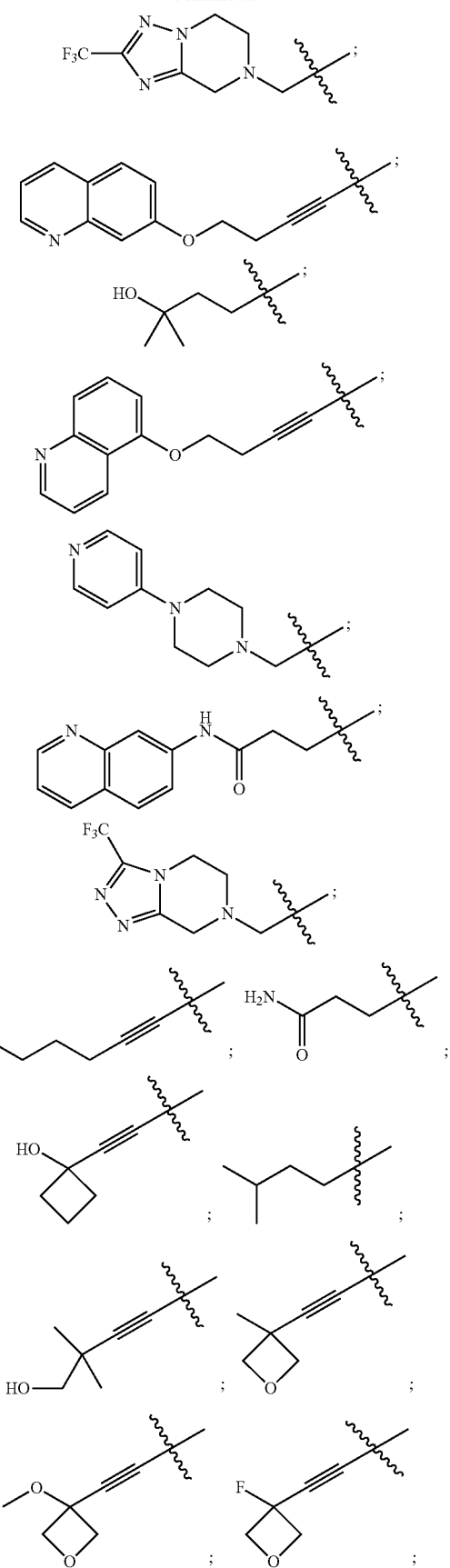

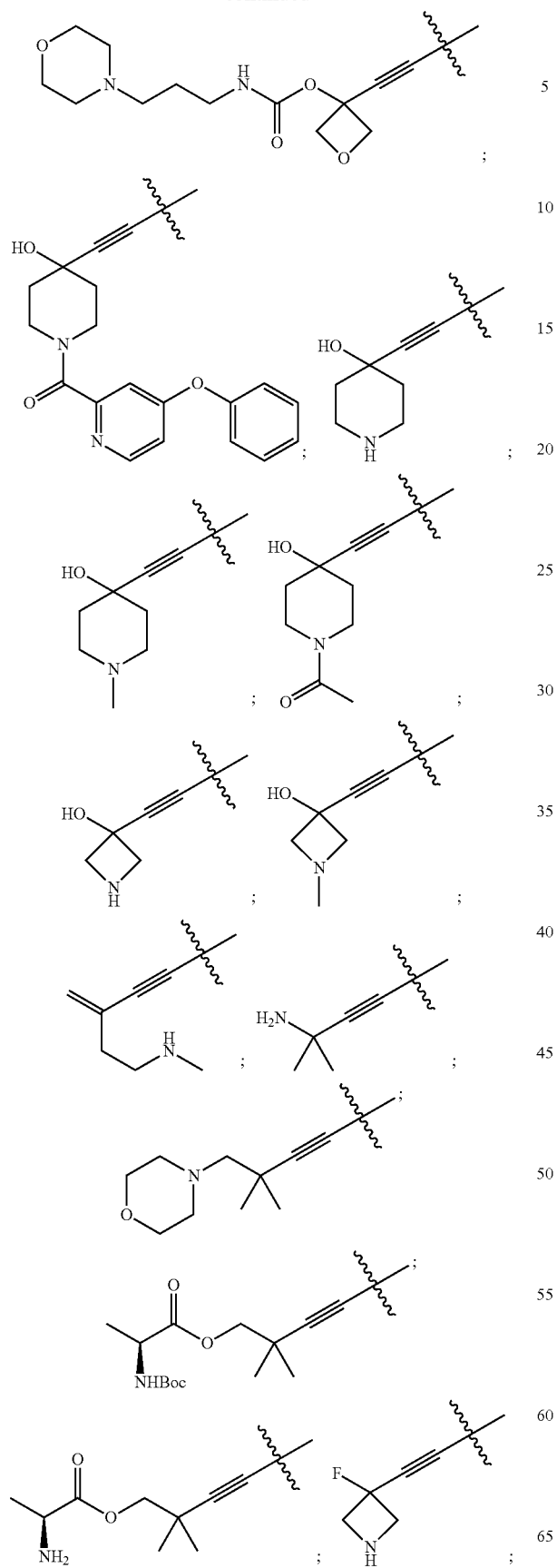
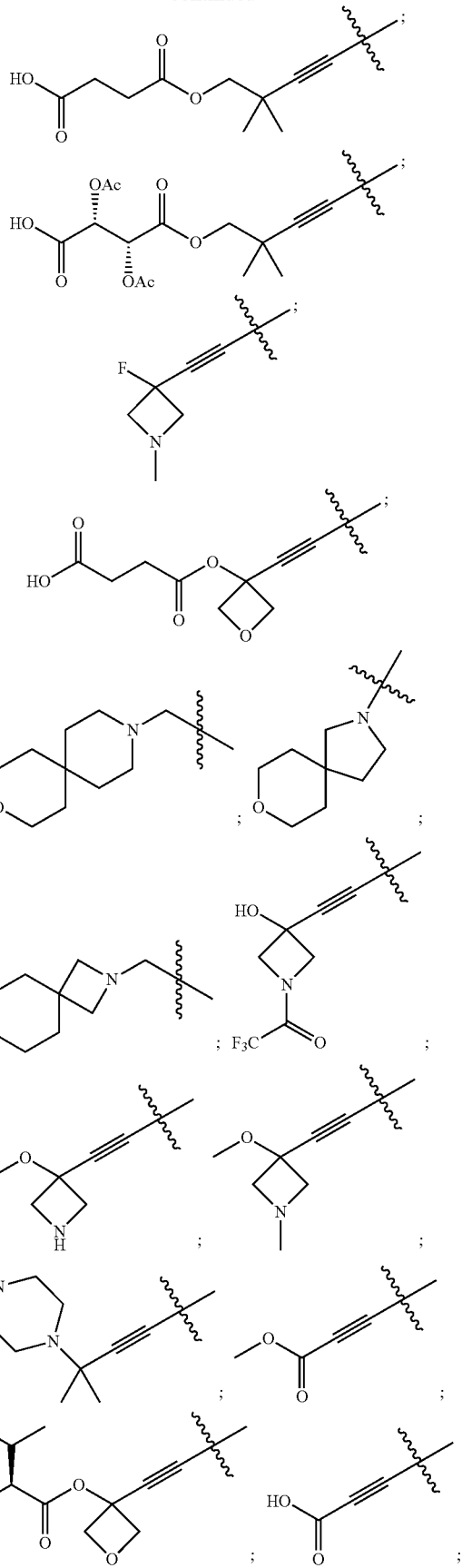

-continued

-continued
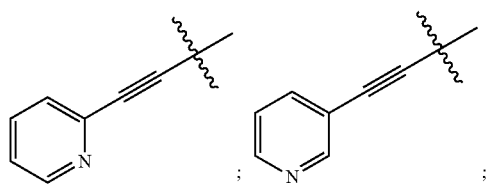
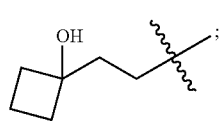
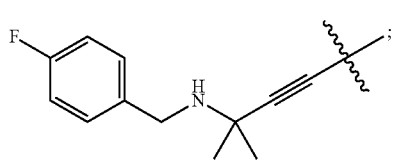
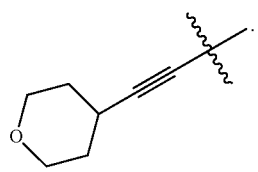
And in certain embodiments, of Formula I and/or Formulas I-1 through I-13, R$^1$ may be selected from any of the following:
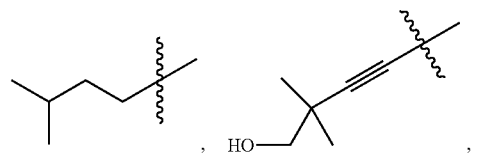
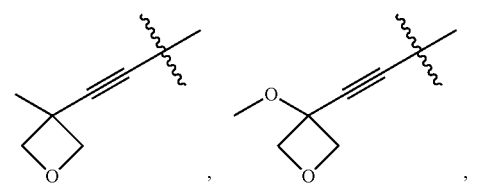
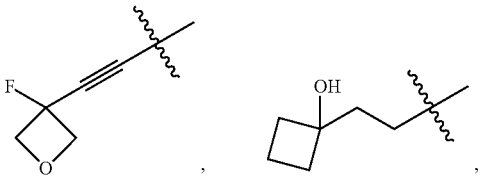
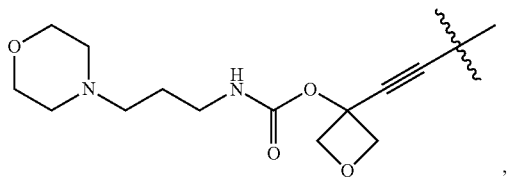
-continued
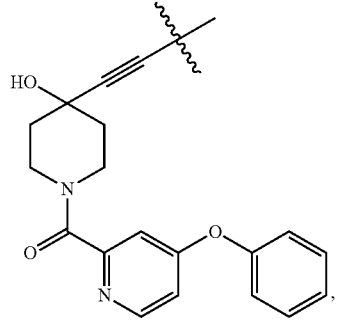
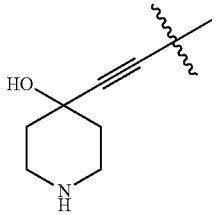 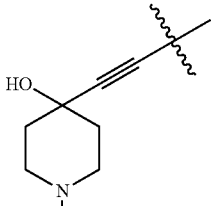
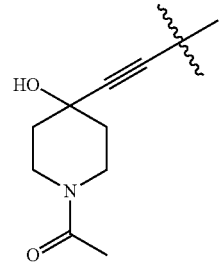 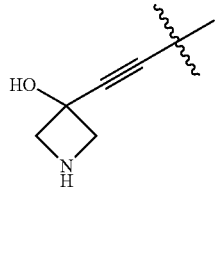
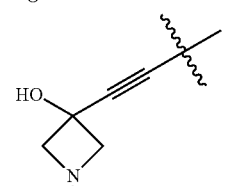 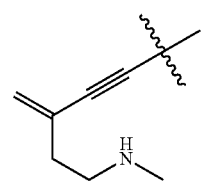
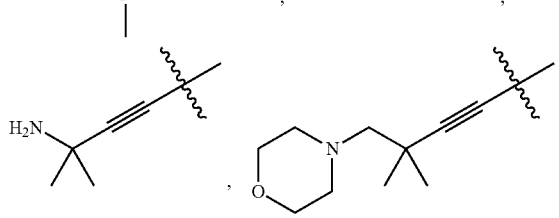
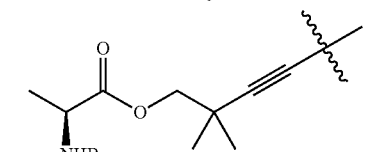
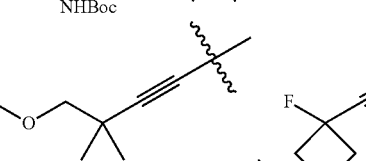
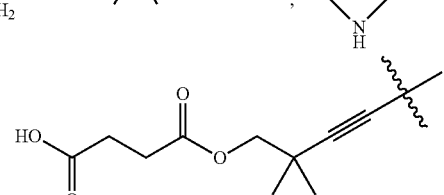

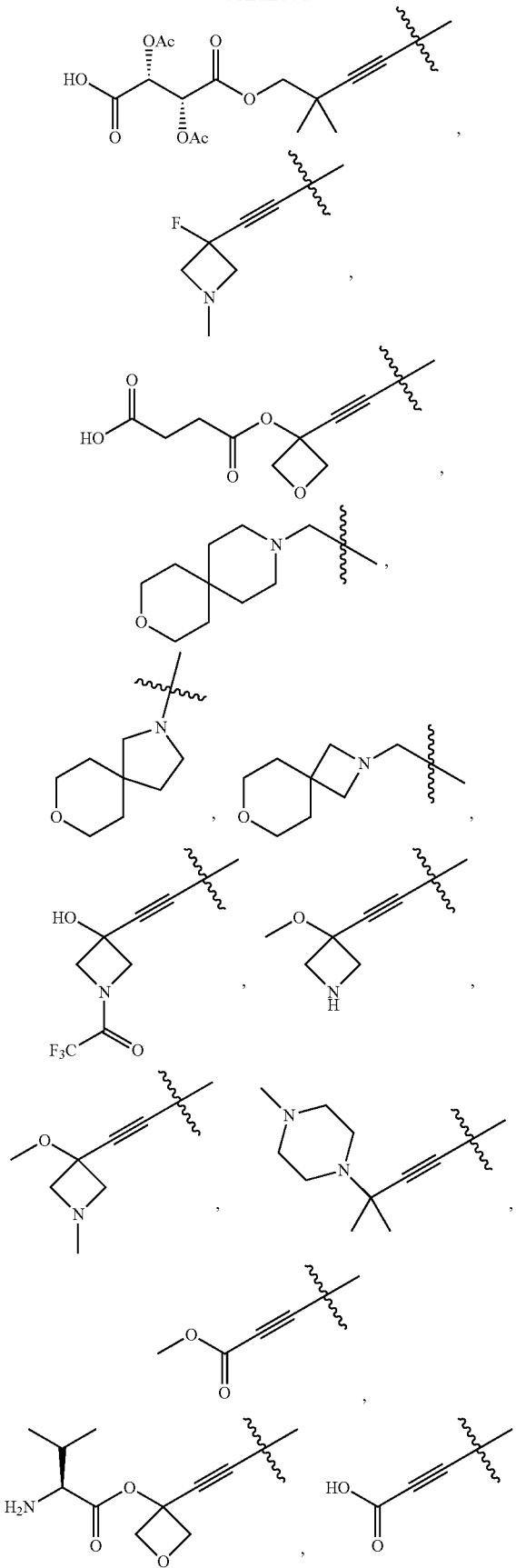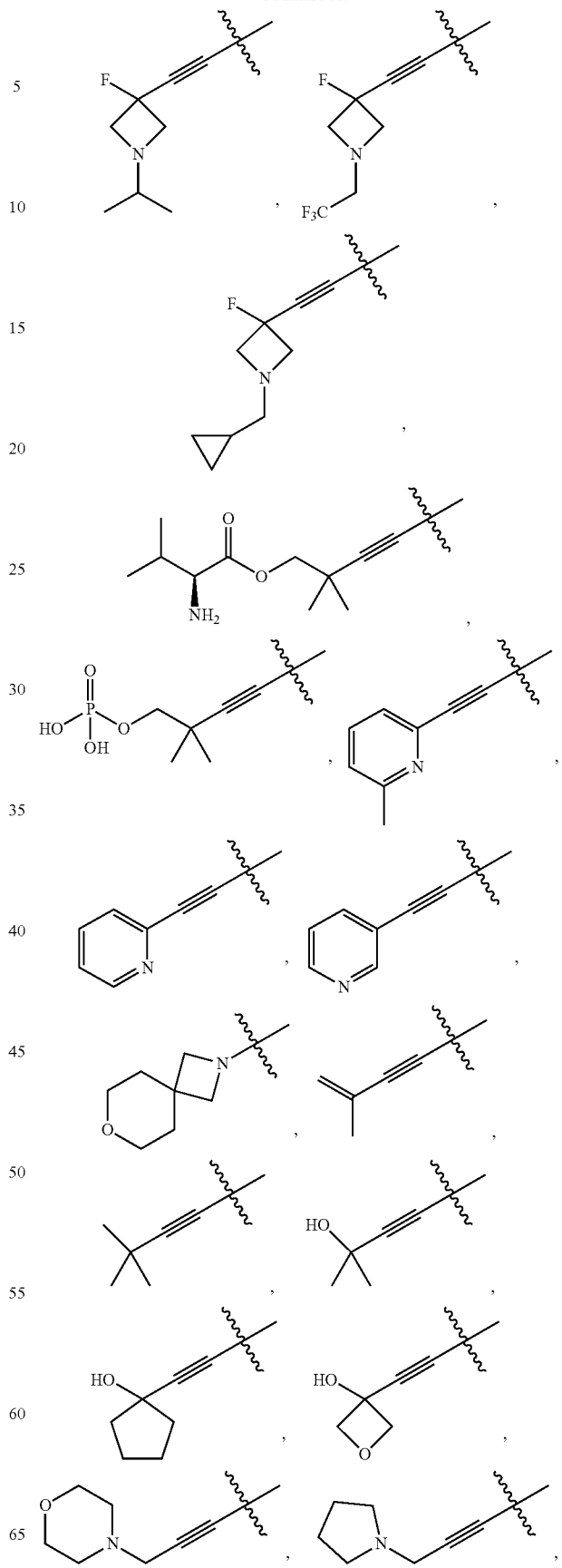

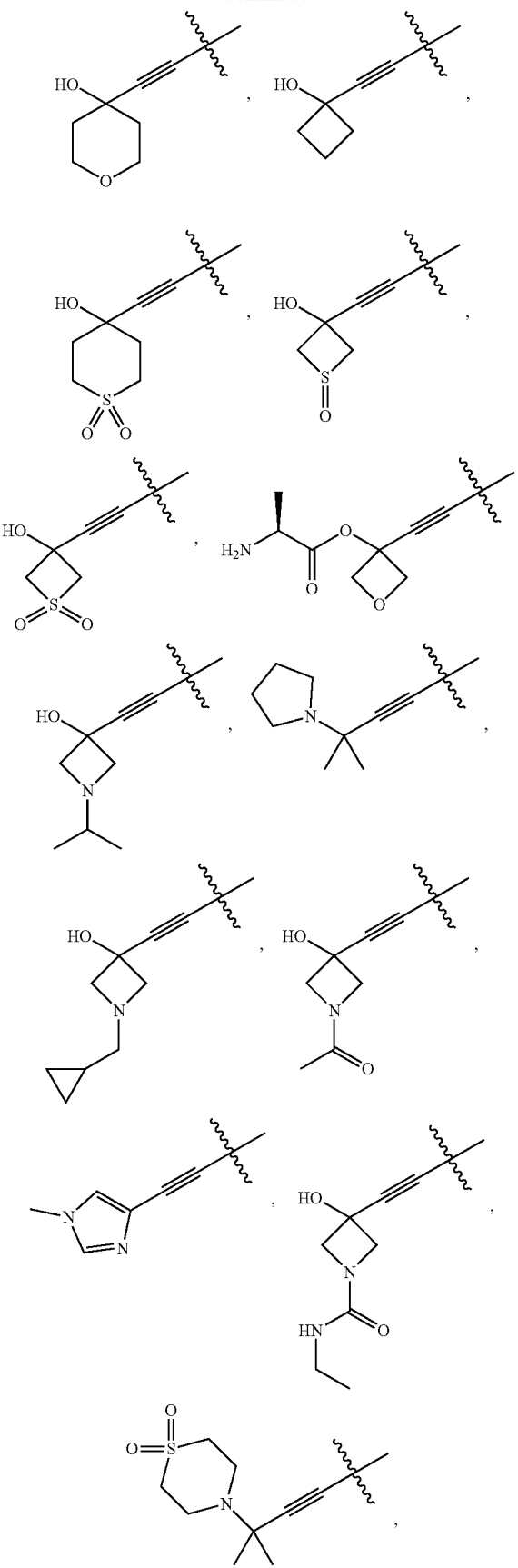
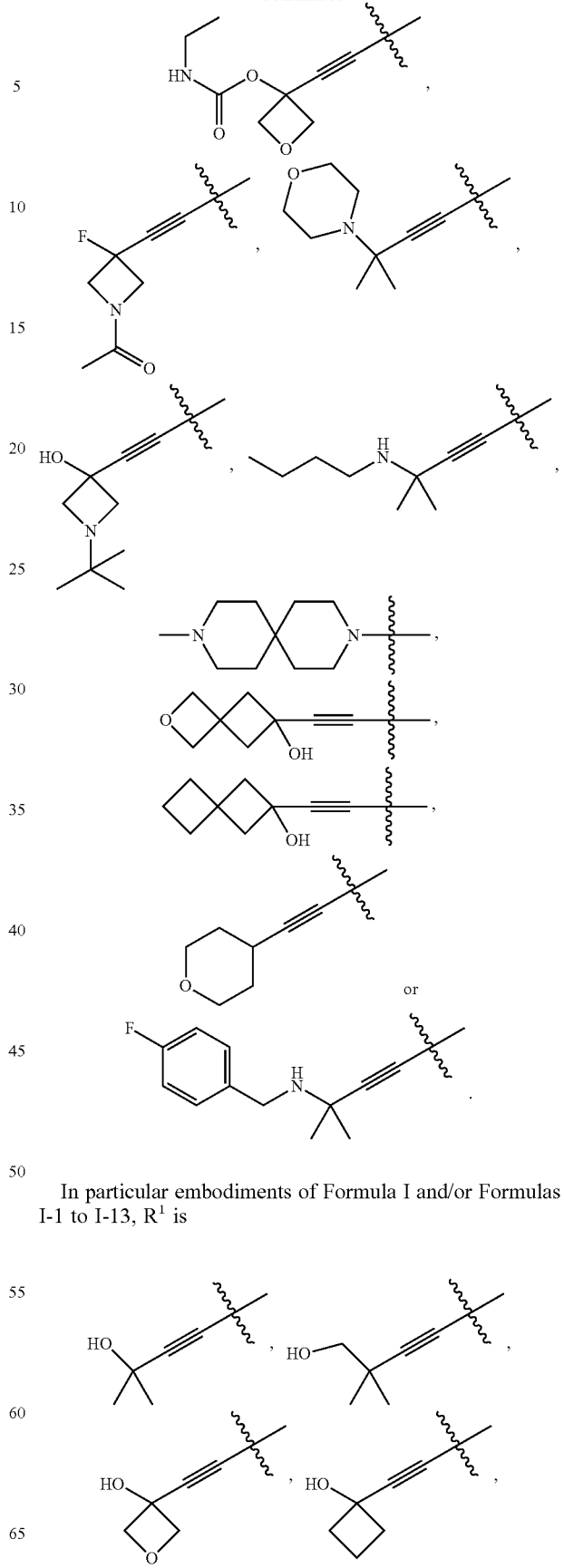
In particular embodiments of Formula I and/or Formulas I-1 to I-13, $R^1$ is

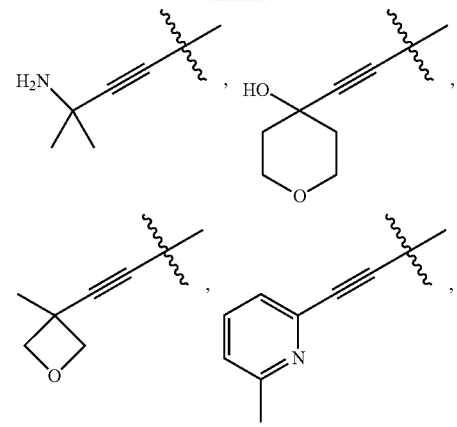
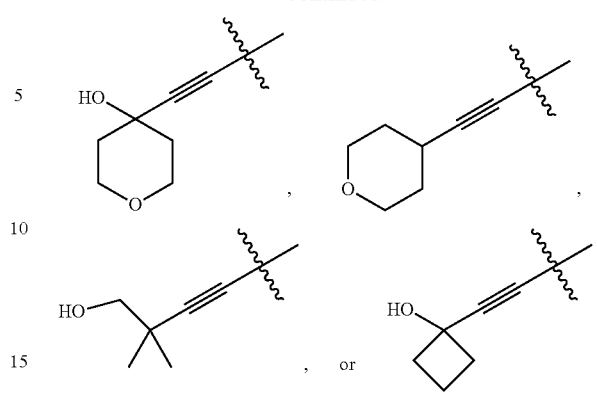
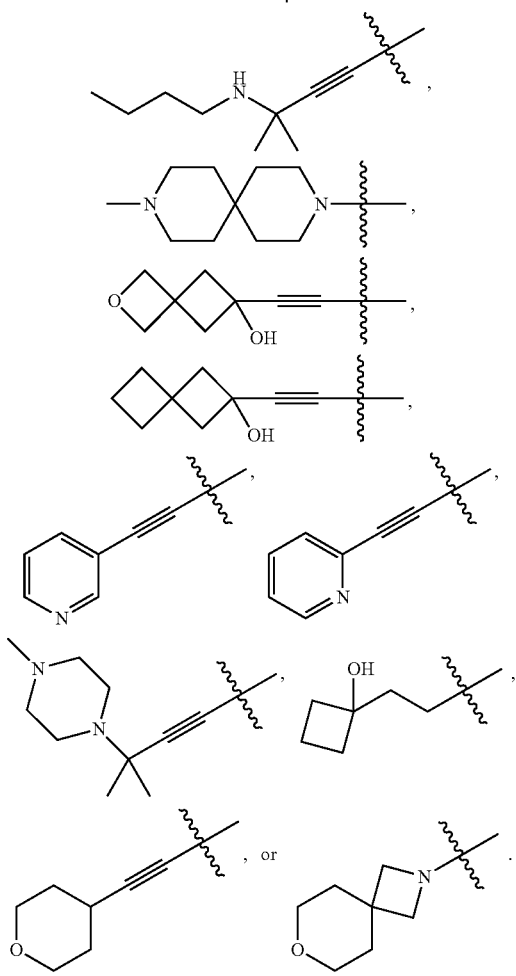
In other embodiments of Formula I and/or Formulas I-1 to I-13, R¹ is halogen, such as Br.
Certain disclosed exemplary compounds within the scope of one or more of Formulas I,
I-1
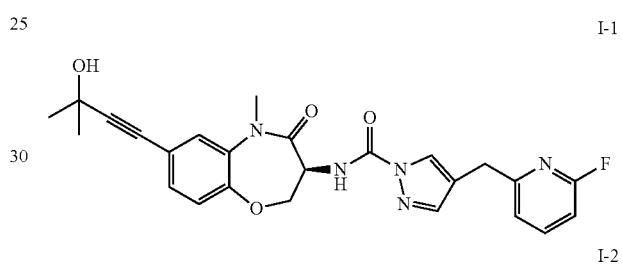
I-2
I-3
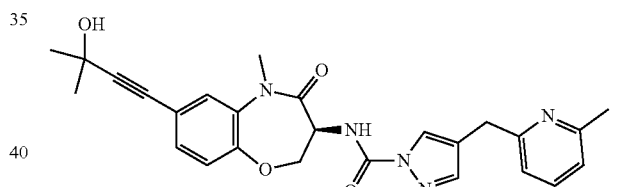
I-4
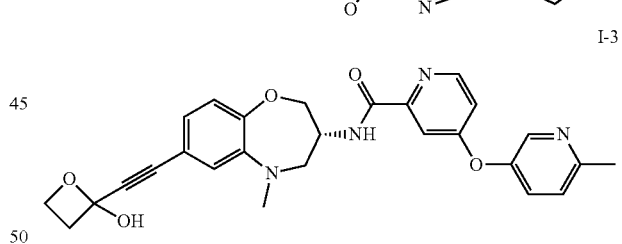
I-5
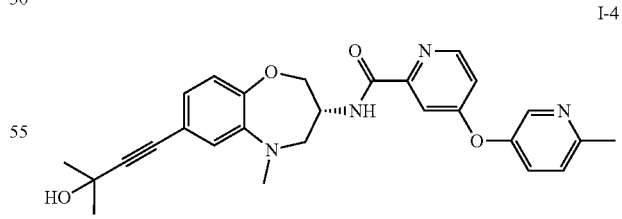
And in other particular embodiments of Formula I and/or Formulas I-1 to I-13, R¹ is
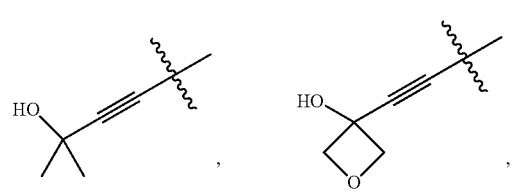

-continued
I-6
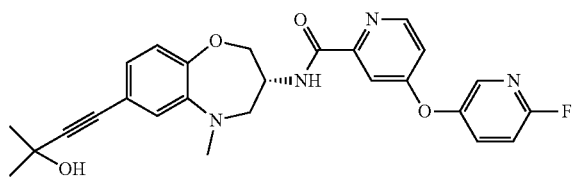
I-7
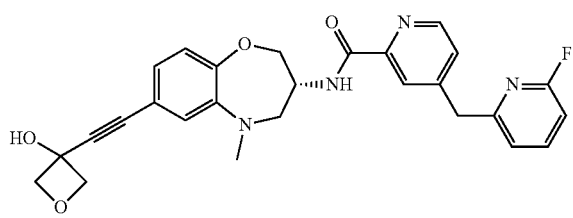
I-8
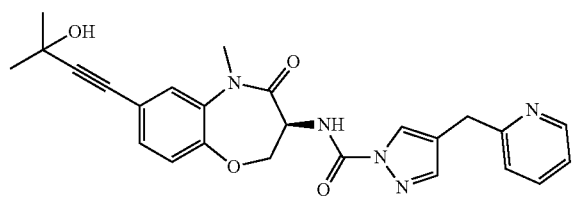
I-9
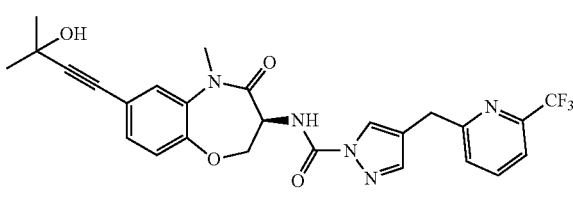
I-10
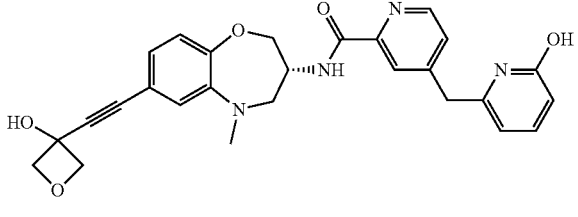
I-11
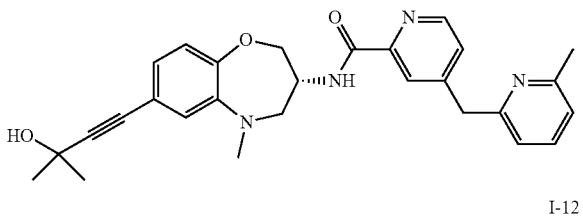
I-12
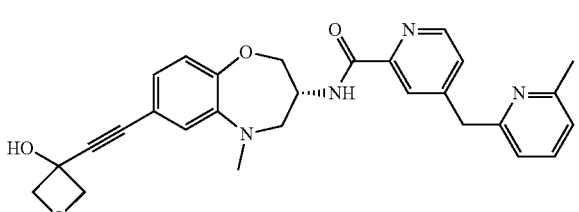
I-13
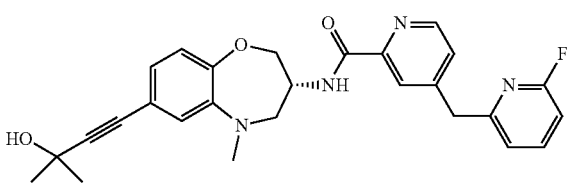
I-14
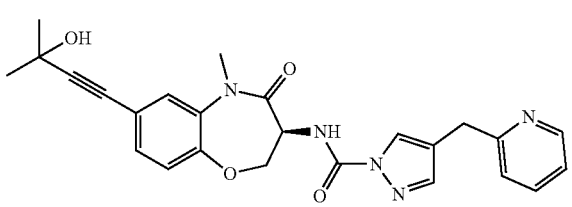
I-15
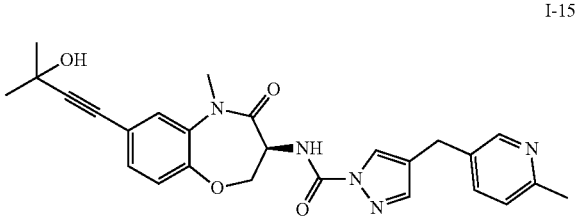
I-16
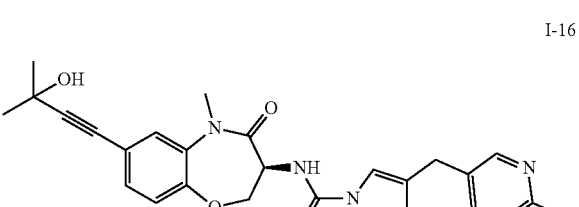
I-17
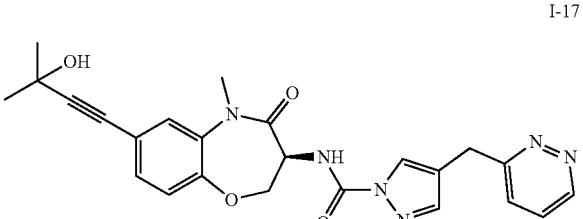
I-18
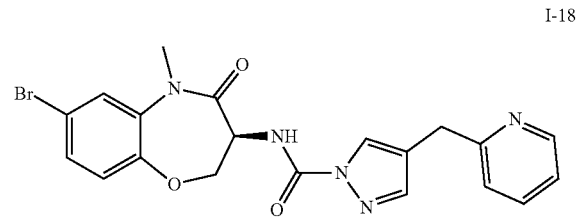
I-19
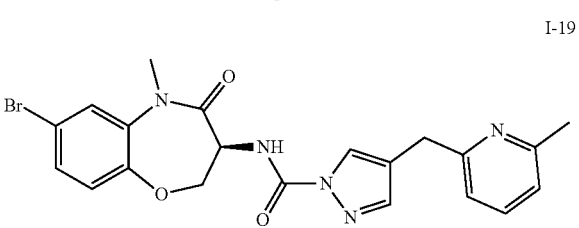

I-20
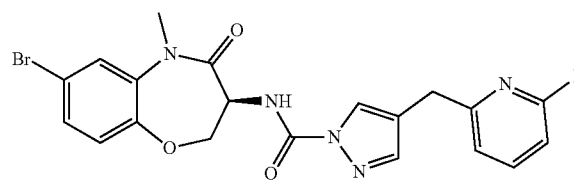
I-27
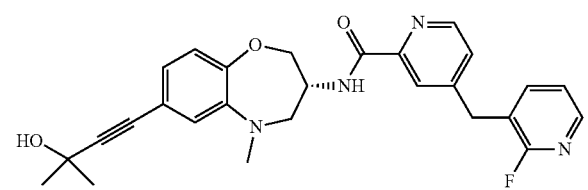
I-21
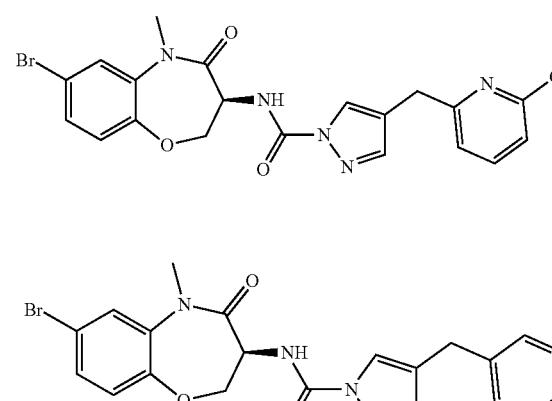
I-28
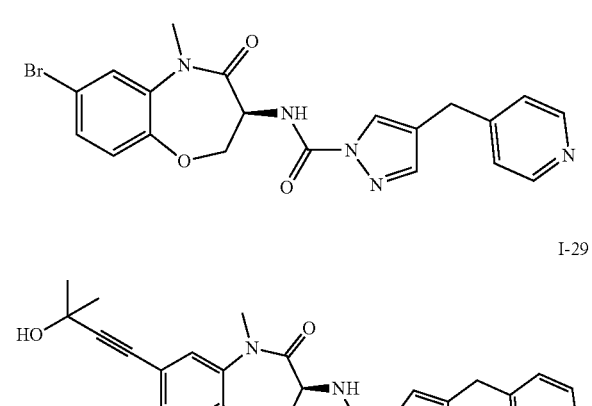
I-22
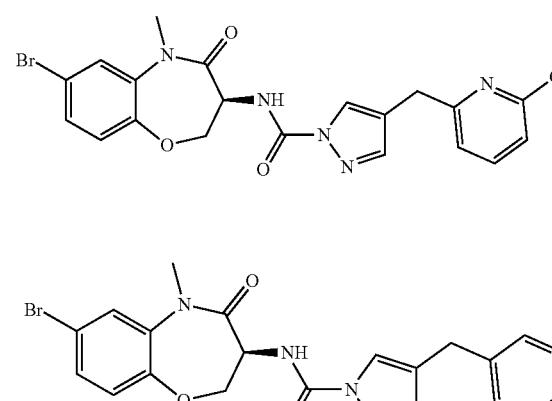
I-29
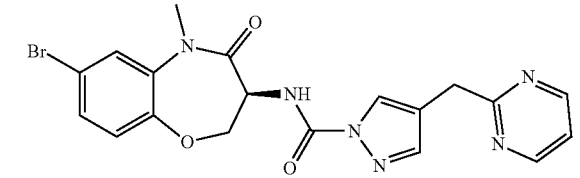
I-23
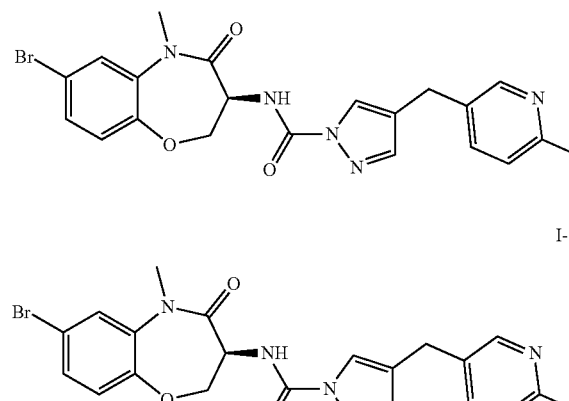
I-30
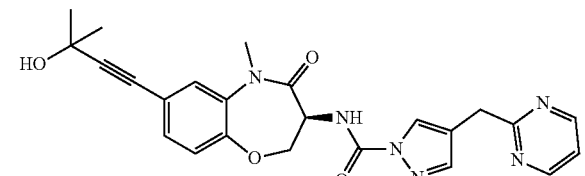
I-24
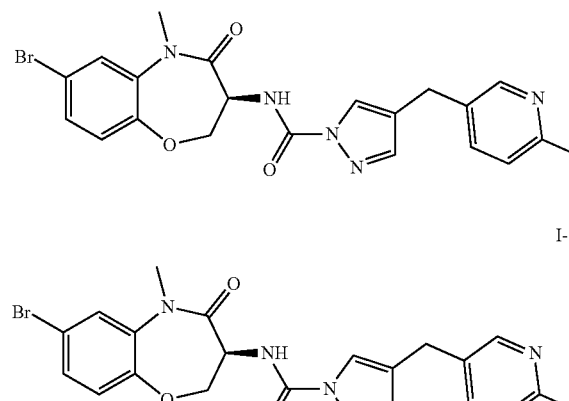
I-31
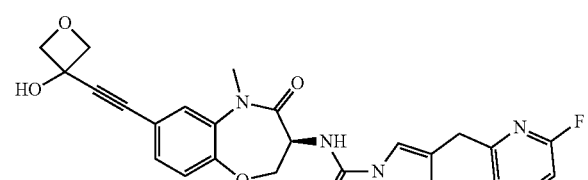
I-25
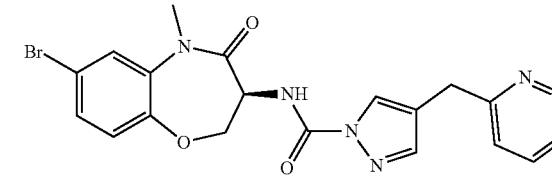
I-32
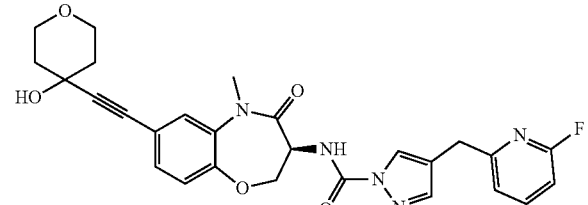
I-26
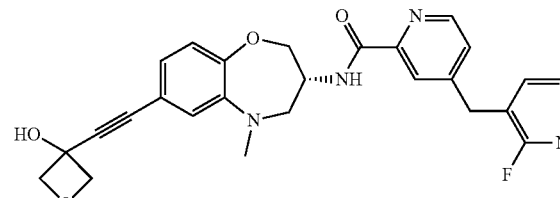
I-33
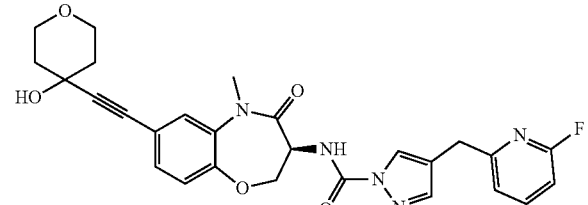

I-34
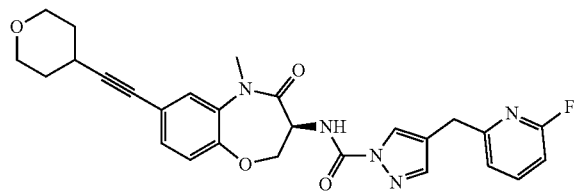
I-35
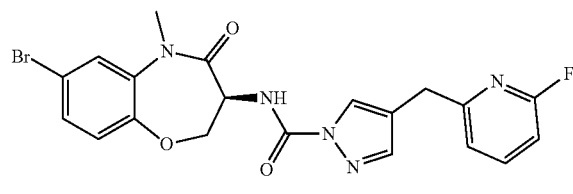
I-36
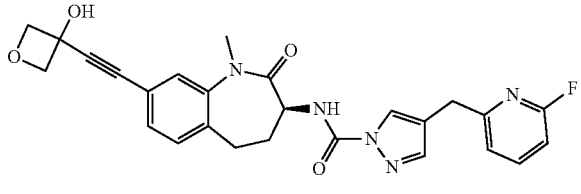
I-37
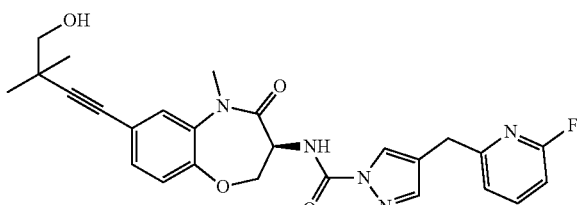
I-38
I-39
I-40
I-41
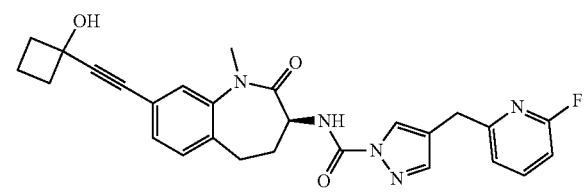
I-42
I-43
I-44
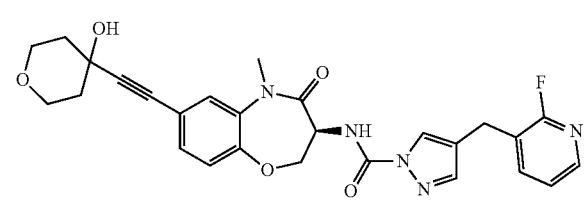
I-45
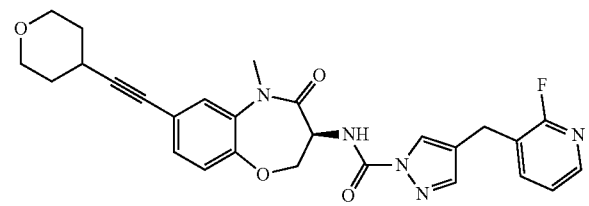
I-46
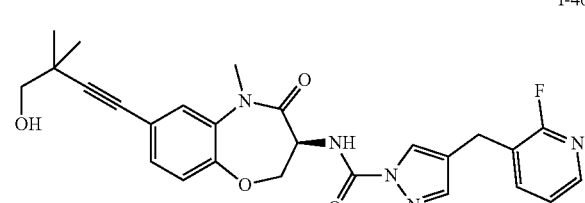
I-47

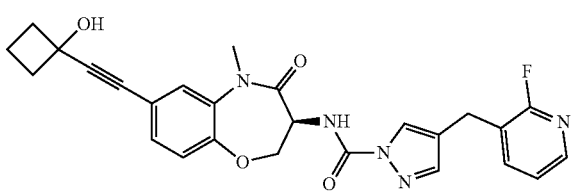

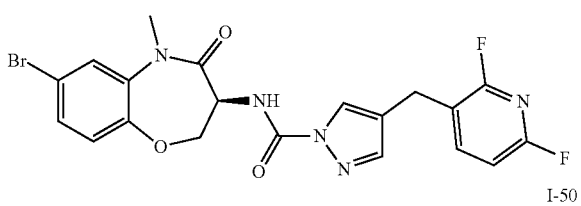

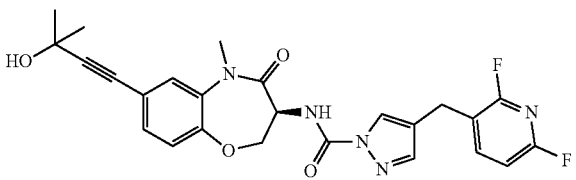

Exemplary compounds within the scope of one or more of Formulas I and I-1 to I-13 include:

I-1: (S)-4-((6-fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide;

I-2: (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)-1H-pyrazole-1-carboxamide;

I-3: (S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-3-yl)oxy)picolinamide;

I-4: (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)oxy)picolinamide;

I-5: (S)-4-((6-fluoropyridin-3-yl)oxy)-N-(7-((3-hydroxyoxetan-3-yl)ethynyl)-5-methyl-4-oxo-2,3,4,5-tetrahydrobenzo[b][1,4]oxazepin-3-yl)picolinamide;

I-6: (S)-4-((6-fluoropyridin-3-yl)oxy)-N-(7-(3-hydroxy-3-methylbut-1-yn-1-yl)-5-methyl-4-oxo-2,3,4,5-tetrahydrobenzo[b][1,4]oxazepin-3-yl)picolinamide;

I-7: (S)-4-((6-fluoropyridin-2-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide;

I-8: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-2-ylmethyl)-1H-pyrazole-1-carboxamide;

I-9: (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide;

I-10: (S)—N-(7-((3-hydroxyoxetan-3-yl)ethynyl)-5-methyl-4-oxo-2,3,4,5-tetrahydrobenzo[b][1,4]oxazepin-3-yl)-4-((6-hydroxypyridin-2-yl)methyl)picolinamide;

I-11: (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)picolinamide;

I-12: (S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-2-yl)methyl)picolinamide;

I-13: (S)-4-((6-fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide;

I-14: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-3-ylmethyl)-1H-pyrazole-1-carboxamide;

I-15: (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)methyl)-1H-pyrazole-1-carboxamide;

I-16: (S)-4-((6-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide;

I-17: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridazin-3-ylmethyl)-1H-pyrazole-1-carboxamide;

I-18: (S)—N-(7-bromo-5-methyl-4-oxo-2,3,4,5-tetrahydrobenzo[b][1,4]oxazepin-3-yl)-4-(pyridin-2-ylmethyl)-1H-pyrazole-1-carboxamide;

I-19: (S)—N-(7-bromo-5-methyl-4-oxo-2,3,4,5-tetrahydrobenzo[b][1,4]oxazepin-3-yl)-4-((6-methylpyridin-2-yl)methyl)-1H-pyrazole-1-carboxamide;

I-20: (S)—N-(7-bromo-5-methyl-4-oxo-2,3,4,5-tetrahydrobenzo[b][1,4]oxazepin-3-yl)-4-((6-fluoropyridin-2-yl)methyl)-1H-pyrazole-1-carboxamide;

I-21: (S)—N-(7-bromo-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide;

I-22: (S)—N-(7-bromo-5-methyl-4-oxo-2,3,4,5-tetrahydrobenzo[b][1,4]oxazepin-3-yl)-4-(pyridin-3-ylmethyl)-1H-pyrazole-1-carboxamide;

I-23: (S)—N-(7-bromo-5-methyl-4-oxo-2,3,4,5-tetrahydrobenzo[b][1,4]oxazepin-3-yl)-4-((6-methylpyridin-3-yl)methyl)-1H-pyrazole-1-carboxamide;

I-24: (S)—N-(7-bromo-5-methyl-4-oxo-2,3,4,5-tetrahydrobenzo[b][1,4]oxazepin-3-yl)-4-((6-fluoropyridin-3-yl)methyl)-1H-pyrazole-1-carboxamide;

I-25: (S)—N-(7-bromo-5-methyl-4-oxo-2,3,4,5-tetrahydrobenzo[b][1,4]oxazepin-3-yl)-4-(pyridazin-3-ylmethyl)-1H-pyrazole-1-carboxamide;

I-26: (S)-4-((2-fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide;

I-27: (S)-4-((2-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide;

I-28: (S)—N-(7-bromo-5-methyl-4-oxo-2,3,4,5-tetrahydrobenzo[b][1,4]oxazepin-3-yl)-4-(pyridin-4-ylmethyl)-1H-pyrazole-1-carboxamide;

I-29: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-4-ylmethyl)-1H-pyrazole-1-carboxamide;

I-30: (S)—N-(7-bromo-5-methyl-4-oxo-2,3,4,5-tetrahydrobenzo[b][1,4]oxazepin-3-yl)-4-(pyrimidin-2-ylmethyl)-1H-pyrazole-1-carboxamide;

I-31: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyrimidin-2-ylmethyl)-1H-pyrazole-1-carboxamide;

I-32: (S)-4-((6-fluoropyridin-2-yl)methyl)-N-(7-((3-hydroxyoxetan-3-yl)ethynyl)-5-methyl-4-oxo-2,3,4,5-tetrahydrobenzo[b][1,4]oxazepin-3-yl)-1H-pyrazole-1-carboxamide;

I-33: (S)-4-((6-fluoropyridin-2-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide;

I-34: (S)-4-((6-fluoropyridin-2-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide;

I-35: (S)—N-(8-bromo-1-methyl-2-oxo-2,3,4,5-tetrahydro-1H-benzo[b]azepin-3-yl)-4-((6-fluoropyridin-2-yl)methyl)-1H-pyrazole-1-carboxamide;

I-36: (S)-4-((6-fluoropyridin-2-yl)methyl)-N-(8-((3-hydroxyoxetan-3-yl)ethynyl)-1-methyl-2-oxo-2,3,4,5-tetrahydro-1H-benzo[b]azepin-3-yl)-1H-pyrazole-1-carboxamide;

I-37: (S)-4-((6-fluoropyridin-2-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide;

I-38: (S)-4-((6-fluoropyridin-2-yl)methyl)-N-(8-(3-hydroxy-3-methylbut-1-yn-1-yl)-1-methyl-2-oxo-2,3,4,5-tetrahydro-1H-benzo[b]azepin-3-yl)-1H-pyrazole-1-carboxamide;

I-39: (S)-4-((6-fluoropyridin-2-yl)methyl)-N-(8-(4-hydroxy-3,3-dimethylbut-1-yn-1-yl)-1-methyl-2-oxo-2,3,4,5-tetrahydro-1H-benzo[b]azepin-3-yl)-1H-pyrazole-1-carboxamide;

I-40: (S)-4-((6-fluoropyridin-2-yl)methyl)-N-(8-((4-hydroxytetrahydro-2H-pyran-4-yl)ethynyl)-1-methyl-2-oxo-2,3,4,5-tetrahydro-1H-benzo[b]azepin-3-yl)-1H-pyrazole-1-carboxamide;

I-41: (S)-4-((6-fluoropyridin-2-yl)methyl)-N-(8-((1-hydroxycyclobutyl)ethynyl)-1-methyl-2-oxo-2,3,4,5-tetrahydro-1H-benzo[b]azepin-3-yl)-1H-pyrazole-1-carboxamide;

I-42: (S)—N-(7-bromo-5-methyl-4-oxo-2,3,4,5-tetrahydrobenzo[b][1,4]oxazepin-3-yl)-4-((2-fluoropyridin-3-yl)methyl)-1H-pyrazole-1-carboxamide;

I-43: (S)-4-((2-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide;

I-44: (S)-4-((2-fluoropyridin-3-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide;

I-45: (S)-4-((2-fluoropyridin-3-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide;

I-46: (S)-4-((2-fluoropyridin-3-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide;

I-47: (S)-4-((2-fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)-1H-pyrazole-1-carboxamide;

I-48: (S)-4-((2-fluoropyridin-3-yl)methyl)-N-(7-((1-hydroxycyclobutyl)ethynyl)-5-methyl-4-oxo-2,3,4,5-tetrahydrobenzo[b][1,4]oxazepin-3-yl)-1H-pyrazole-1-carboxamide;

I-49: (S)—N-(7-bromo-5-methyl-4-oxo-2,3,4,5-tetrahydrobenzo[b][1,4]oxazepin-3-yl)-4-((2,6-difluoropyridin-3-yl)methyl)-1H-pyrazole-1-carboxamide; or I-50: (S)-4-((2,6-difluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide.

Additional exemplary compounds within the scope of one or more of Formulas I and I-1 to I-13 include:

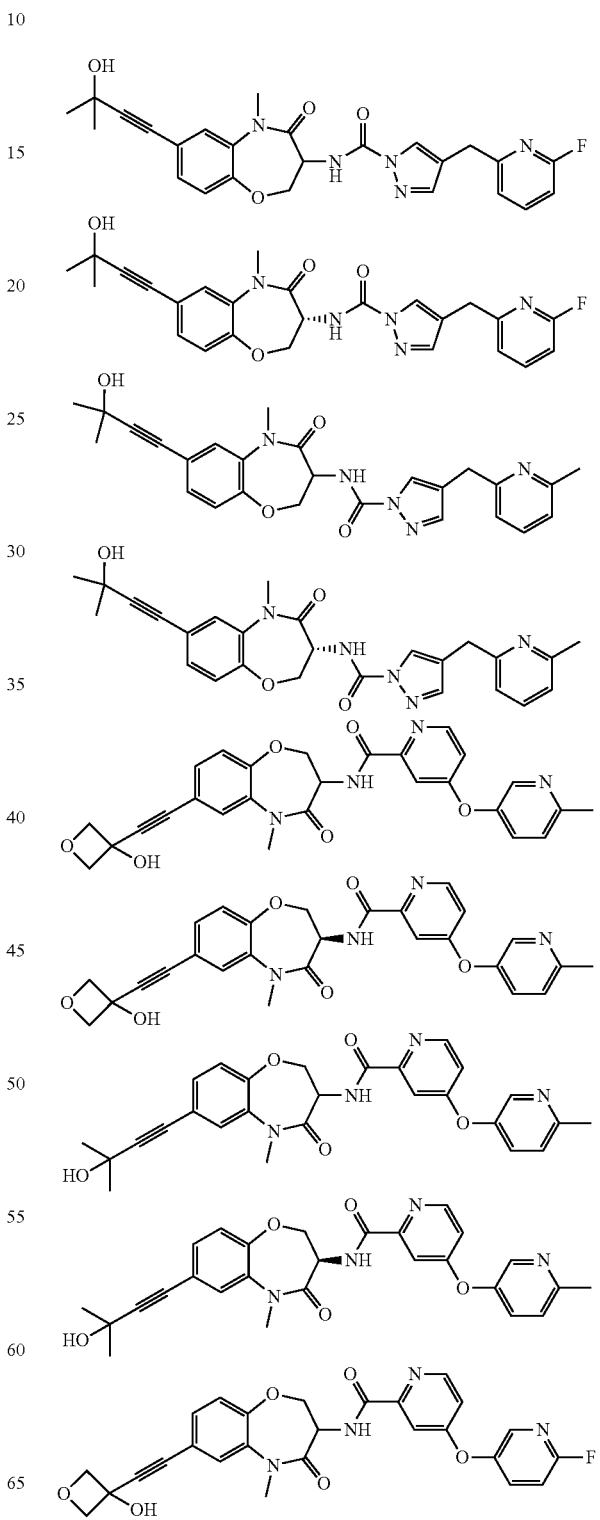

-continued
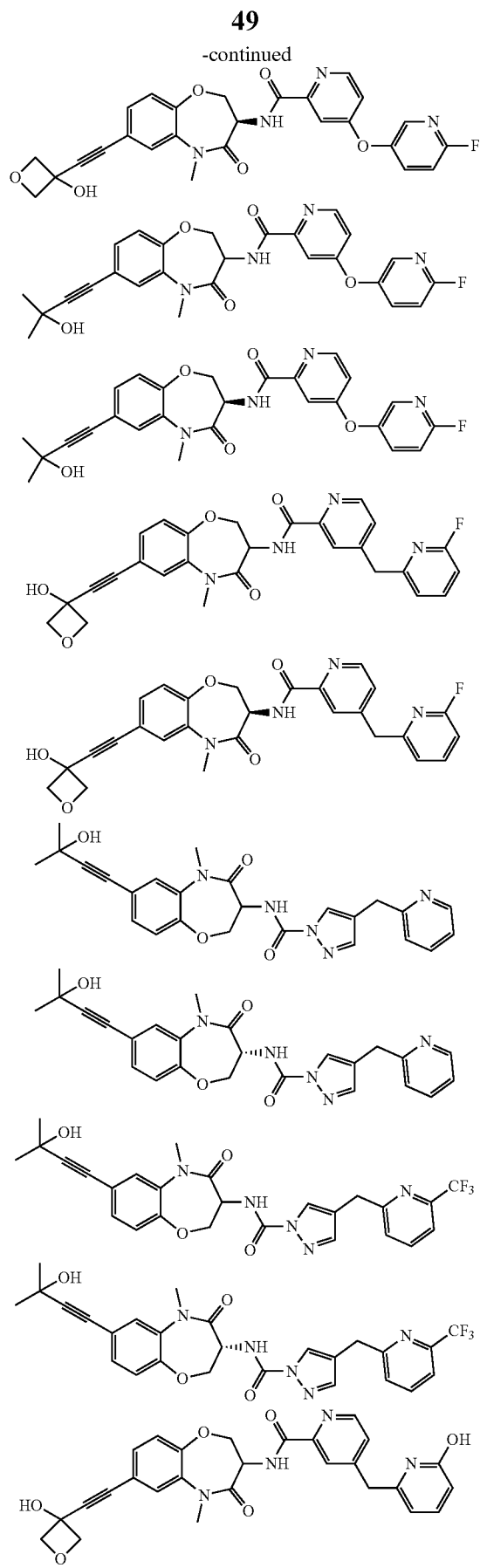
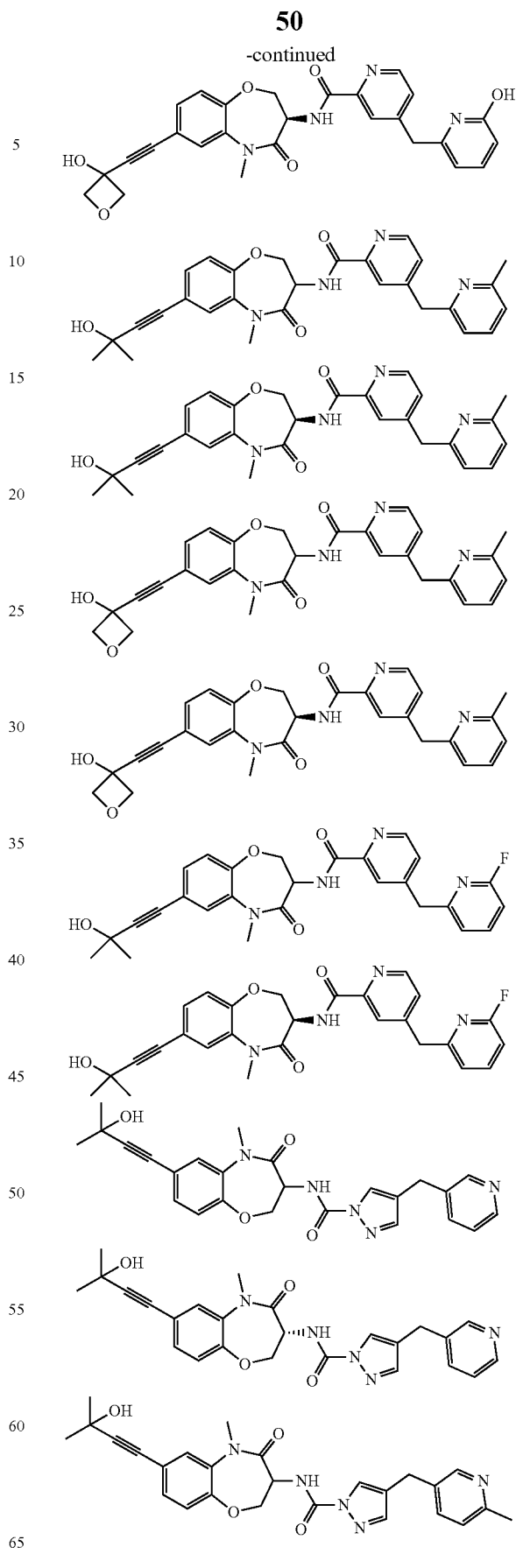

51
-continued
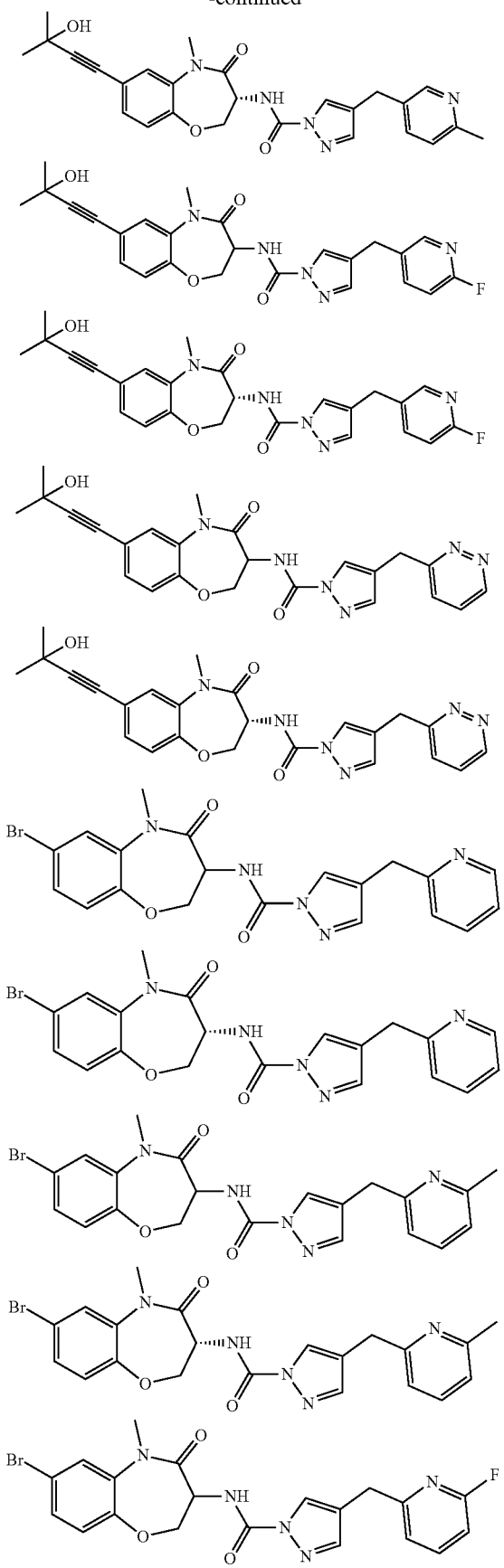
52
-continued
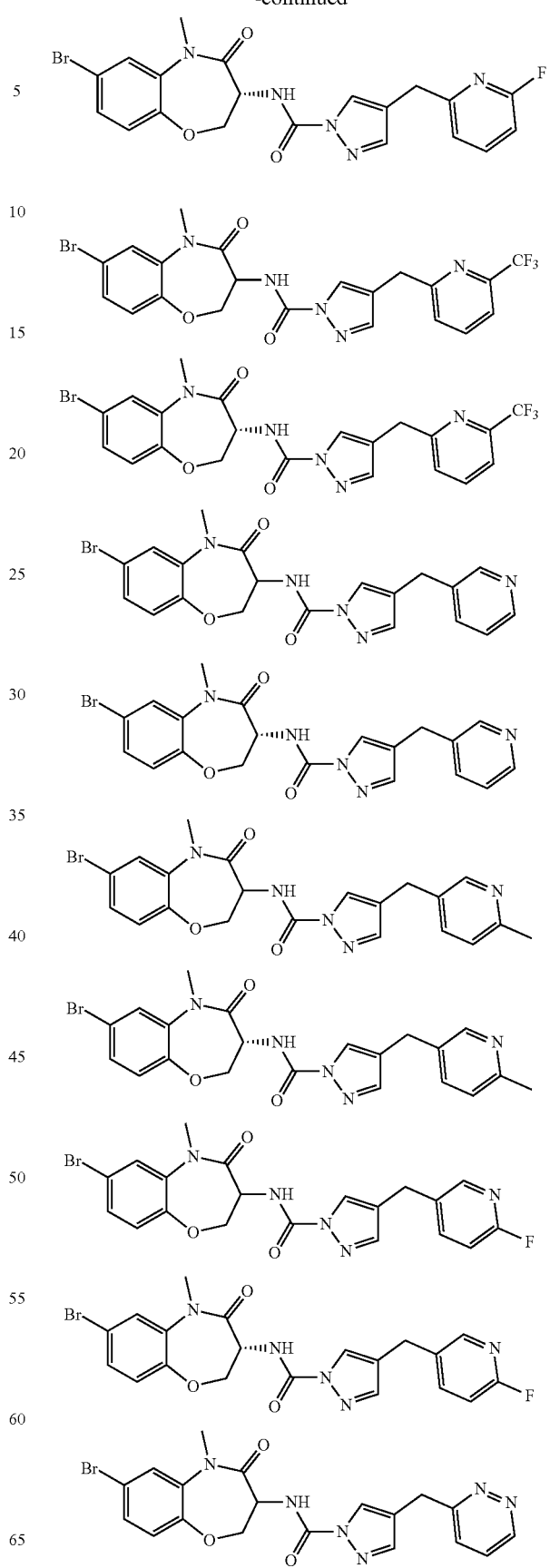

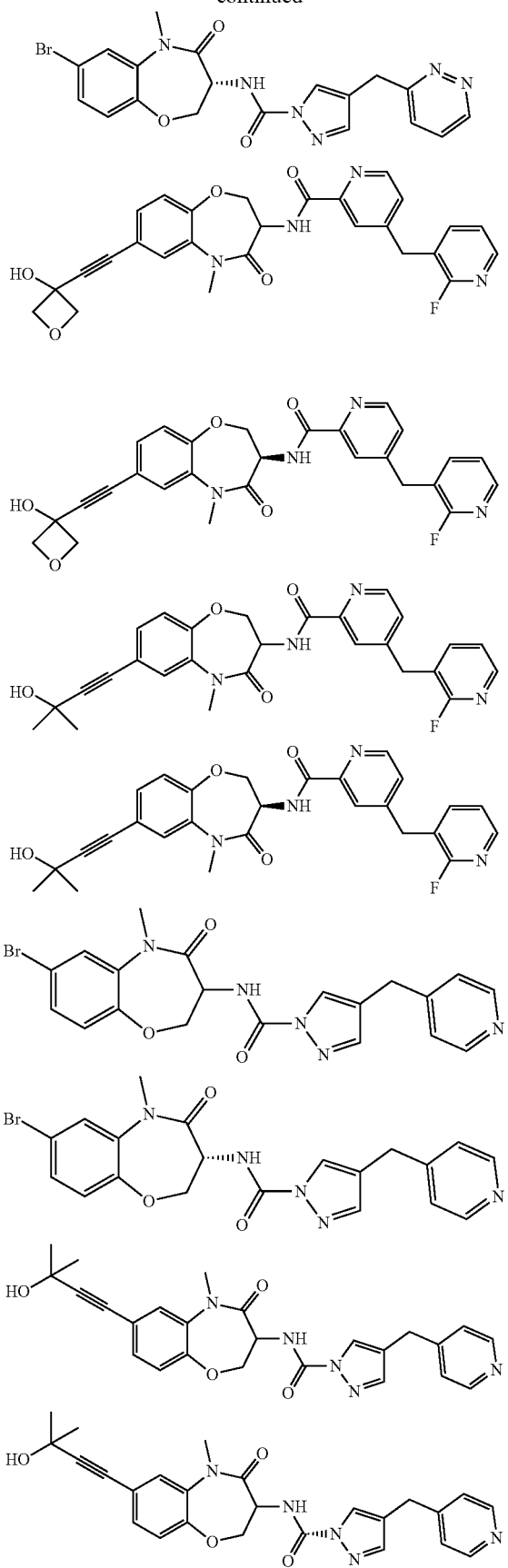
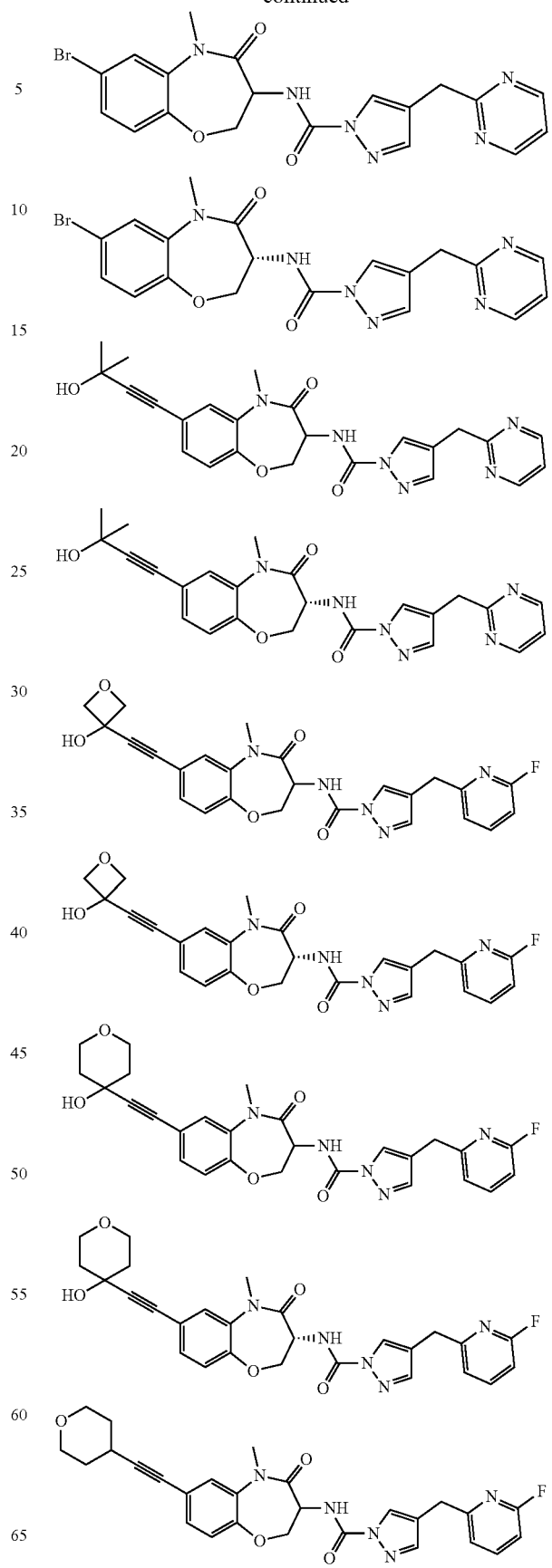

55
-continued
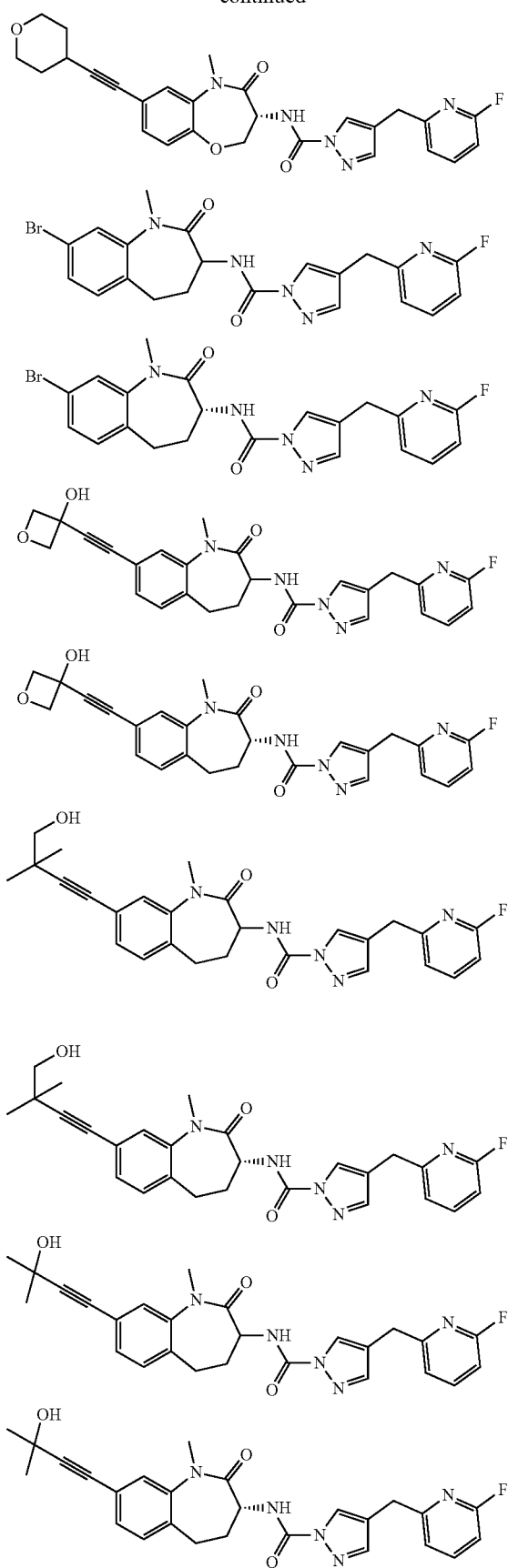
56
-continued
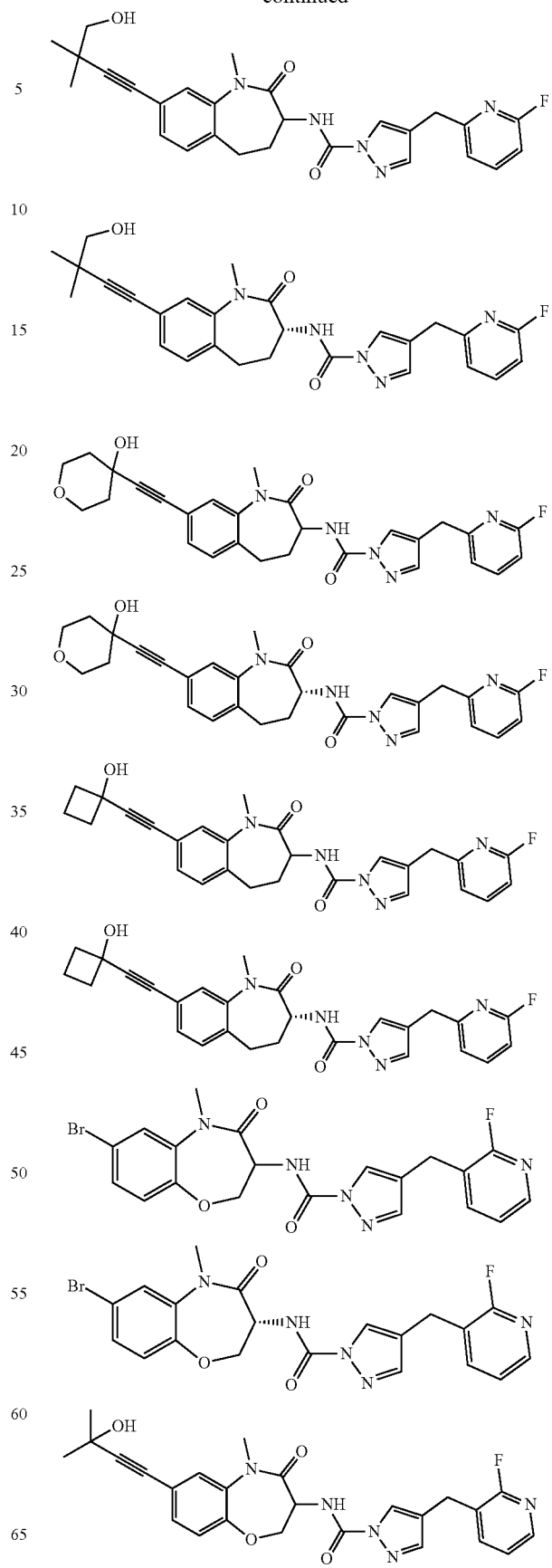

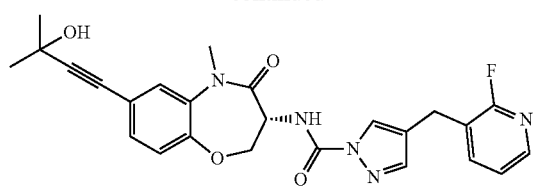
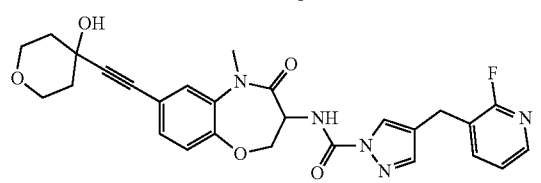
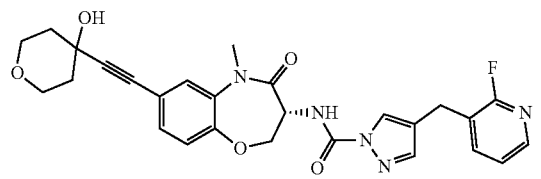
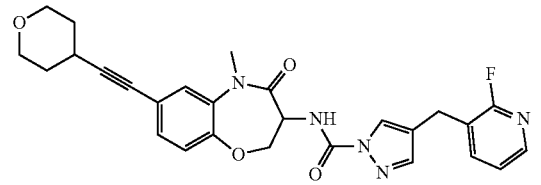
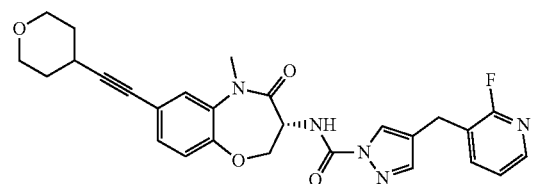
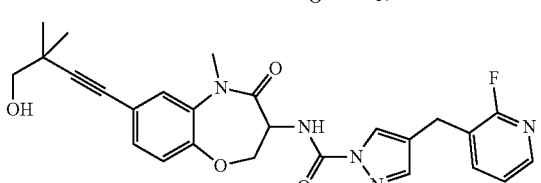
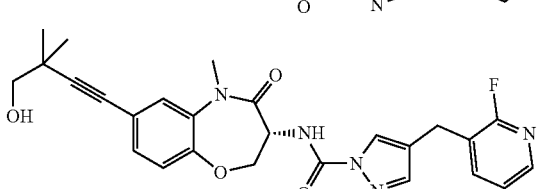
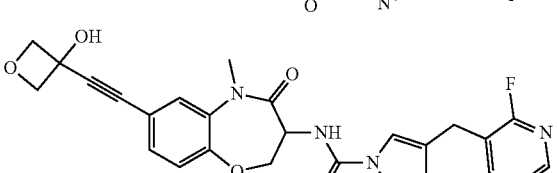
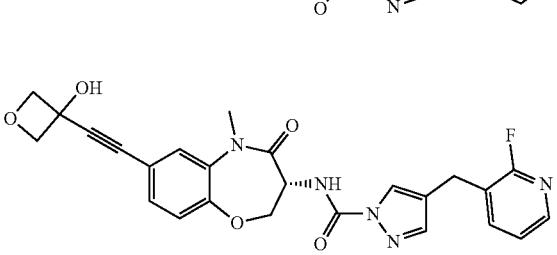
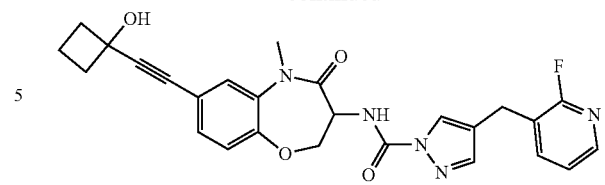
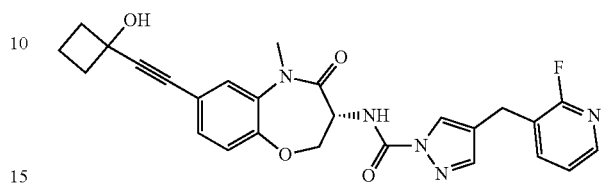
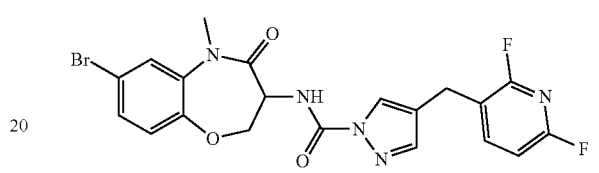
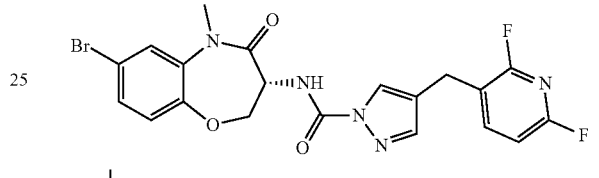
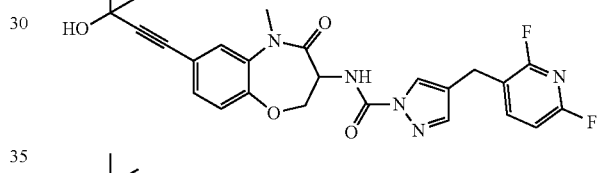
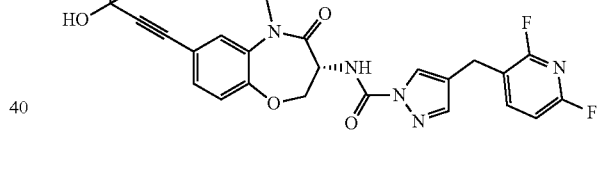
Further exemplary compounds within the scope of one or more of Formulas I and I-1 to I-13 include:
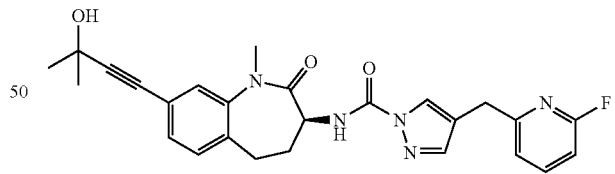
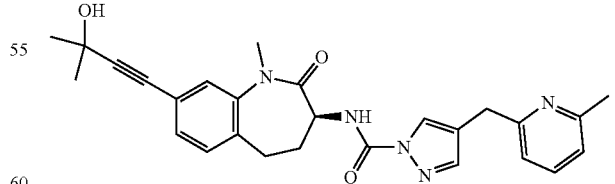
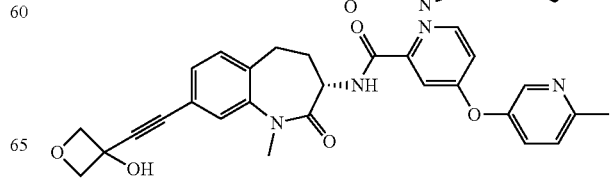

59
-continued
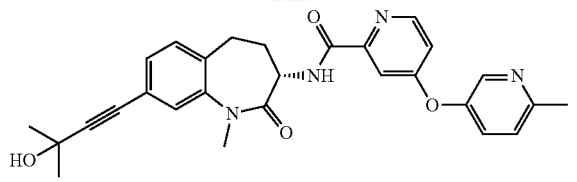
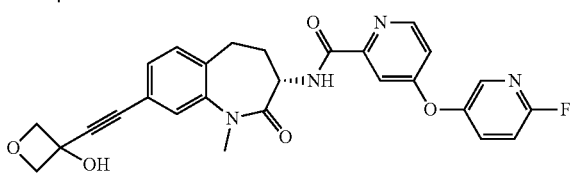
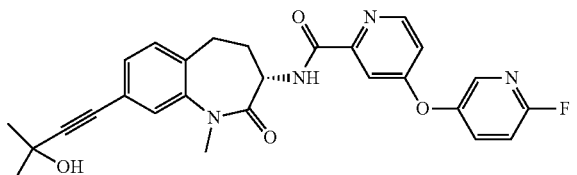
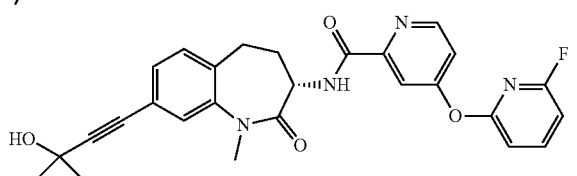
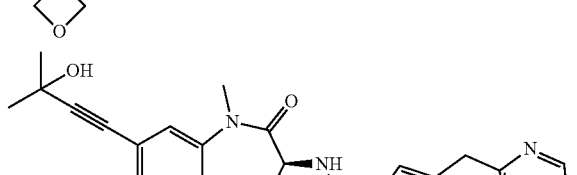
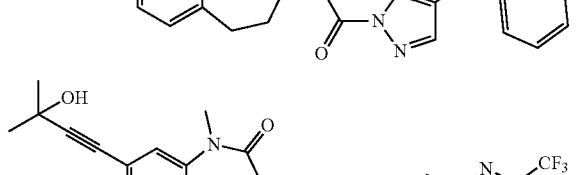
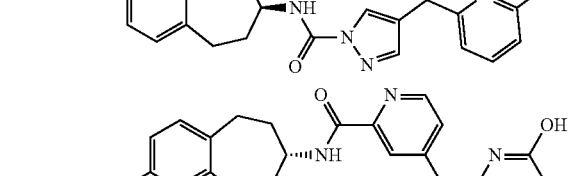
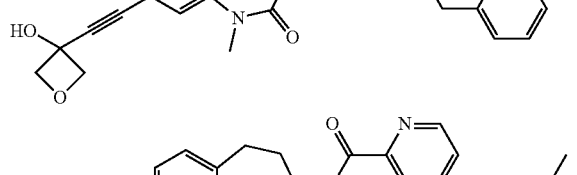
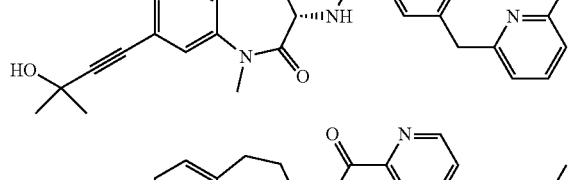
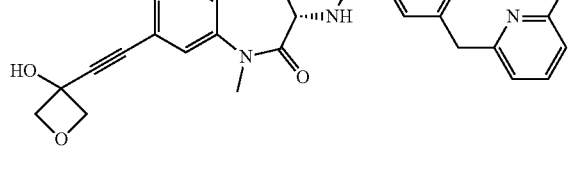
60
-continued
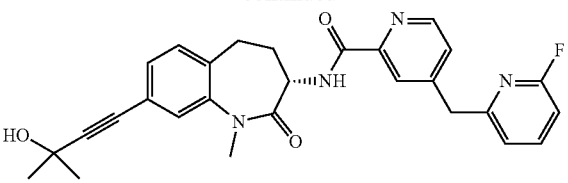
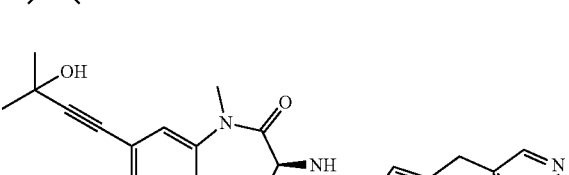
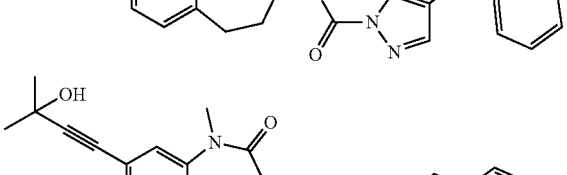
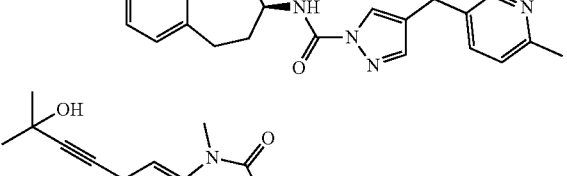
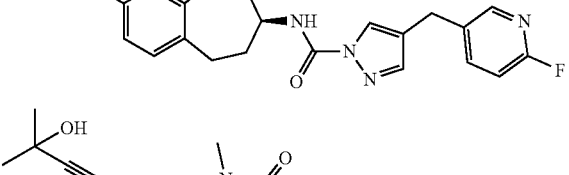
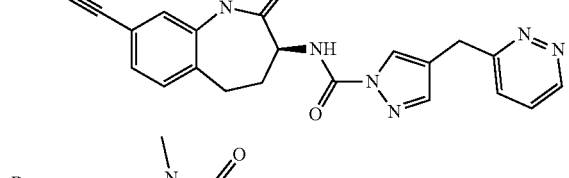
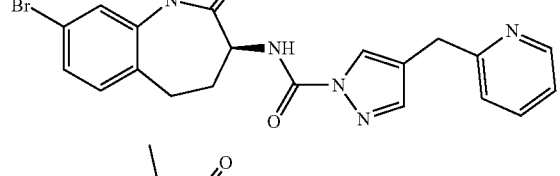
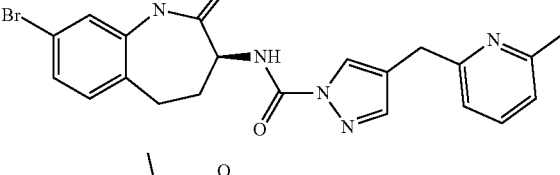
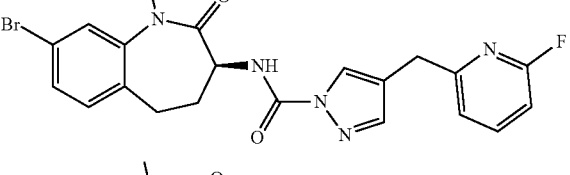
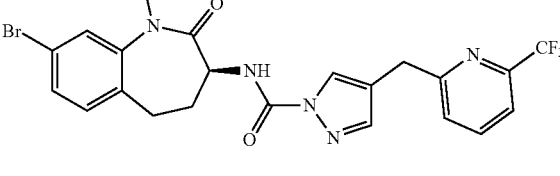

61
-continued
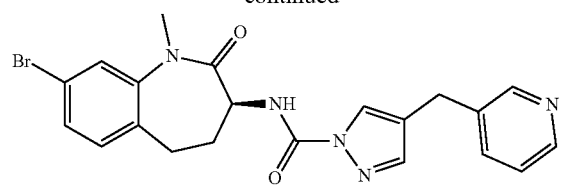
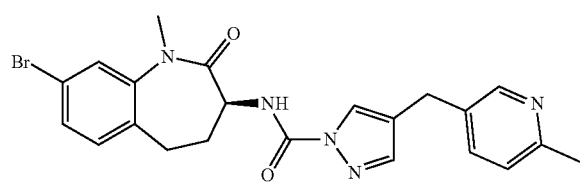
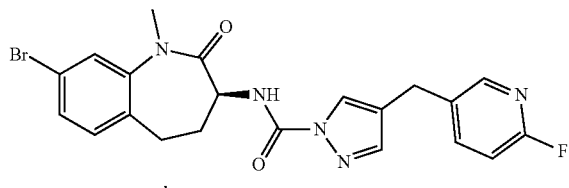
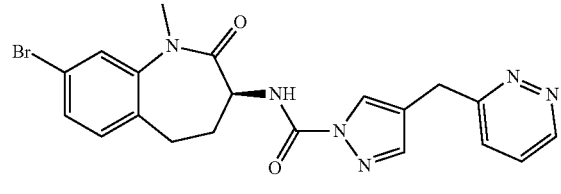
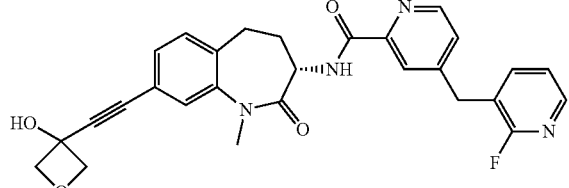
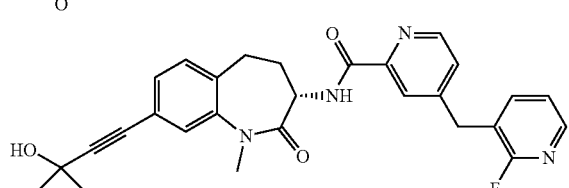
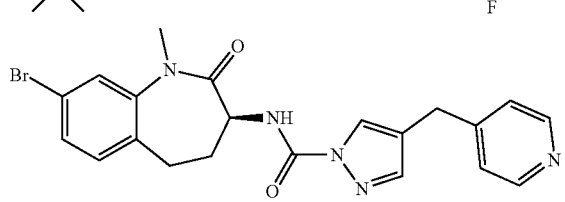
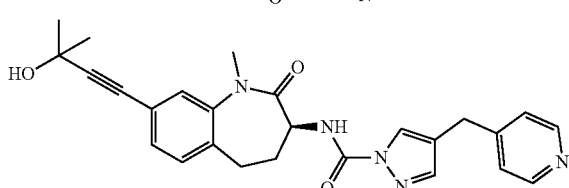
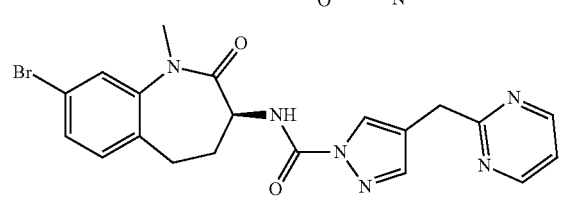
62
-continued
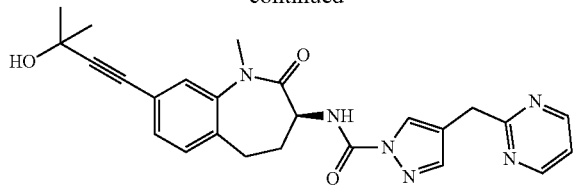
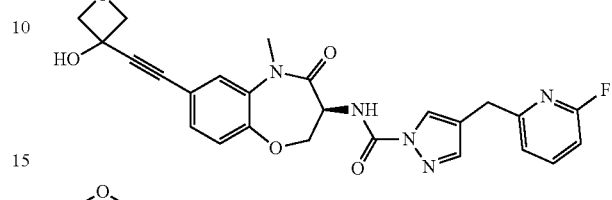
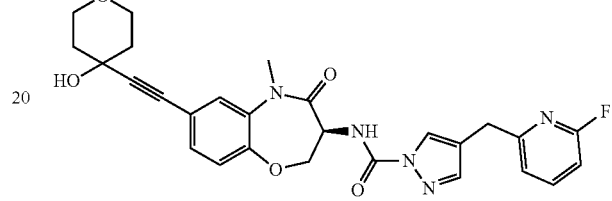
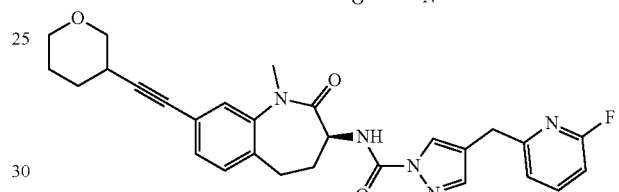
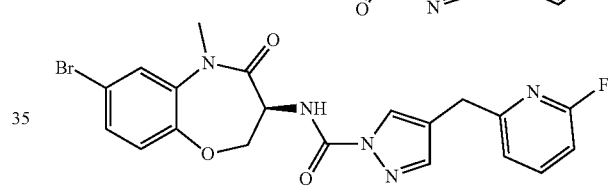
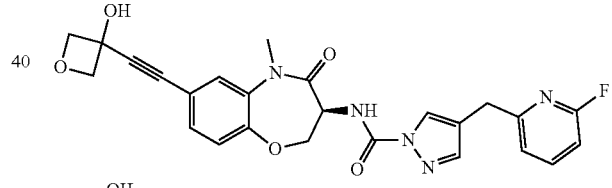
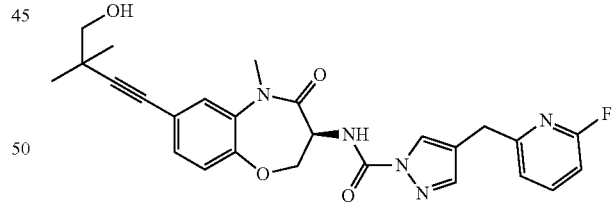
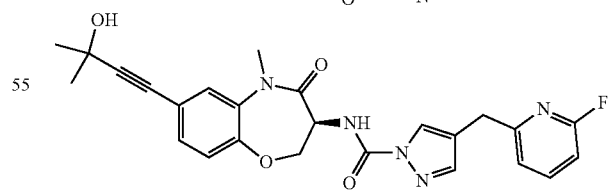
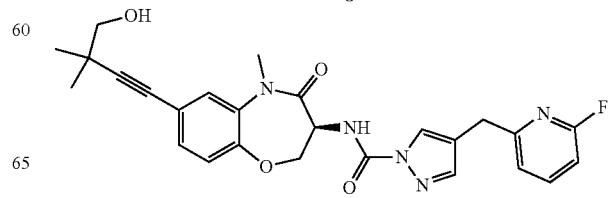

63
-continued
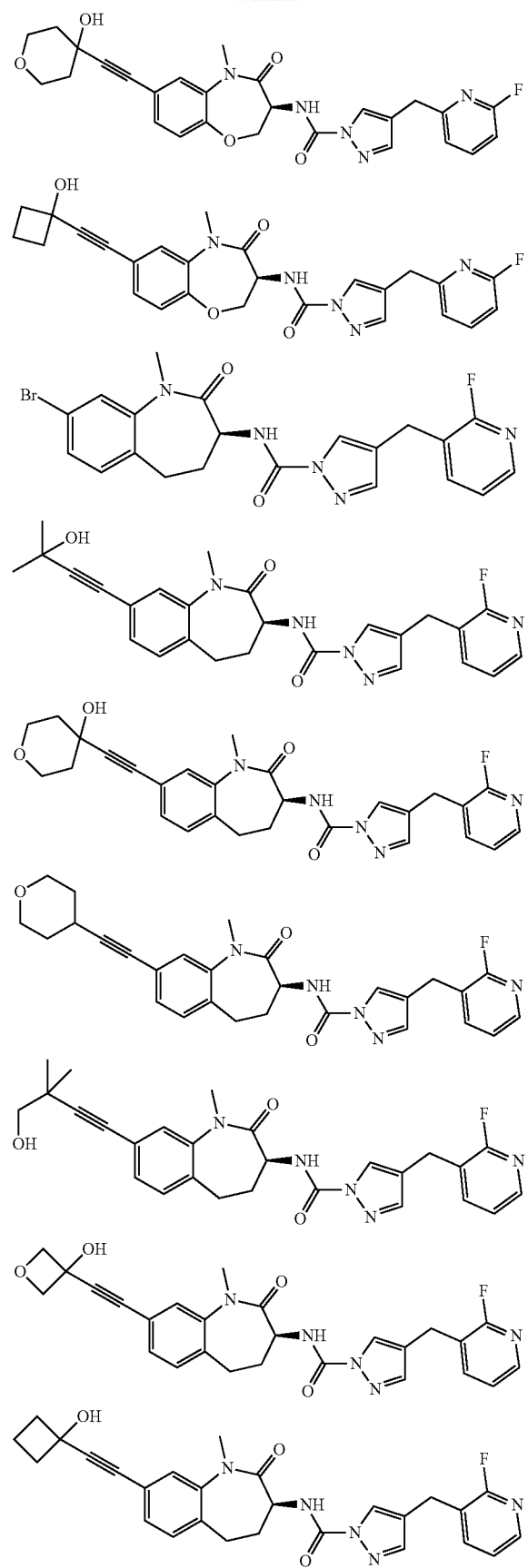
64
-continued
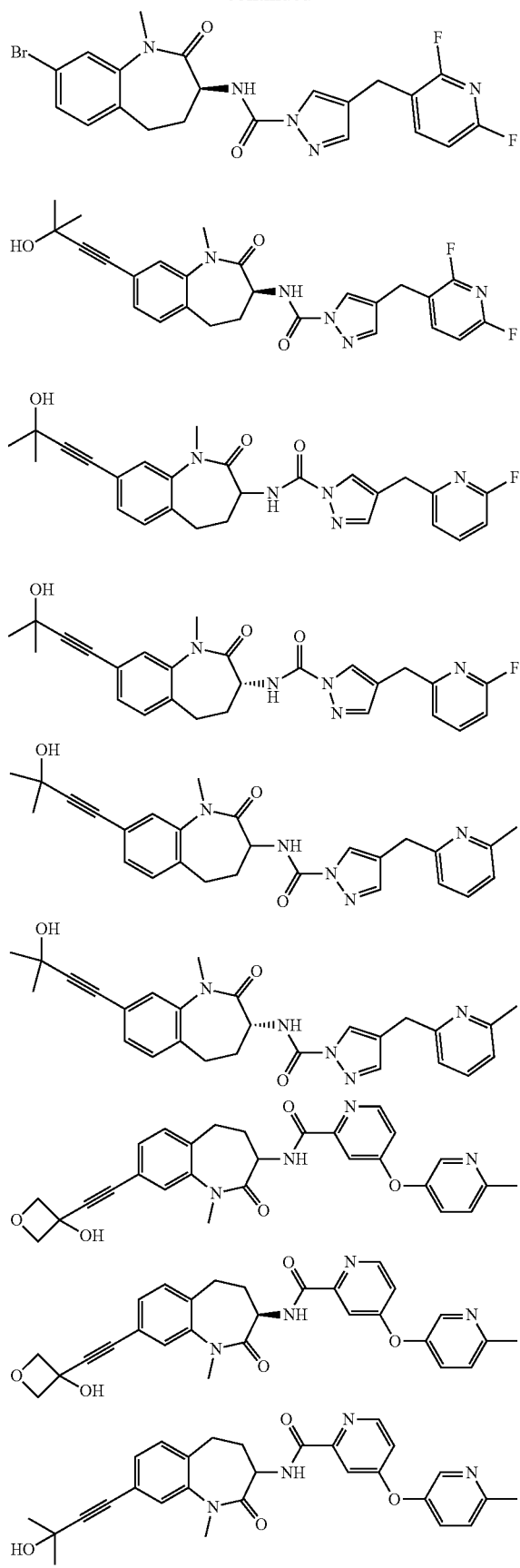

-continued
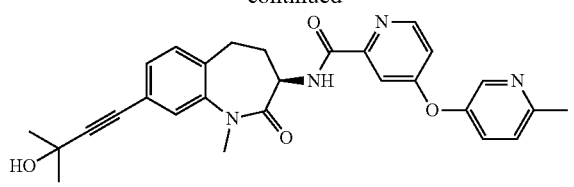
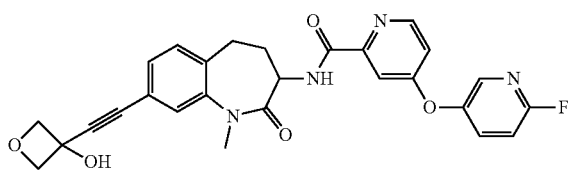
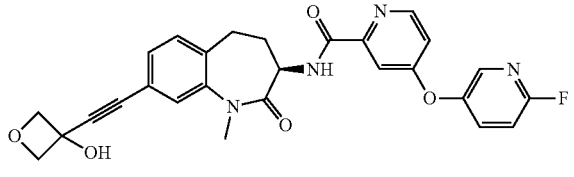
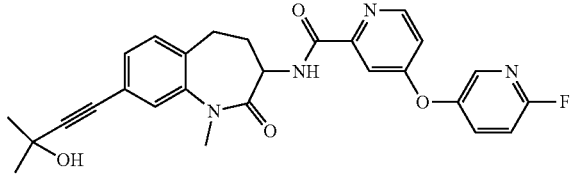
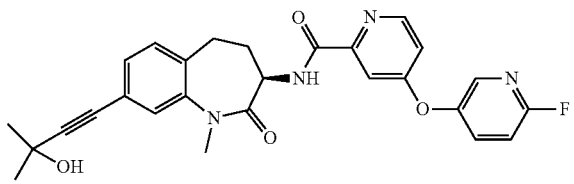
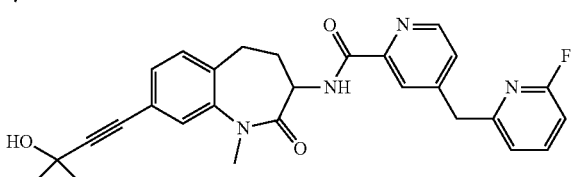
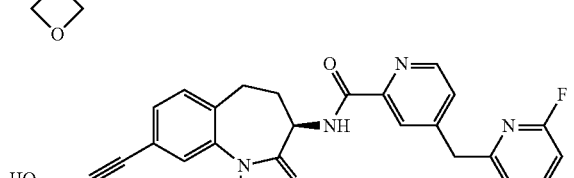
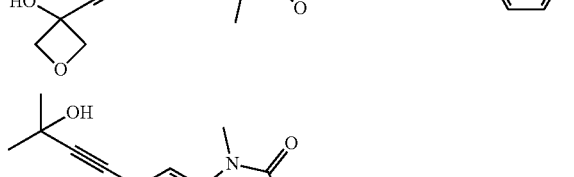
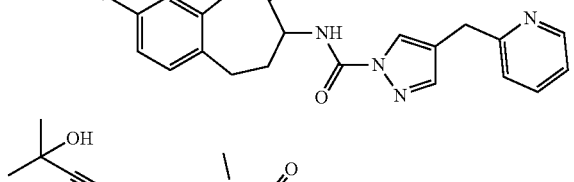
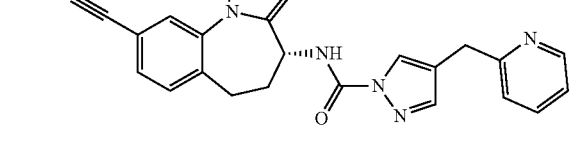
-continued
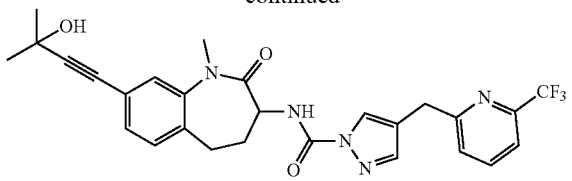
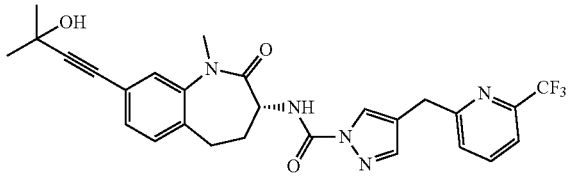
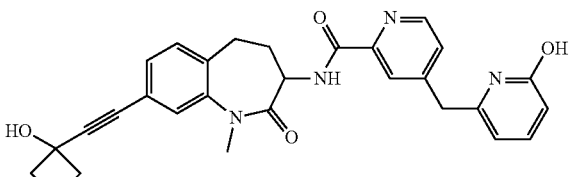
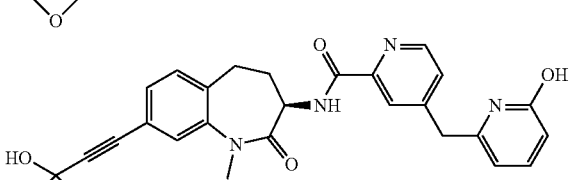
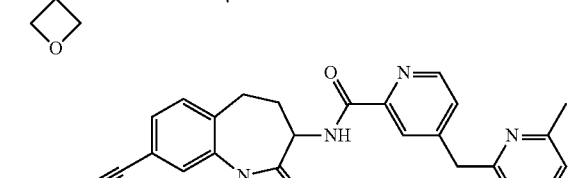
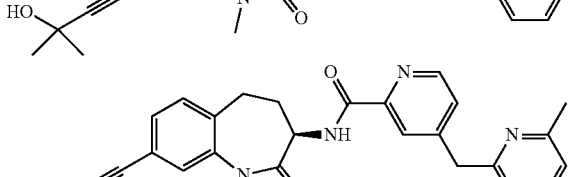
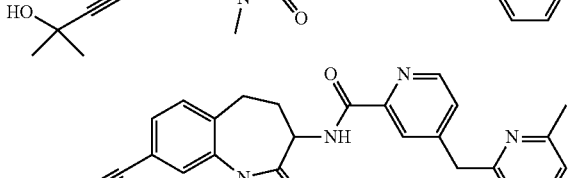
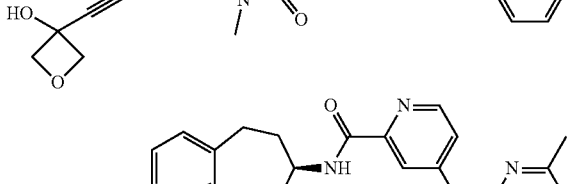
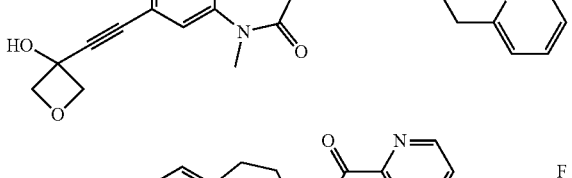
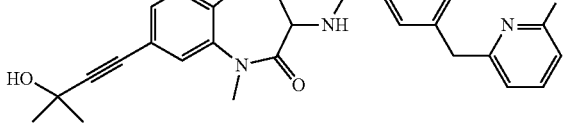

-continued
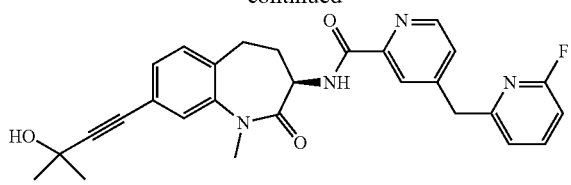
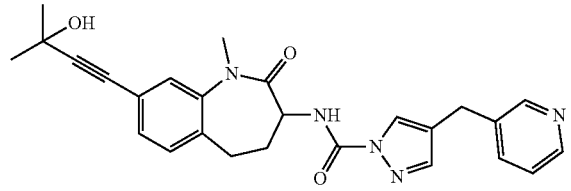
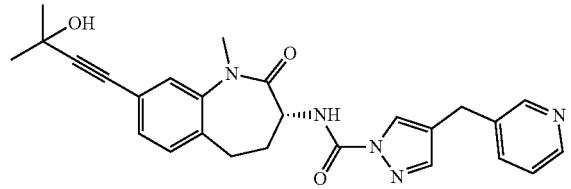
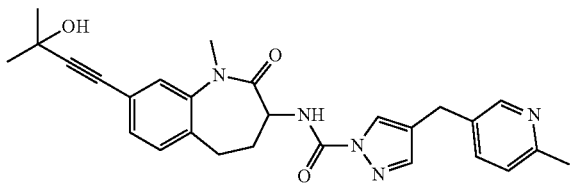
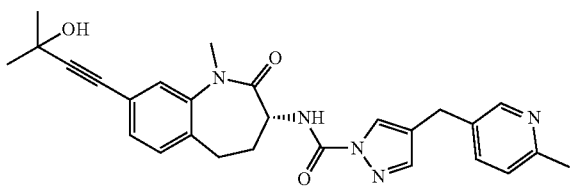
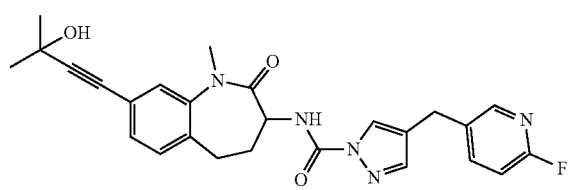
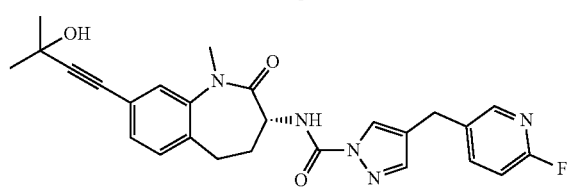
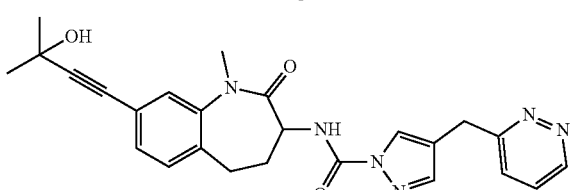
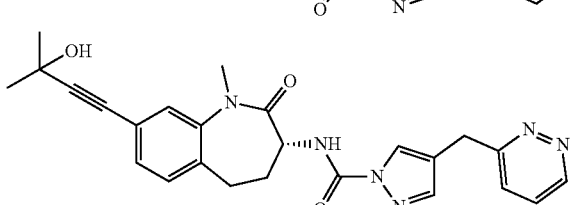
-continued
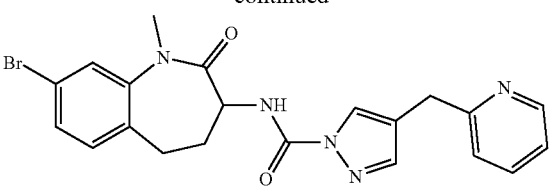
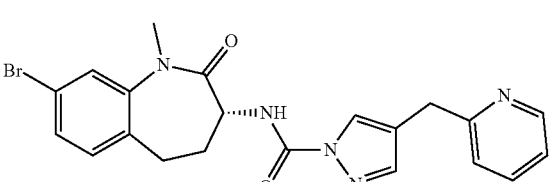
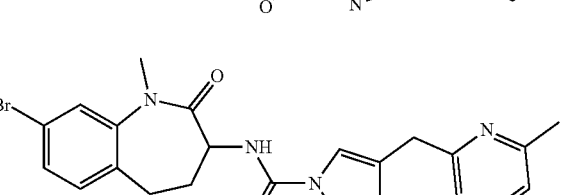
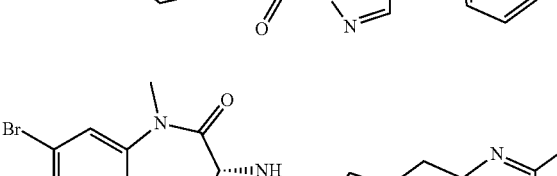
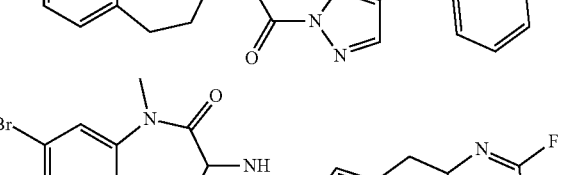
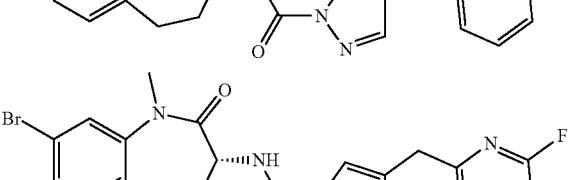
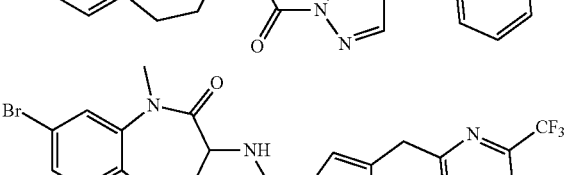
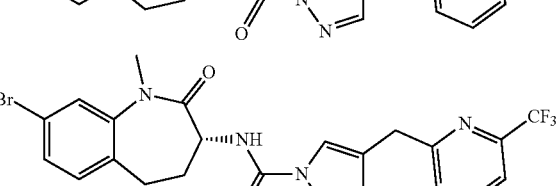
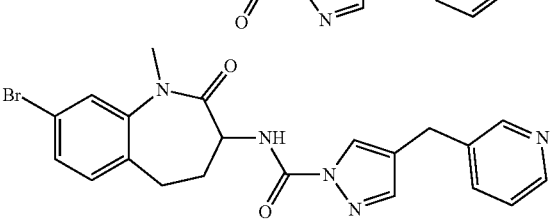

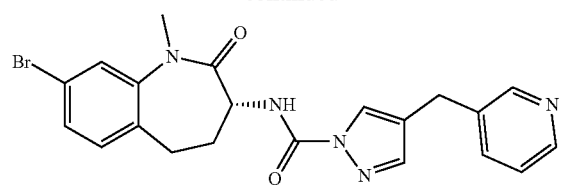
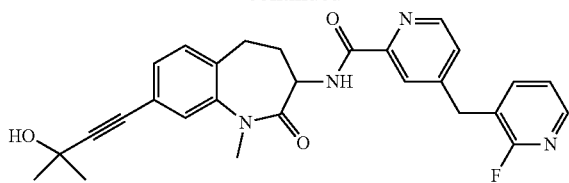
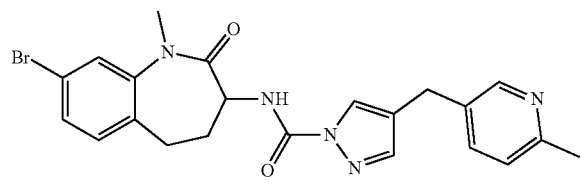
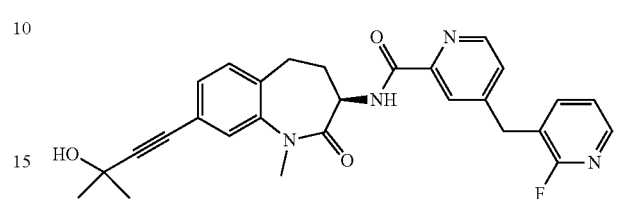
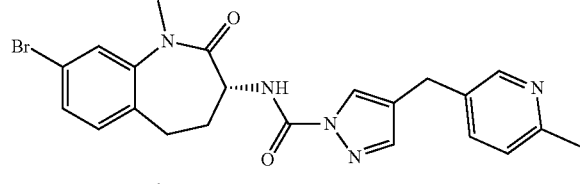
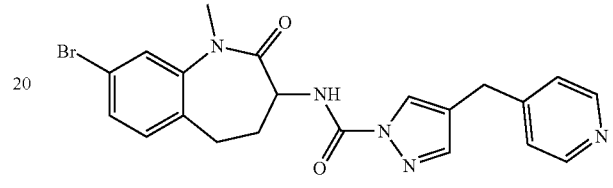
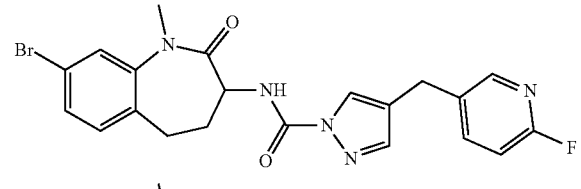
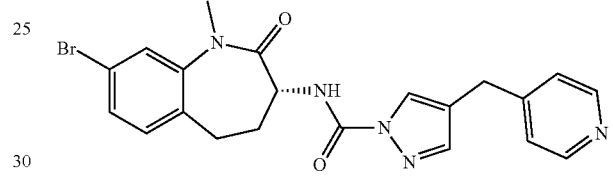
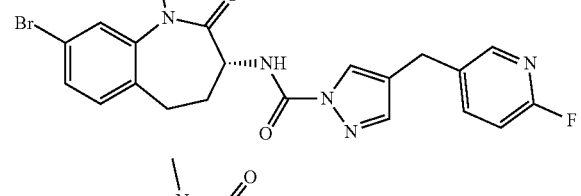
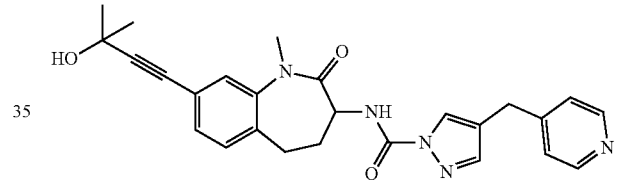
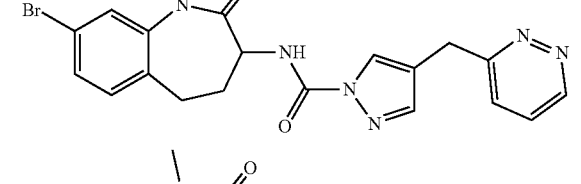
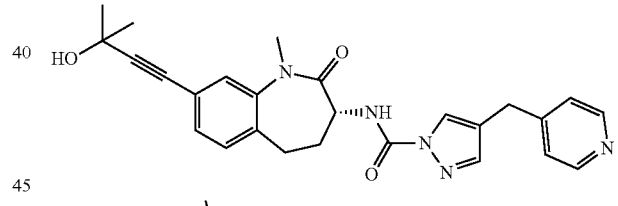
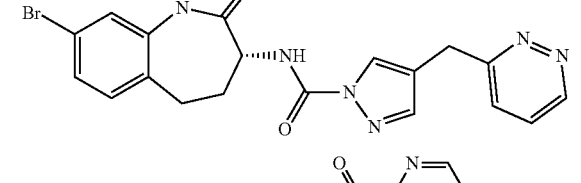
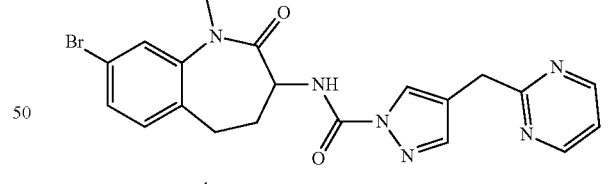
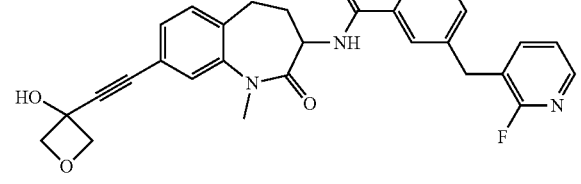
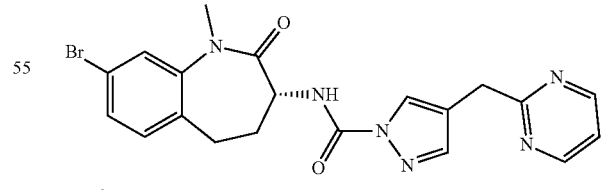
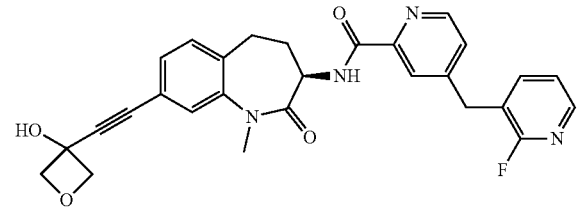
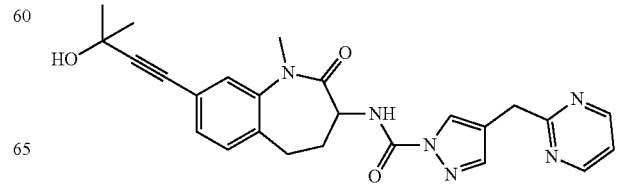

-continued
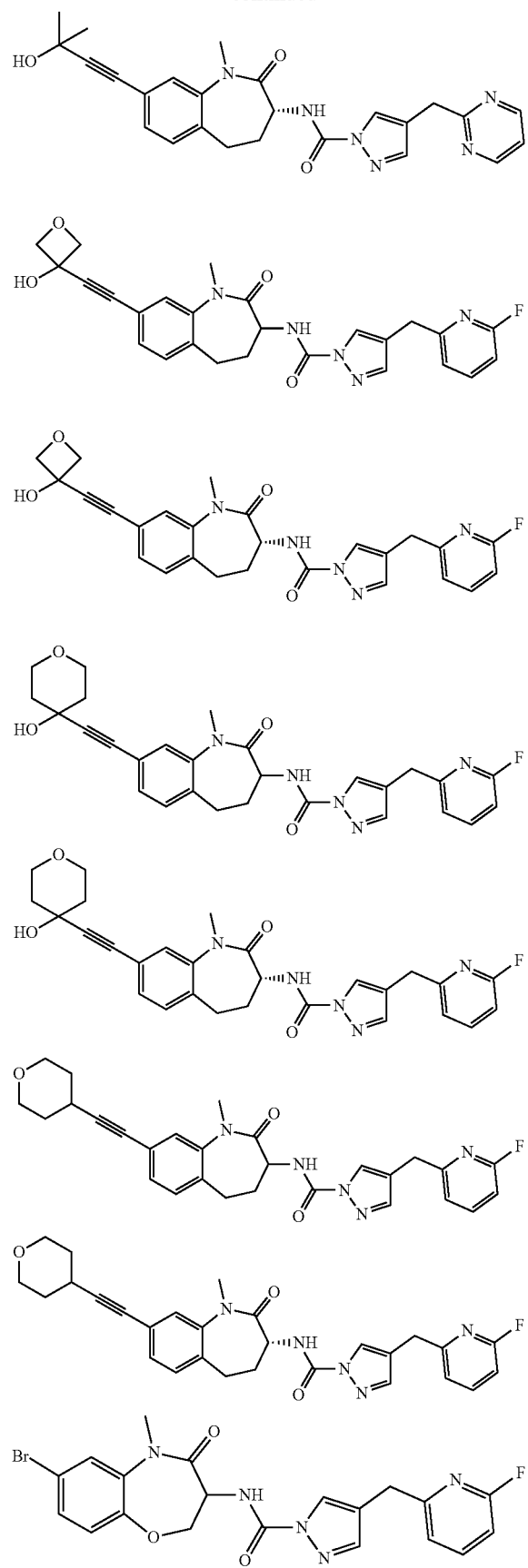
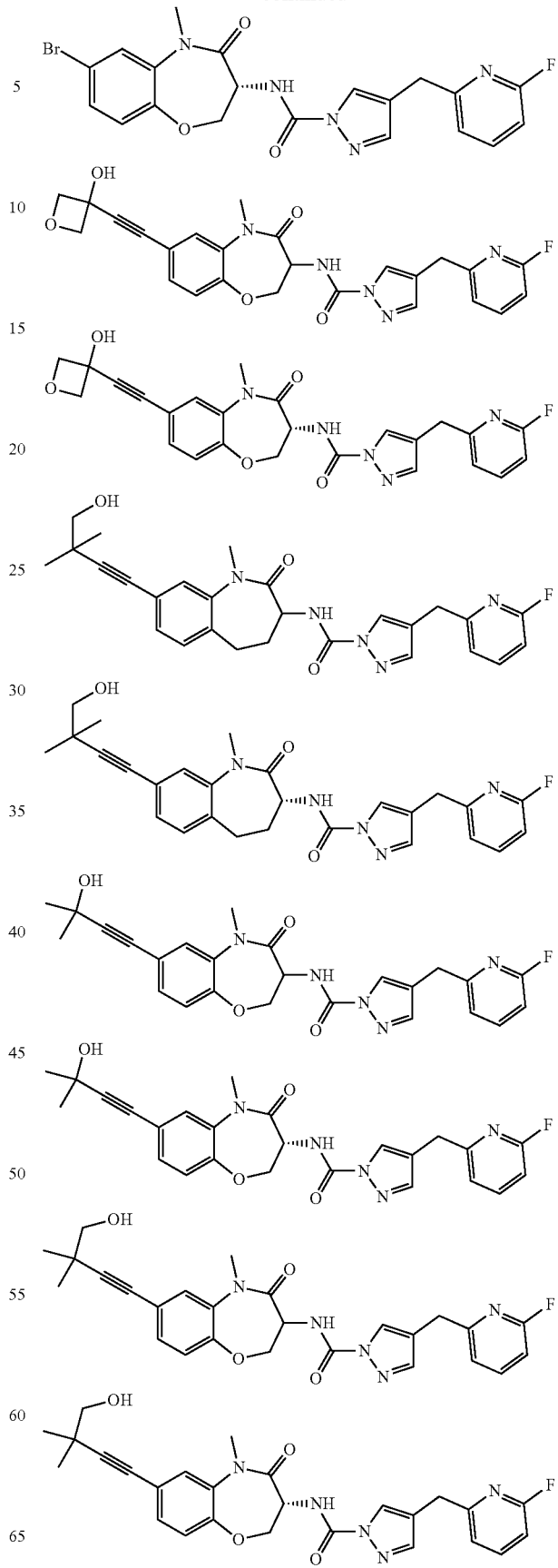

73
-continued
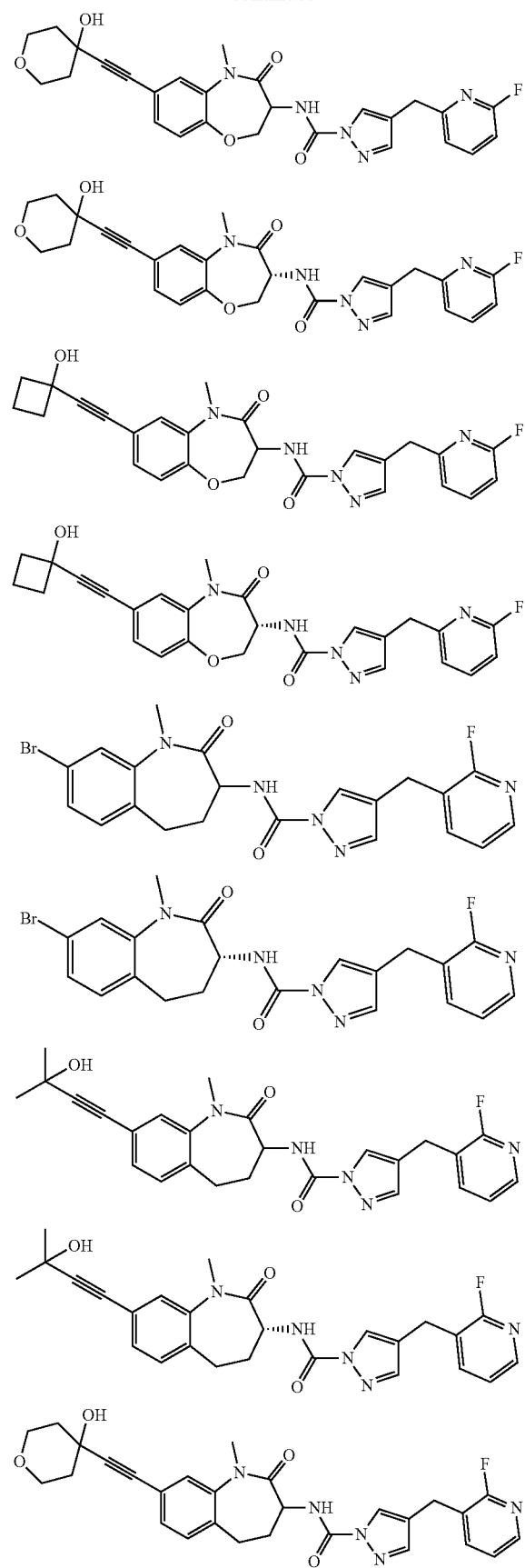
74
-continued
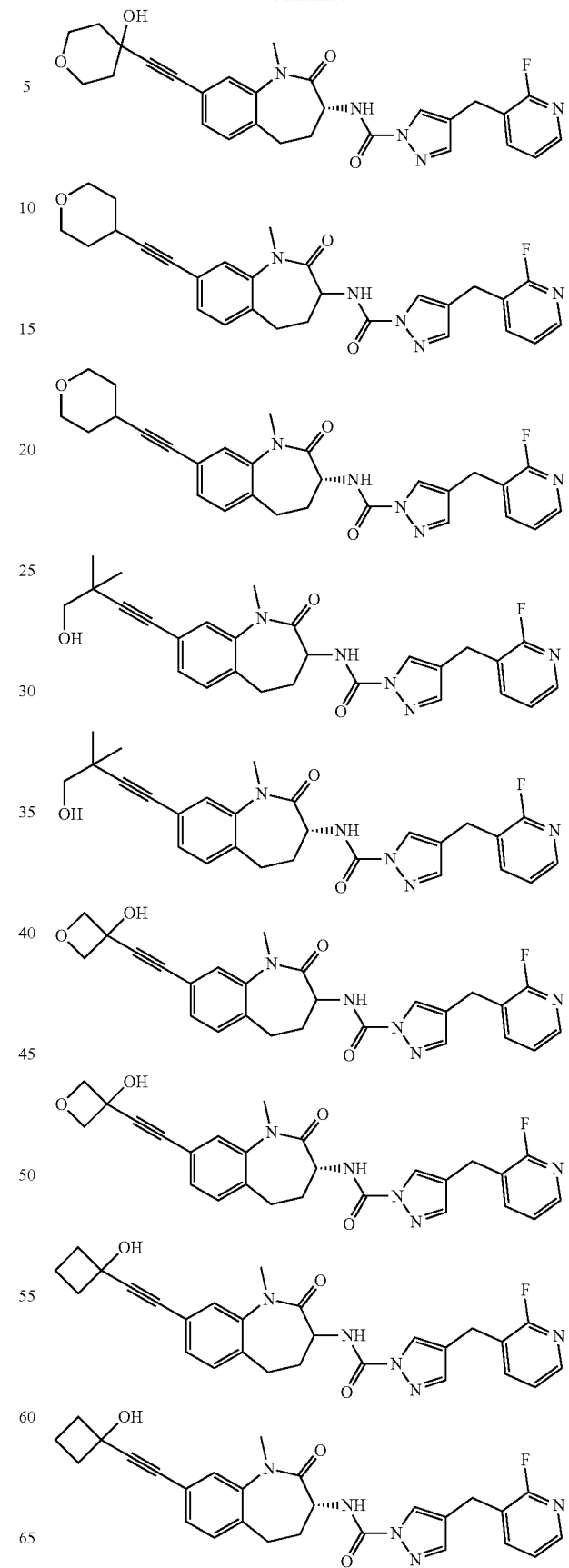

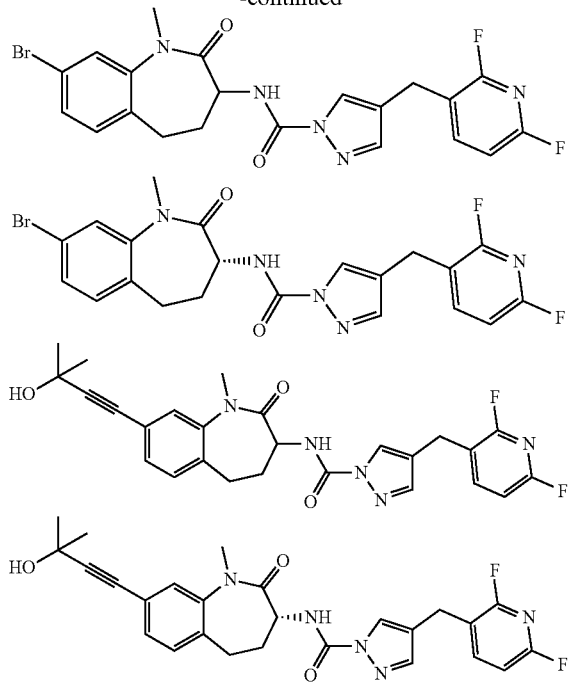

B. Combinations of Therapeutic Agents

The compounds described herein may be used alone, in combination with one another, in separate pharmaceutical compositions, together in a single pharmaceutical composition, or as an adjunct to, or in combination with, other established therapies. The compound or compounds or composition comprising the compound (or compounds) may be administered once, or in plural administrations. In some embodiments, the compounds of the present invention may be used in combination with other therapeutic agents useful for the disorder or condition being treated. These other therapeutic agents may be administered simultaneously, sequentially in any order, by the same route of administration, or by a different route as the presently disclosed compounds. For sequential administration, the compound(s) and the therapeutic agent(s) may be administered such that an effective time period of at least one compound and the therapeutic agent overlaps with an effective time period of at least one other compound and/or therapeutic agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or therapeutic agents overlap with each other.

In some embodiments, the compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The presently disclosed compounds also may be used advantageously with CAR-T therapies. Example of currently available CAR-T therapies are axicabtagene ciloleucel and tisagenlecleucel.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; FLT-3 inhibitors, such as gilteritinib and quizartinib, PI3-kinase inhibitors, such as idelalisib, Syk inhibitors, such as fostamatinib; and JAK inhibitors, such as ruxolitinib and fedratinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab; anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

III. Methods of Making Compounds

Disclosed embodiments of the present compounds can be prepared by any suitable method as will be understood by a person of ordinary skill in the art. One exemplary suitable method is provided below with reference to specific compounds in the examples, and can include the following first reaction step according to Scheme 1.

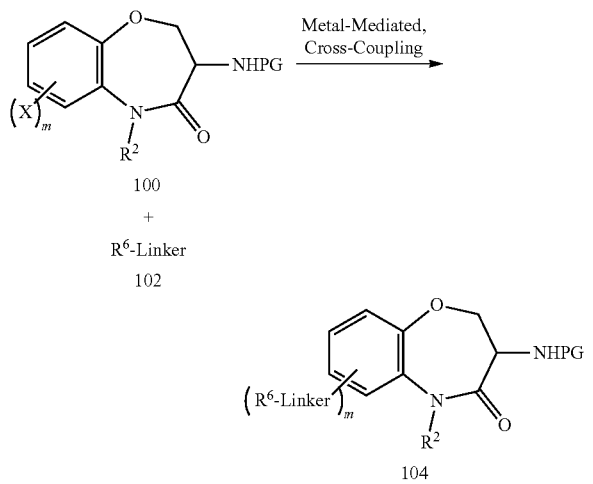

With reference to Scheme 1, protected amine precursor 100 can be coupled with $R^1$ group 102, which comprises an "$R^6$-linker" group as illustrated in Scheme 1, using a metal-mediated, cross-coupling reaction to provide the cross-coupled product 104. In some embodiments, the metal-mediated, cross-coupling reaction can be carried out using a transition metal catalyst, such as a palladium catalyst. Exemplary palladium catalysts include, but are not limited to, Pd(0) catalysts (e.g., $Pd_2(dba)_3$, $Pd(dba)_2$, $Pd(PPh_3)_4$, and the like) or Pd(II) catalyst (e.g., XPhos Pd generation 2 or generation 3, $PdCl_2$, $Pd(OAc)_2$, and the like). In some embodiments, the palladium catalyst can be used in combination with another co-catalyst, such as CuI, to promote the cross-coupling reaction, such as in a Sonogoshira reaction. The metal-mediated, cross-coupling also can comprise using a base, such as an amine base (e.g., $Et_3N$), or an inorganic base (e.g., $Cs_2CO_3$, $Na_2CO_3$, $K_2CO_3$ or the like), and a solvent (e.g., dimethylformamide). With reference to Scheme 1, X is a suitable group for metal-mediated, cross-coupling, such as a halogen or a triflate group and PG is an amine protecting group, which can be selected from, but is not limited to, a 9-fluorenylmethoxycarbonyl ("Fmoc") group, a t-butyloxycarbonyl ("Boc") group, a trityl ("Tr") group, an allyloxycarbonyl ("Alloc") group, a benzyloxycarbonyl ("Cbz") group, and the like.

Representative examples of the method steps shown in Scheme 1 are provided below in Scheme 2.

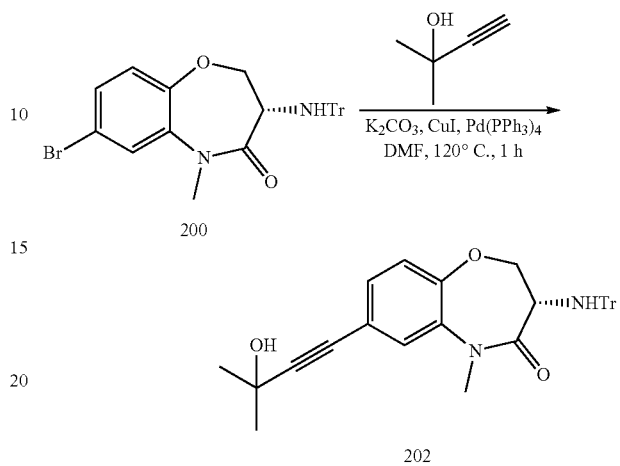

Once cross-coupled product 104 is made, it can be subjected to an optional linker group reduction step wherein linker groups comprising one or more sites of unsaturation can be reduced to saturated linker groups and/or linker groups having fewer degrees of unsaturation. If a linker reduction group is used, it can then be followed by a deprotection step and then an amide formation step, as illustrated in Scheme 3. Alternatively, if a linker group reduction step is not used, then cross-coupled product 104 can be deprotected and converted to amide compound 302.

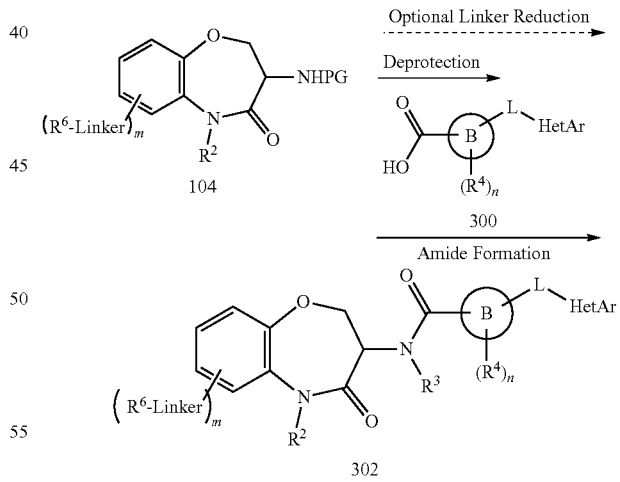

With reference to Scheme 3, an optional linker reduction step can be carried out. For example, if the linker comprises a site of unsaturation (e.g., a double or triple bond), the site of unsaturation can be reduced such that it becomes fully saturated (e.g., such as reducing a double bond and/or a triple bond to a single bond) or that it has few degrees of unsaturation (e.g., such as reducing a triple bond to a double bond). Suitable reagents for carrying out such an optional linker reduction step are recognized by those of ordinary skill in the art with the benefit of the present disclosure; however, one exemplary set of conditions includes exposing cross-coupled product 104 to H₂ in the presence of Pd on carbon. As these steps are optional, they need not be carried out in all embodiments. Instead, in some embodiments, cross-coupled product 104 can be deprotected to provide an amine that is then converted to amide compound 302 by reacting the amine with a suitable acid coupling partner 300, as illustrated in Scheme 3.

Alternatively, a urea-linked compound can be made from cross-coupled product 104, as illustrated in Scheme 4.

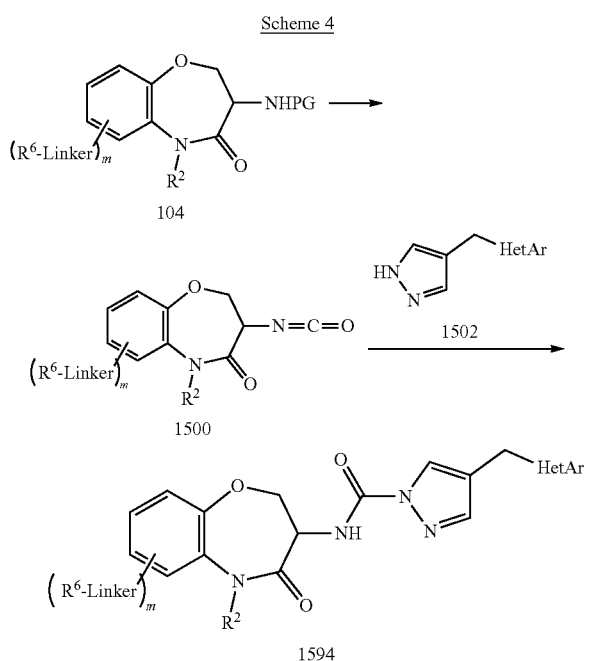

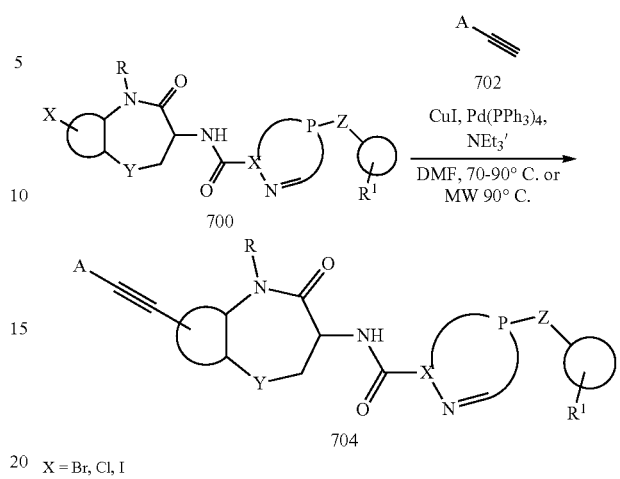

X = Br, Cl, I

With respect to Scheme 4, cross-coupled product 104 is deprotected to provide an amine, and then is treated with phosgene or a phosgene alternative, such as diphosgene or triphosgene, to form isocyanate 1500. Typically, phosgene or phosgene alternative treatment is performed in the presence of a suitable base, such as a trialkylamine, for example, triethylamine or diisopropylethylamine, and in an aprotic solvent, such as toluene, hexanes or a chlorinated solvent, for example, dichloromethane. Isocyanate 1500 then is treated with nitrogen heterocycle 1502 to form urea-linked compound 1504. The reaction typically is performed in a suitable solvent and in the presence of a suitable base, such as a solvent and/or base used for the phosgene or phosgene alternative treatment. In some embodiments, the isocyanate 1500 is not isolated after formation, and nitrogen heterocycle 1502 is simply added to the reaction mixture.

A number of the exemplary disclosed compounds are alkynyl substituted analogs. These compounds can be made using a metal-mediated coupling strategy as discussed above with reference to Scheme 1. Scheme 5 illustrates a more detailed general method for making alkynyl substituted analogs according to the present disclosure.

With reference to Scheme 5, nitrogen was bubbled through a stirring solution of a halide (1 equivalent), compound 700, CuI (0.1-0.2 equivalent), and Pd(PPh₃)₄ (0.05-0.1 equivalent) in dry DMF (3-4 mL/mmol) for 3 minutes in a vial. Subsequently, to the dark reaction solution was added NEt₃ (10 equivalents), followed by the corresponding alkyne (1.5-3 equivalents), compound 702, in quick succession. Nitrogen was bubbled through the reaction mixture for 2 minutes, and the vial capped. The reaction mixture was stirred at an effective reaction temperatures, such as 70-90° C., for an effective reaction period, such as 3-6 hours. Alternatively, the reaction mixture can be heated in a microwave reactor (30-45 minutes) until the halide 700 or 706 was consumed. The dark reaction solution was processed by one of the following methods: a) a work-up of diluting with ice-water/organic solvent; b) concentrated to dryness, followed by a work-up after diluting with ice-water/organic solvent; or c) the crude residue was diluted with ice-water, sonicated and the slurry allowed to warm to room temperature. The resulting grey/dark solid was collected by filtration, suction dried, dissolved in THF (20 mL), filtered through Celite®/silica gel pad, and the pad was washed with THF. Subsequently, the crude material was purified by reverse phase column chromatographic or by normal phase silica gel flash column chromatography to provide corresponding the alkynyl substituted analogs (Yield: 25-69%), compounds 704.

IV. Methods of Using Compounds

A. Diseases/Disorders

The disclosed compounds, as well as combinations and/or pharmaceutical compositions thereof, may be used to inhibit a RIP1 kinase by contacting the kinase either in vivo or ex vivo, with a compound or compounds of the present disclosure, or a composition comprising a compound or compounds of the present disclosure. Disclosed compound or compounds, or compositions comprising a disclosed compound or compounds also can be used to ameliorate, treat or prevent a variety of diseases and/or disorders. In particular embodiments, the disclosed compound, combinations of disclosed compounds, or pharmaceutical compositions thereof, may be useful for treating conditions in which inhibition of RIP1 or a pathway involving RIP1 is therapeutically useful. In some embodiments, the compounds directly inhibit RIP1 kinase activity. In certain embodiments, disclosed compounds are useful for treating autoimmune diseases, inflammatory disorders, cardiovascular diseases, nerve disorders, neurodegenerative disorders, allergic disorders, respiratory diseases, kidney diseases, cancers, ischemic conditions, erythrocyte deficiencies, lung and brain injuries (e.g., induced by ischemia-reperfusion or cisplatin and/or cerebrovascular accident), and bacterial and viral infections.

In some embodiments, the disclosed compound, combinations of disclosed compounds, or pharmaceutical compositions thereof, may be used to treat or prevent allergic diseases, amyotrophic lateral sclerosis (ALS), spinal muscular atrophy, systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or pharmaceutical compositions thereof, may also be useful for treating immune regulatory disorders related to bone marrow or organ transplant rejection or graft-versus-host disease. Examples of inflammatory and immune regulatory disorders that can be treated with the compounds (or pharmaceutical compositions or combinations thereof) include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, systemic inflammatory response syndrome, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, ischemia-reperfusion injuries, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis or myocardial infarction, scleroderma (including systemic scleroderma), anti-phospholipid syndrome, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, retinal degeneration, retinal detachment, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, alcoholic steatohepatitis, non-alcoholic steatohepatitis (NASH), autoimmune hepatobiliary diseases, acetaminophen toxicity, hepatotoxicity, hepatic failure, fulminant hepatic failure, late-onset hepatic failure, "acute-on-chronic" liver failure, chronic kidney diseases, kidney damage/injury (caused by, for example, nephritis, renal transplant, surgery, administration of nephrotoxic drugs, acute kidney injury), augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the compounds are useful for treating interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, lysosomal storage diseases (e.g., Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs disease, and Wolman disease).

In certain embodiments, the disclosed compound, combinations of disclosed compounds, or pharmaceutical compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of II-1 receptor antagonist), Alzheimer's disease, Huntington's disease, or Parkinson's disease.

Use of the present compounds in combination with other therapies is particularly useful in treating hyperproliferative disorders. The present compounds can be used to treat disorders such as cancers, leukemias and lymphomas in combination with the standard of care. By way of example, myelodysplastic syndrome (MDS) can be treated with a compound disclosed herein along with the standard of care. Therapeutics for use in combination with the present compounds include hypomethylating agents, such as azacitidine and decitabine, and other chemotherapeutic agents, such as cytarabine, daunorubicin and idarubicin. Immunomodulatory therapies, such as lenalidomide and CAR-T therapies, also can be used in combination with the present compounds for treating MDS.

Proliferative diseases that may be treated by the disclosed compound, combinations of disclosed compounds, or pharmaceutical compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, such as Hodgkins and Non-Hodgkins lymphoma, a mammary carcinoma, follicular carcinoma, undifferentiated carcinoma, papillary carcinoma, seminoma, melanoma, IL-1 driven disorders, hematopoietic neoplasms, such as the lymphomas mentioned above, MyD88 driven disorder (such as ABC diffuse large B-cell lymphoma (DLBCL) and Waldenström's macroglobulinemia), Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors, ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed compound, combinations of disclosed compounds, or pharmaceutical compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, postnasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or pharmaceutical compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

In one embodiment, the presently disclosed compounds can be used to slow the onset of the consequences of aging. For example, the present compounds reduce the heightened chronic inflammation associated with advanced age ("inflammaging"). Myriad symptoms and conditions are associated with inflammaging, by way of example, such conditions that can be treated with the present compounds include, neurodegenerative disorders, such as Parkinson's and Alzheimer's, hematopoietic neoplasms and myeloproliferative disorders. Additional conditions that can be treated or ameliorated by the present compounds include those described by Franceschi C, Campisi J. Chronic inflammation (inflammaging) and its potential contribution to age-associated diseases. *J Gerontol A Biol Sci Med Sci.* 2014; 69 Suppl 1:S4-S9. In another aspect, the present compounds can be used to reduce aging effects on the reproductive system. For example, necroptosis induced by RIP1 signaling has been implicated in the aging of reproductive organs by Li et al. *eLife* 2017; 6:e27692 and Chaudhary et al. *Journal of Biomedical Science* (2019) 26:11, thus the present compounds could be used to treat symptoms of associated with aging, such as reduced testosterone levels, reduced fertility and prostate hyperplasia.

Additional diseases or disorders that can be treated and/or prevented using compounds and compositions of the present invention include amyotrophic lateral sclerosis (ALS), an autoimmune syndrome, rheumatoid arthritis, type I diabetes mellitus, inflammatory bowel diseases, including Crohn's disease and ulcerative colitis, biliary cirrhosis, multiple sclerosis, Wegener's granulomatosis, ichthyosis, asthma, pollen allergies, reversible obstructive airway disease, bronchial asthma, allergic asthma, intrinsic asthma, extrinsic asthma, dust asthma, chronic or inveterate asthma, late asthma and airway hyper-responsiveness, allergic rhinitis, spondyloarthritis, ankylosing spondylitis, autoimmune hepatitis, autoimmune hepatobiliary diseases, cerebrovascular accident, allergic diseases, chronic obstructive pulmonary disease, pulmonary emphysema, Friedreich's ataxia, Lewy body disease, diabetic neuropathy, polyglutamine (polyQ) diseases, Fahr disease, Menke's disease, Wilson's disease, prion disorder, destructive bone disorders such as bone resorption disease, multiple myeloma-related bone disorder; benign tumor, proliferative disorders, inflammatory and hyperproliferative skin disorders, an epidermal hyperproliferation, psoriasis, atopic dermatitis, contact dermatitis, eczematous dermatitis, seborrhoeic dermatitis, pustular psoriasis, bullous dermatitis, dermatitis erythema multiforme, linear IgA bullous dermatitis, cement dermatitis, gingivitis, periodontitis, lesions of gingiva, alveolar bone, substantia ossea dentis, sepsis, pancreatitis, lichen planus, pemphigus, bullous pemphigoid, epidermolysis bullosa, urticaria, angioedemas, vasculitis, erythema, cutaneous eosinophilia, adiposis, eosinophilic fascitis, acne, alopecia areata, male pattern alopecia, alopecia senilis, keratoconjunctivitis, vernal conjunctivitis, corneal alkali burn, Behcet's disease, uveitis associated with Behcet's disease, keratitis, herpetic keratitis, conical cornea, dystrophia epithelialis corneae, corneal leukoma, ocular pemphigus, Mooren's ulcer, scleritis, Vogt-Koyanagi-Harada syndrome, hematological disorders, hematological malignancies, lymphomas, Hodgkins lymphoma, non-Hodgkins lymphoma, mammary carcinoma, follicular carcinoma, undifferentiated carcinoma, papillary carcinoma, seminoma, melanoma, ABC diffuse large B-cell lymphoma (DLBCL), Waldenström's macroglobulinemia, primary cutaneous T-cell lymphoma, smoldering or indolent multiple myeloma, leukemia, acute myeloid leukemia (AML), DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, splenic marginal zone lymphoma, multiple myeloma, plasmacytoma, intravascular large B-cell lymphoma, IL-1 driven disorders, MyD88 driven disorders, drug resistant malignancies, such as JAK inhibitor-resistant malignancies and ibrutinib resistant malignancies, for example ibrutinib resistant hematological malignancies, ibrutinib resistant CLL and ibrutinib resistant Waldenström's macroglobulinemia, acute myelogenous leukemia, chronic myelogenous leukemia; angiogenic disorders such as angiogenic disorders including solid tumors, ocular neovascularization, hemangiomas, such as infantile hemangiomas; sepsis, septic shock, shigellosis; migraine, bronchitis, gastric ulcers, necrotizing enterocolitis, intestinal lesions associated with thermal burns, celiac diseases, proctitis, eosinophilic gastroenteritis, mastocytosis, interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, a lysosomal storage disease, Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs disease, Wolman disease, Huntington's disease, Parkinson's disease, neurodegenerative diseases, Huntington's disease, Parkinson's disease, metastatic melanoma, neurodegeneration associated with HIV infection and CMV retinitis, such as associated neurocognitive disorders or dementia, fibrotic conditions such as, nonalcoholic steatohepatitis and cardiac conditions such as, ischemia reperfusion; allergies, adult respiratory distress syndrome, chronic obstructive pulmonary disease, glomerulonephritis, erythematosis, chronic thyroiditis, Graves' disease, autoimmune gastritis, autoimmune neutropenia, thrombocytopenia, graft versus host disease, inflammatory reaction induced by endotoxin, tuberculosis, atherosclerosis, muscle degeneration, cachexia, Reiter's syndrome, rubella arthritis, acute synovitis, pancreatic β-cell disease; diseases characterized by massive neutrophil infiltration; rheumatoid spondylitis, gouty arthritis, psoriatic arthritis, and other arthritic conditions, cerebral malaria, chronic pulmonary inflammatory disease, silicosis, pulmonary sarcoidosis, fibroid lung, idiopathic interstitial pneumonia, allograft rejection, bone marrow rejection, fever and myalgias due to infection, keloid formation, scar tissue formation, pyresis, influenza, chronic myelogenous leukemia; angiogenic disorders including solid tumors; viral diseases including acute hepatitis infection (including hepatitis A, hepatitis B and hepatitis C), AIDS, ARC or malignancy, herpes; stroke, myocardial infarction, arteriosclerosis, atherosclerosis, aortitis syndrome, polyarteritis nodosa, myocardial ischemia, ischemia in stroke heart attacks, organ hypoxia, vascular hyperplasia, cardiac and renal reperfusion injury, ischemia-reperfusion injury of organs which occurs upon preservation, transplantation or ischemic disease, cardiac hypertrophy, thrombin-induced platelet aggregation, endotoxemia and/or toxic shock syndrome, conditions associated with prostaglandin endoperoxidase syndase-2, pemphigus vulgaris, autoimmune/multiple myositis, dermatomyositis, leukoderma vulgaris, photoallergic sensitivity, ischemia reperfusion injury, cardiac ischemia reperfusion injury arising from myocardial infarction, multiple system atrophy, Parkinson-plus syndromes, frontotemporal dementia, intracranial hemorrhage, cerebral hemorrhage, progressive muscular atrophy, pseudobulbar palsy, progressive bulbar palsy, spinal muscular atrophy, inherited muscular atrophy, peripheral neuropathies, progressive supranuclear palsy, corticobasal degeneration, demyelinating diseases, systemic onset juvenile idiopathic arthritis (SoJIA) or Still's disease, systemic lupus erythematosus (SLE), Sjögren's syndrome, anti-phospholipid syndrome (APS), primary sclerosing cholangitis (PSC), renal transplant, surgery, acute kidney injury (AKI), systemic inflammatory response syndrome (SIRS), cytokine release syndrome (CRS), acute respiratory distress syndrome (ARDS), ARDS resulting from COVID-19, postinfectious autoimmune diseases, rheumatic fever, post-infectious glomerulonephritis, systemic sclerosis, cerebrovascular accident (CVA), chronic obstructive pulmonary disease (COPD), NEMO-deficiency syndrome (F-kappa-B essential modulator gene (also known as IKK gamma or IKKG) deficiency syndrome), solid organ malignancies, lysosomal storage diseases, glaucoma, retinal degenerative disease, retinal ischemia/reperfusion injury, renal ischemia reperfusion injury, cataracta, siderosis, retinitis pigmentosa, retinal degeneration, retinal detachment, senile macular degeneration, vitreal scarring, anthrax lethal toxin induced septic shock, cell death induced by LPS, infectious encephalopathy, encephalitis, allergic encephalomyelitis, autoimmune uveoretinitis, giant cell arteritis, regional enteritis, granulomatous enteritis, distal ileitis, regional ileitis, terminal ileitis, insulin-dependent diabetes mellitus, scleroderma, systemic scleroderma, macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, posterior uveitis, toxic retinitis and light-induced toxicity, macular edema, central areolar choroidal dystrophy, BEST disease, adult vitelliform disease, pattern dystrophy, optic nerve injury, optic neuritis, optic neuropathies, central retinal artery occlusion, ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy and hereditary optic neuropathy, Dominant Optic Atrophy, Behr's syndrome, Creutzfeldt-Jakob disease), progressive supranuclear palsy, hereditary spastic paresis, subarachnoid hemorrhage, perinatal brain injury, subclinical brain injury, spinal cord injury, anoxic-ischemic brain injury, cerebral ischemia, focal cerebral ischemia, global cerebral ischemia, and hypoxic hypoxia, peritoneal damage caused by peritoneal dialysis fluid (PDF) and PD-related side effects, glomerular diseases, tubulointerstitial diseases, interstitial nephritis, obstruction, polycystic kidney disease), focal glomerulosclerosis, immune complex nephropathy, diabetic nephropathy, Goodpasture's syndrome, hepatocellular cancer, pancreatic cancer, urological cancer, bladder cancer, colorectal cancer, colon cancer, breast cancer, prostate cancer, prostate hyperplasia, renal cancer, kidney carcinoma, liver carcinoma, adrenal gland carcinoma, thyroid cancer, gall bladder cancer, peritoneal cancer, ovarian cancer, cervical cancer, gastric cancer, endometrial cancer, esophageal cancer, stomach cancer, head and neck cancer, neuroendocrine cancer, CNS cancer, brain tumors (e.g., carcinoma of the brain, glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, epithelial neoplasia, stomach carcinoma, carcinoma of the ovaries, rectum carcinoma, prostate carcinoma, carcinoma of the pancreas, lung carcinoma, carcinoma of the vagina, carcinoma of the cervix, carcinoma of the testis, carcinoma of the genitourinary tract, carcinoma of the esophagus, carcinoma of the larynx, carcinoma of the skin, carcinoma of the bone, carcinoma of the thyroid, sarcoma, glioblastomas, neuroblastomas, gastrointestinal cancer, adenoma, adenocarcinoma, keratoacanthoma, epidermoid carcinoma, large cell carcinoma, non-small-cell lung carcinoma, lymphomas, colon carcinoma, colorectal adenoma, hemangiopericytomas, myxoid carcinoma, round cell carcinoma, squamous cell carcinomas, esophageal squamous cell carcinomas, oral carcinomas, vulval cancer, cancers of the adrenal cortex, ACTH producing tumors, and leukemia, respiratory infectious viruses, such as influenza virus, rhinovirus, corona virus, parainfluenza virus, RS virus, adeno virus, reo virus and the like), herpes zoster caused by herpes virus, diarrhea caused by rotavirus, viral hepatitis, AIDS, bacterial infectious diseases, such as *Bacillus cereus, Vibrio parahaemolyticus*, Enterohemorrhagic *Escherichia coli, Staphylococcus aureus*, MRSA, *Salmonella, Botulinus, Candida*, Paget's disease, achondroplasia, osteochodrytis, hyperparathyroidism, osteogenesis imperfecta, partial liver resection, acute liver necrosis, necrosis caused by toxin, necrosis caused by viral hepatitis, necrosis caused by shock, necrosis caused by anoxia, B-virus hepatitis, non-A/non-B hepatitis, cirrhosis, alcoholic liver disease, alcoholic cirrhosis, alcoholic steatohepatitis, non-alcoholic steatohepatitis (NASH), acetaminophen toxicity, hepatotoxicity, hepatic failure, fulminant hepatic failure, late-onset hepatic failure, "acute-on-chronic" liver failure, chronic kidney diseases, kidney damage/injury, kidney damage/injury caused by nephritis, kidney damage/injury caused by renal transplant, kidney damage/injury caused by surgery, kidney damage/injury caused by administration of nephrotoxic drugs, augmentation of chemotherapeutic effect, cytomegalovirus infection, HCMV infection, AIDS, cancer, senile dementia, trauma, chronic bacterial infection, diseases caused by environmental pollution, aging, hypobaropathy, disease caused by histamine or leukotriene-C4 release, muscular dystrophy, pyoderma and Sezary's syndrome, Addison's disease, pseudomembranous colitis, colitis caused by drug or radiation, ischemic acute renal insufficiency, chronic renal insufficiency, toxinosis caused by lung-oxygen or drugs, congenital hypophosphatasia, fibromatous lesions, fibrous displasia, bone turnover, osteolytic bone disease, treating post-traumatic bone surgery, treating post-prosthetic joint surgery, treating post-plastic bone surgery, treating post-dental surgery, bone chemotherapy treatment or bone radiotherapy treatment, bone cancer, fragile plaque, disorder, occlusive disorder, stenosis, coronary artery disorders, peripheral arterial disorders, arterial occlusion, aneurysm formation, post-traumatic aneurysm formation, restenosis, post-operative graft occlusion, Guillain-Barre syndrome, Meniere's disease, polyneuritis, multiple neuritis, mononeuritis, radiculopathy, hyperthyroidism, Basedow's disease, autoimmune idiopathic thrombocytopenic purpura (autoimmune ITP), membranous nephritis, autoimmune thyroiditis, Hashimoito's thyroiditis, myasthenia gravis, cold and warm agglutinin diseases, Evan's syndrome, hemolytic uremic syndrome/thrombotic thrombocytopenic purpura (HUS/TTP), autoimmune hemolytic anemia, agranulocytosis, pernicious anemia, megaloblastic anemia, anerythroplasia, and combinations thereof.

For particular embodiments, at least one compound, or a composition comprising at least one compound, according to the present invention is administered to a subject having, or potentially developing, atopic dermatitis. In another particular embodiment, at least one compound, or a composition comprising at least one compound, according to the present invention is administered to a subject having, or potentially developing, rheumatoid arthritis. In another particular embodiment, at least one compound, or a composition comprising at least one compound, according to the present invention is administered to a subject having, or potentially developing, ankylosing spondylitis. In another particular embodiment, at least one compound, or a composition comprising at least one compound, according to the present invention is administered to a subject having, or potentially developing, myelodysplastic syndrome.

B. Formulations and Administration

Pharmaceutical compositions comprising one or more active compounds of the invention may be manufactured by any suitable method, such as mixing, dissolving, granulating, dragee-making, levigating, emulsifying, encapsulating, entrapping or lyophilization processes. The pharmaceutical compositions may be formulated using one or more physiologically acceptable excipients (e.g., diluents, carriers, or auxiliaries), one or more adjuvants, or combinations thereof to provide preparations which can be used pharmaceutically.

The active compound(s) may be formulated in the pharmaceutical compositions per se, or in the form of a pharmaceutically acceptable salt, a stereoisomer, an N-oxide, a tautomer, a hydrate, a solvate, an isotope, or a prodrug thereof. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), pharmaceutically acceptable salt, stereoisomer, N-oxide, tautomer, hydrate, solvate, isotope, or prodrug may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The pharmaceutical compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable excipients such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound, as is well known.

For buccal administration, the pharmaceutical compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), pharmaceutically acceptable salt, stereoisomer, N-oxide, tautomer, hydrate, solvate, isotope, or prodrug can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (14 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the disclosed compound(s), 1% (v/v) polysorbate 80 (TWEEN® 80), 50 mM citrate and/or 0.9% sodium chloride.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat.

Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

Several approaches exist for transporting molecules across the blood brain barrier. These include, but are not limited to physical methods, lipid-based methods, and receptor and channel-based methods. Physical methods of transporting a compound across the blood-brain barrier include, but are not limited to, circumventing the blood-brain barrier entirely, and/or creating openings in the blood-brain barrier. Circumvention methods include, but are not limited to, direct injection (e.g., Papanastassiou et al., Gene Therapy 9:398-406, 2002), interstitial infusion/convection enhanced delivery (Bobo et al., Proc. Natl. Acad. Sci. U.S.A. 91:2076-2080, 1994), and implanting a delivery device in the brain (see, e.g., Gill et al., Nature Med. 9:589-595, 2003. Openings in the blood-brain barrier include, but are not limited to, ultrasound, osmotic pressure (e.g., by administration of hypertonic mannitol and permeabilization by, e.g., bradykinin or permeabilizer A-7 (see, e.g., U.S. Pat. Nos. 5,112,596, 5,268,164, 5,506,206, and 5,686,416). Compounds also may be encapsulated in liposomes that are coupled to antibody binding fragments that bind to receptors on the vascular endothelium of the blood-brain barrier.

For certain embodiments, the compounds can be administered continuously by infusion into the fluid reservoirs of the CNS or by bolus injection. Compounds can be administered using an indwelling catheter and a continuous administration means such as a pump, or by Implantation of a sustained-release vehicle. For example, the compounds may be injected through chronically implanted cannulas or chronically infused with the help of osmotic minipumps. Subcutaneous pumps can deliver compounds to the cerebral ventricles.

C. Dosages

The disclosed compound, pharmaceutical compositions, or combinations of disclosed compounds will generally be used in an amount effective to achieve the intended result, for example, in an amount effective to inhibit a RIP1 kinase and/or to treat, prevent or ameliorate a particular condition. The disclosed compound(s), or pharmaceutical compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, respiratory distress syndrome, chronic obstructive pulmonary disease, and respiratory infections. Dosage, and frequency of administration of the disclosed compound(s) or pharmaceutical compositions thereof, will also depend on whether the disclosed compound(s) are formulated for treatment of acute episodes of a condition or for the prophylactic treatment of a disorder. A person of ordinary skill in the art will be able to determine the optimal dose for a particular individual.

For prophylactic administration, the disclosed compound, combinations of disclosed compounds, or pharmaceutical compositions thereof, can be administered to a patient or subject at risk of developing one of the previously described conditions. For example, if it is unknown whether a patient or subject is allergic to a particular drug, the disclosed compound, combinations of disclosed compounds, or pharmaceutical compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed compound(s), or pharmaceutical composition thereof, can be administered to an allergy sufferer prior to expected exposure to the allergen. A disclosed compound, combinations of disclosed compounds, or pharmaceutical compositions thereof, can also be administered prophylactically to healthy individuals who are repeatedly exposed to agents known to one of the above-described maladies to prevent the onset of the disorder. For example, a disclosed compound, combinations of disclosed compounds, or pharmaceutical compositions thereof, can be administered to a healthy individual who is repeatedly exposed to an allergen known to induce allergies, such as latex, in an effort to prevent the individual from developing an allergy. Alternatively, a disclosed compound, combinations of disclosed compounds, or pharmaceutical compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, from greater than 0 to 0.1 µM, or from greater than 0 to 0.05 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

In some embodiments, assays suitable for determining RIP1 activity can be used. Such assay methods can be used to evaluate the efficacy of compound embodiments disclosed herein and/or that can be used to determine amounts/dosages of the compound embodiments that can provide a desired efficacy. In some embodiments, the assay can be an ADP-Glo™ assay that assesses the ability of a compound embodiment to inhibit RIP1. In other embodiments, whole cell assays using mouse and/or human cells, such as U937 and/or L929 cell necroptosis assays, can be performed to determine safe and effective doses of compounds that can be used in human in vivo studies. Using these whole cell assays, the compound's activity against human and/or murine RIP1 can be assessed in an in vitro context, which then allows a person of ordinary skill in the art to determine safe and effective dosages for in vivo use. Yet another assay that can be used to evaluate the activity of compound embodiments described herein to treat a disease or condition involving RIP1 is an acute hypothermia mouse model, which assesses the compound's ability to inhibit TNF-alpha induced hypothermia. Each of these assays, and various results from using these assays, are described in detail in the Examples section of the present disclosure.

Dosage amounts of disclosed compounds will typically be in the range of from greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed compound, its bioavailability, the mode of administration, and various factors discussed above.

Dosage amount and dosage interval can be adjusted for individuals to provide plasma levels of the disclosed compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Pharmaceutical compositions comprising one or more of the disclosed compounds typically comprise from greater than 0 up to 99% of the disclosed compound, or compounds, and/or other therapeutic agent by total weight percent. More typically, pharmaceutical compositions comprising one or more of the disclosed compounds comprise from about 1 to about 20 total weight percent of the disclosed compound and other therapeutic agent, and from about 80 to about 99 weight percent of a pharmaceutically acceptable excipient. In some embodiments, the pharmaceutical composition can further comprise an adjuvant.

Preferably, the disclosed compound, combinations of disclosed compounds, or pharmaceutical compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

V. Examples

Example 1

Compounds of the present disclosure can be made using a suitable starting compound, such as compound 200 or compound 206, illustrated in the schemes above. A representative method for making compound 200 is illustrated in Scheme 6A and a representative method for making compound 206 is illustrated in Scheme 6B.

Scheme 6A

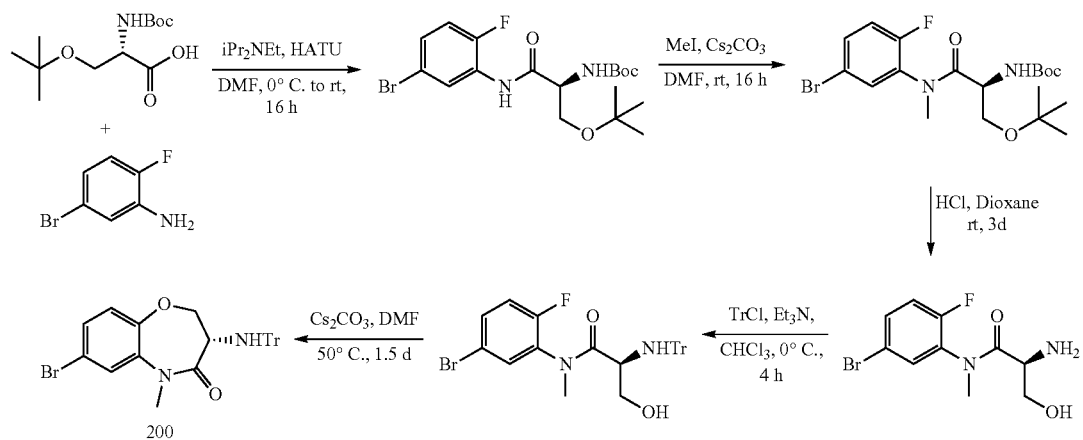

Scheme 6B

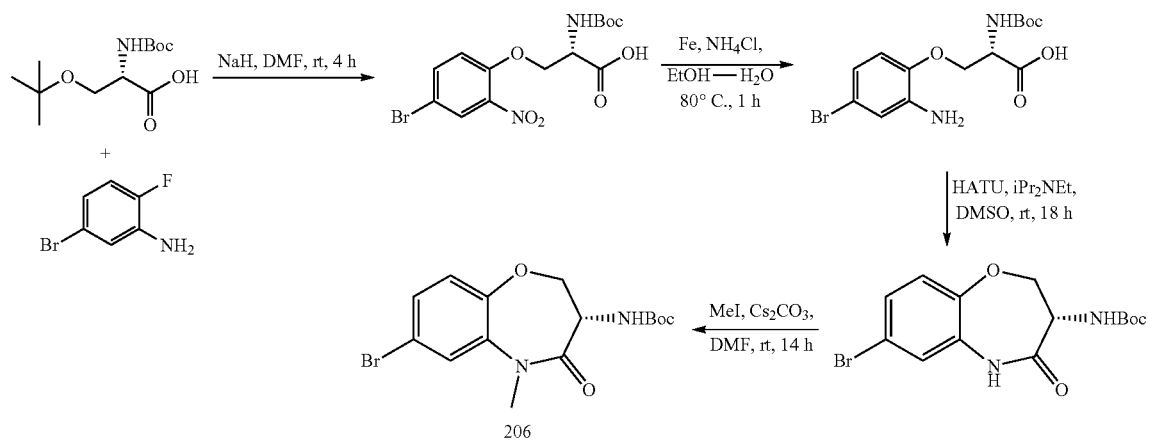

Spectral characterization for 3-(S)—N-trityl-amino-7-bromo-5-methyl-4-oxobenzoxazapine (200): ¹H nmr (400 MHz, CDCl₃) δ 7.41-7.38 (6H, m, 6H of C(C₆H₅)₃), 7.25-7.15 (10H, m, oxobenzoxazapineH-8, 9H of C(C₆H₅)₃), 7.00 (1H, d, J 2.5 Hz, oxobenzoxazapineH-6), 6.91 (1H, d, J 8.5 Hz, oxobenzoxazapineH-9), 4.50 (1H, dd, J 10.0, 7.5 Hz, 1H of oxobenzoxazapineH-2), 4.37 (1H, dd, J 11.5, 10.0 Hz, 1H of oxobenzoxazapineH-2), 3.53 (1H, dd, J 11.5, 7.5 Hz, oxobenzoxazapineH-3), 3.30 (1H, br s, NH), 2.87 (3H, s, NCH₃).

Example 2

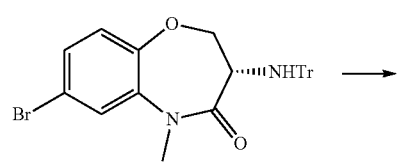

Synthesis of (S)-7-(3-hydroxy-3-methylbut-1-yn-1-yl)-5-methyl-3-(tritylamino)-2,3-dihydrobenzo[b][1,4]oxazepin-4(5H)-one: A mixture of the bromooxazapine (0.210 g, 0.410 mmol, 1.0 eq) potassium carbonate (0.566 g, 4.101 mmol, 10.0 eq) and copper(I) iodide (0.008 g, 0.041 mmol, 0.1 eq) in dimethylformamide (3.0 mL) was degassed by bubbling argon through for five minutes. 2-Methyl-2-hydroxybut-3-yne (0.052 g, 0.060 mL, 0.615 mmol, 1.5 eq) and tetrakis(triphenylphosphine)palladium (0.024 g, 0.021 mmol, 0.05 eq) were added and the reaction sealed before heating in the microwave to 120° C. for 1 hour. The reaction was partitioned between EtOAc (80 mL) and water (80 mL). The organics were washed with brine (80 mL), water (80 mL)

and brine (80 mL), dried (Na$_2$SO$_4$) and concentrated under reduced pressure. MPLC (10→80% EtOAc-hexane) yielded the starting material (0.091 g) and the title compound (0.079 g) as a colorless oil; $^1$H nmr (400 MHz, CDCl$_3$) δ 7.40-7.38 (6H, m, 6H of C(C$_6$H$_5$)$_3$), 7.24-7.7.14 (9H, m, 9H of C(C$_6$H$_5$)$_3$), 7.13 (1H, dd, J 8.0, 2.0 Hz, oxobenzoxazapineH-8), 6.96 (1H, d, J 8.0 Hz, oxobenzoxazapineH-9), 6.95 (1H, d, J 2.5 Hz, oxobenzoxazapineH-6), 4.48 (1H, dd, J 10.0, 7.5 Hz, 1H of oxobenzoxazapineH-2), 4.37 (1H, dd, J 11.5, 10.0 Hz, 1H of oxobenzoxazapineH-2), 3.55 (1H, dd, J 11.5, 7.5 Hz, oxobenzoxazapineH-3), 2.78 (3H, s, NCH$_3$), 1.62 (6H, s, C(CH$_3$)$_2$); m/z: 555 [M+K]$^+$, 243 [C(C$_6$H$_5$)$_3$]$^+$.

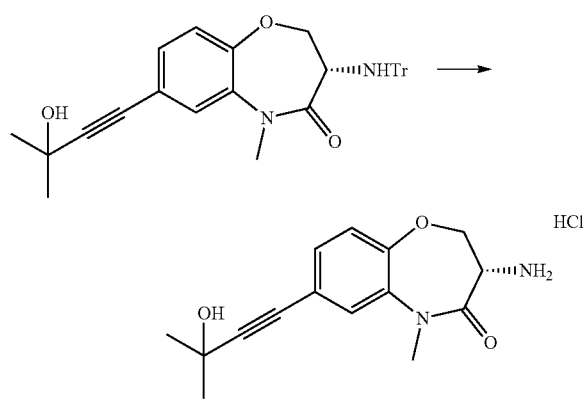

Deprotection of the Trityl Group: To a solution of the trityl protected amine (0.079 g, 0.153 g, 1.0 eq) in dioxane (2.0 mL) was added a solution of hydrogen chloride (0.15 mL of a 4M solution in dioxane, 0.614 mmol, 4.0 eq). The reaction was stirred at room temperature for 6 hours before concentrating to dryness to obtain a white solid, which was used without purification; m/z: 275 [M+H]$^+$.

Example 3

This example provides a method for making N-substituted-4-[(heteroaryl)methyl]-1H-pyrazole-1-carboxamides through intermediate of pyrazole-1-carbonyl chloride formation according to Scheme 7 (Route 1).

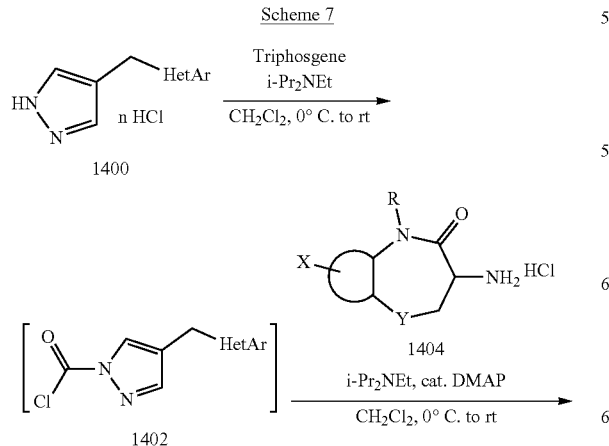

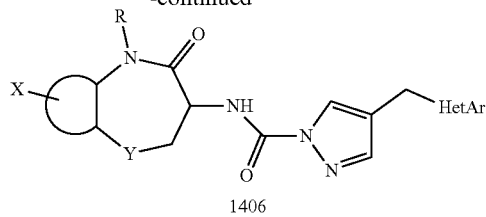

To a stirring heterogeneous mixture of compound 1400 (1 eq) and triphosgene (1.5 eq) in CH$_2$Cl$_2$ (15 mL/mmol) under nitrogen at 0° C. was added i-Pr$_2$NEt (5-9 eq) over time (15 min/mmol). Red reaction solution was stirred at 0° C. for 1 h, warmed to room temperature (2 h), analyzed 4-[(heteroaryl)methyl]-1H-pyrazole consumption by LC/MS and concentrated to dryness to provide 1402. The red semi-solid concentrate was added to 1404 or the corresponding amine or its salt (1 eq) and DMAP (0.1 eq) and cooled in ice-bath under nitrogen. CH$_2$Cl$_2$ (15 mL/mmol) was added to the flask, stirred for 15 min and the stirring red solution was treated with i-Pr$_2$NEt (5-9 eq) over time (15 min/mmol). Ice-bath was removed after 1 hour and allowed the reaction solution to warm to room temperature. Upon analysis of the reaction progress, the reaction solution was concentrated to dryness, diluted with water and an extractive work-up performed with either EtOAc or CH$_2$Cl$_2$. Silica gel flash column chromatographic purification of the crude concentrate provided the requisite N-substituted-4-[(heteroaryl)methyl]-1H-pyrazole-1-carboxamide 1406 (Yield: 20-75%).

Example 4

This example provides a method for making N-substituted-4-[(heteroaryl)methyl]-1H-pyrazole-1-carboxamides though intermediate isocyanate formation according to Scheme 8 (Route 2).

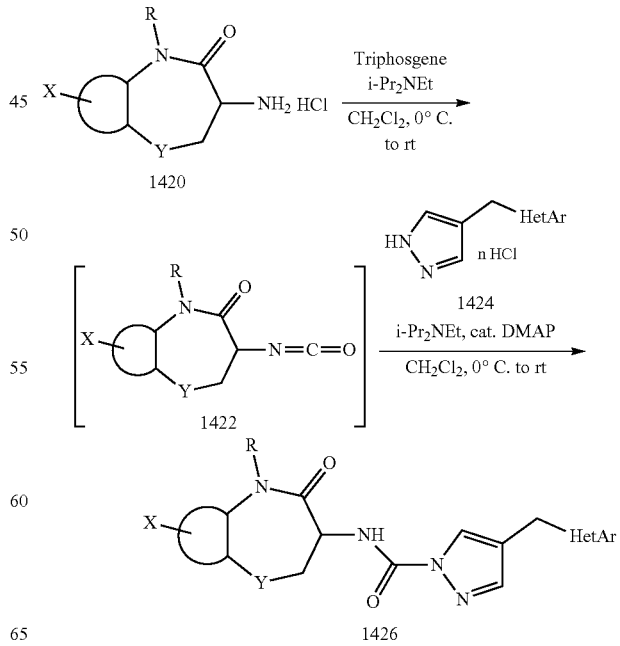

i-Pr$_2$NEt (10-15 eq) overtime (20 min/mmol) was added to a stirring heterogeneous mixture of compound 1420, or its corresponding amine or its salt (1 eq), and triphosgene (2.3 eq) in CH$_2$Cl$_2$ (15 mL/mmol) under nitrogen at 0° C. Pale yellow reaction solution was stirred at 0° C. for 1 hour, warmed to room temperature (2 hours), analyzed corresponding amine consumption by LC/MS and concentrated to dryness. To the red semi-solid concentrate comprising compound 1422 was added 4-[(heteroaryl)methyl]-1H-pyrazole hydrochloride 1424 (0.9 eq) and DMAP (0.1 eq) and cooled in ice-bath under nitrogen. CH$_2$Cl$_2$ (15 mL/mmol) was added to the flask, stirred for 15 minutes and the stirring red solution was treated with i-Pr$_2$NEt (10-15 eq) over time (15 min/mmol). Ice-bath was removed after 1 hour and the reaction solution allowed to warm to room temperature (6-8 hours). Upon analysis of the progress, reaction solution was concentrated to dryness, diluted with water and an extractive work-up was performed using either EtOAc or CH$_2$Cl$_2$. Silica gel flash column chromatographic purification of the resulting crude provided the requisite N-substituted-4-[(heteroaryl)methyl]-1H-pyrazole-1-carboxamide 1426 (Yield: 19-73%).

Example 5

This example provides a method for making embodiments of disclosed alkynyl substituted compounds according to Scheme 9 (Route 3).

Scheme 9

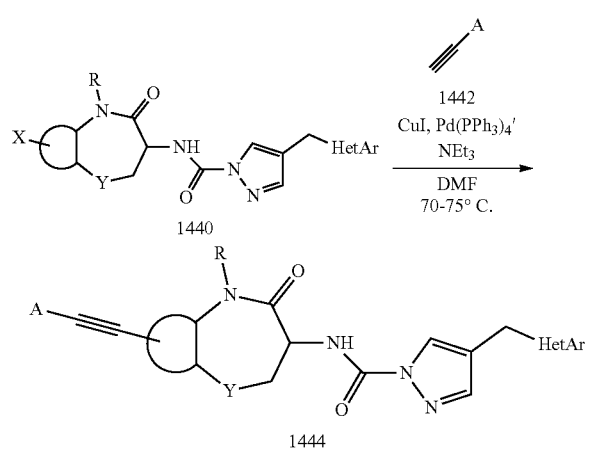

Nitrogen was bubbled through stirring solution of halide 1440 (1 eq) and CuI (0.1-0.2 eq), Pd(PPh$_3$)$_4$ (0.05-0.1 eq) in dry DMF (3-4 mL/mmol) for 3 minutes in a vial. Subsequently, NEt$_3$ (10 eq) was added to the dark reaction solution followed by corresponding alkyne 1442 (1.5-3 eq) in quick succession. Nitrogen was bubbled through the reaction mixture for 2 minutes, the vial capped, and the reaction mixture stirred at 70-75° C. for 5-6 hours. The dark reaction solution was concentrated to dryness after analyzing the reaction progression by LC/MS analysis. Crude residue was diluted with ice-water, sonicated and the slurry was warmed to room temperature. The resulting grey/dark solid was collected by filtration, suction dried, dissolved in THF (20 mL), filtered through Celite®/silica gel pad, and the pad was washed with THF. After concentration of the filtrate, the crude material was purified by flash chromatography to obtain alkynyl substituted analogs 1444 (Yield: 25-69%).

Example 6

This example provides a method for making embodiments of disclosed 4-[(heteroaryl)methyl]-1H-pyrazole compounds according to Scheme 10.

Scheme 10

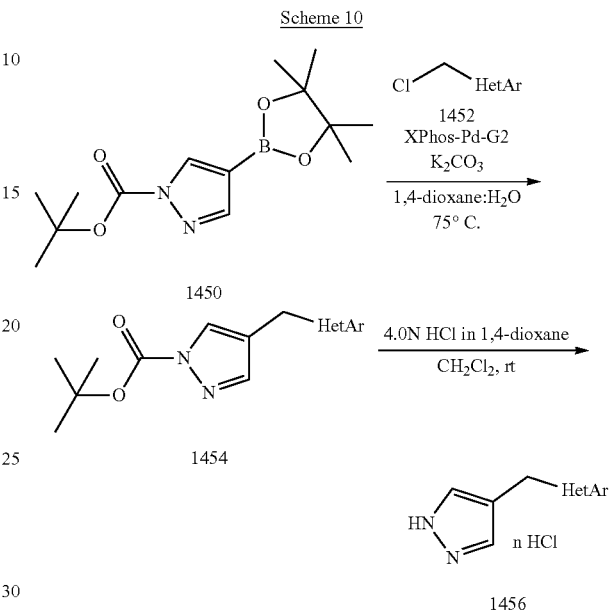

A stirring mixture of 1-boc-pyrazole-4-boronic acid pinacol ester 1450 (1 mmol), (chloromethyl)heteroarene (1.3 mmol) 1452, XPhos-Pd-G2 (0.05 mmol) and K$_2$CO$_3$ (3-4 mmol) in 1,4-dioxane:H$_2$O (9:1, 10 mL/mmole) was degassed by high vacuum and back purged with argon in a balloon in three cycles over a period of 5-10 minutes and heated at 70-75° C. for 2-6 hours. The reaction mixture was cooled and concentrated to dryness. The crude residue was diluted with EtOAc (or CH$_2$Cl$_2$), water and saturated aq. Na$_2$CO$_3$ (6 mL/mmole). Organic layer was separated, and the aqueous layer was extracted with EtOAc (or CH$_2$Cl$_2$). Combined organic layers were washed with aq. NaCl, stirred over anhydrous Na$_2$SO$_4$, and filtered through Celite®. Upon concentration of the filtrate, crude was purified by silica gel chromatography to obtain tert-butyl 4-[(heteroaryl)methyl]-1H-pyrazole-1-carboxylate (yield 49-85%) 1454. 4.0 N HCl in 1,4-dioxane (5-7 eq) was added to stirring solution of 4-[(heteroaryl)methyl]-1H-pyrazole (1 eq) in CH$_2$Cl$_2$ (3-6 mL/mmol) at room temperature. Reaction mixture was stirred till the consumption of tert-butyl 4-[(heteroaryl)methyl]-1H-pyrazole-1-carboxylate and concentrated to dryness. The crude solid was sonicated in EtOAc (6-7 mL/mmol), filtered, washed with EtOAc on the funnel and suction dried for short time. Thus, collected semi-dried solid was further dried under high vacuum and obtained as a 4-[(heteroaryl)methyl]-1H-pyrazole hydrochloride salt 1456 (80-98%) and used in the next step with no further purification (purity >95%).

tert-Butyl
4-(pyridin-2-ylmethyl)-1H-pyrazole-1-carboxylate

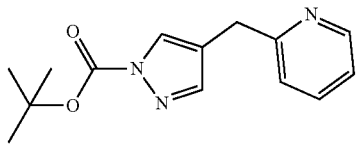 [SMILES: CC(C)(C)OC(=O)n1cc(Cc2ccccn2)cn1]

$^1$H NMR (400 MHz, Chloroform-d) δ 8.49 (ddd, J=4.9, 1.9, 1.0 Hz, 1H), 7.89 (q, J=0.9 Hz, 1H), 7.57 (d, J=2.0 Hz, 1H), 7.54 (dd, J=7.7, 1.9 Hz, 1H), 7.15-6.99 (m, 2H), 3.94 (d, J=0.9 Hz, 2H), 1.57 (s, 9H). LCMS: Purity 95%, MS (m/e) 260 (M+H)$^+$ 2-((1H-Pyrazol-4-yl)methyl)pyridine dihydrochloride

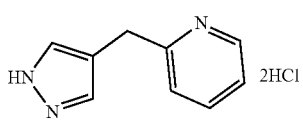 [SMILES: c1ccc(Cc2cn[nH]c2)nc1]

LC/MS: Purity 96%, MS (m/e) 160 (M−2HCl+H)$^+$.

tert-Butyl 4-((6-methylpyridin-2-yl)methyl)-1H-pyrazole-1-carboxylate

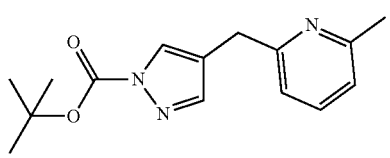 [SMILES: Cc1cccc(Cc2cnn(C(=O)OC(C)(C)C)c2)n1]

$^1$H NMR (400 MHz, Chloroform-d) 67.92 (q, J=0.9 Hz, 1H), 7.62 (d, J=0.9 Hz, 1H), 7.49 (t, J=7.7 Hz, 1H), 7.00 (ddd, J=7.7, 1.1, 0.5 Hz, 1H), 6.96-6.89 (m, 1H), 3.96 (app m, 2H), 2.54 (s, 3H), 1.63 (s, 9H). LCMS: Purity 94%, MS (m/e) 274 (M+H)$^+$.

2-((1H-Pyrazol-4-yl)methyl)-6-methylpyridine dihydrochloride

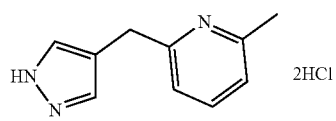

$^1$H NMR (400 MHz, DMSO-d$_6$) δ 8.34 (t, J=7.9 Hz, 1H), 8.23-7.81 (br s, 2H), 7.75 (s, 1H), 7.72 (dt, J=7.9, 0.9 Hz, 1H), 7.66 (dt, J=7.9, 0.9 Hz, 1H), 4.32 (s, 2H), 2.77 (s, 3H). LCMS: Purity 94%, MS (m/e) 174 (M−2HCl+H)$^+$.

tert-Butyl 4-((6-fluoropyridin-2-yl)methyl)-1H-pyrazole-1-carboxylate

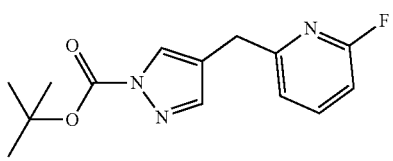 [SMILES: CC(C)(C)OC(=O)n1cc(Cc2cccc(F)n2)cn1]

$^1$H NMR (400 MHz, Chloroform-d) δ 7.94 (s, 1H), 7.69 (q, J=7.9 Hz, 1H), 7.61 (s, 1H), 7.00 (dd, J=7.4, 2.4 Hz, 1H), 6.77 (dd, J=8.2, 2.8 Hz, 1H), 3.92 (s, 2H), 1.62 (s, 9H). LCMS: Purity 98%, MS (m/e) 278 (M+H)$^+$.

2-((1H-Pyrazol-4-yl)methyl)-6-fluoropyridine hydrochloride

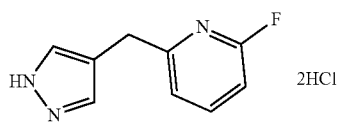

$^1$H NMR (400 MHz, DMSO-d$_6$) δ 10.24 (br s, 2H), 7.89 (td, J=8.4, 7.4 Hz, 1H), 7.76 (s, 2H), 7.20 (ddd, J=7.4, 2.7, 0.7 Hz, 1H), 6.98 (ddd, J=8.2, 2.8, 0.7 Hz, 1H), 3.91 (s, 2H). LCMS: Purity 98%, MS (m/e) 178 (M−HCl+H)$^+$.

tert-Butyl
4-(pyridazin-3-ylmethyl)-1H-pyrazole-1-carboxylate

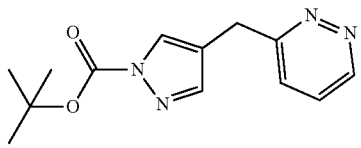 [SMILES: CC(C)(C)OC(=O)n1cc(Cc2cccnn2)cn1]

LC/MS: Purity 92%, MS (m/e) 261 (M+H)$^+$.

3-((1H-Pyrazol-4-yl)methyl)pyridazine dihydrochloride

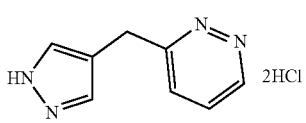 [SMILES: c1cnnc(Cc2cn[nH]c2)c1]

LC/MS: Purity 92%, MS (m/e) 161 (M−2HCl+H)$^+$.

105 tert-Butyl 4-((6-(trifluoromethyl)pyridin-2-yl)methyl)-1H-pyrazole-1-carboxylate

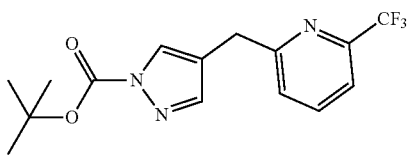 [SMILES: CC(C)(C)OC(=O)n1cc(Cc2cccc(C(F)(F)F)n2)cn1]

¹H NMR (400 MHz, Chloroform-d) δ7.99 (d, J=0.9 Hz, 1H), 7.78 (t, J=7.5 Hz, 1H), 7.66 (s, 1H), 7.54 (d, J=7.8 Hz, 1H), 7.32 (d, J=7.9 Hz, 1H), 4.08 (s, 2H), 1.63 (s, 9H). LCMS: Purity 96%, MS (m/e) 328 (M+H)⁺.

2-((1H-Pyrazol-4-yl)methyl)-6-(trifluoromethyl)pyridine

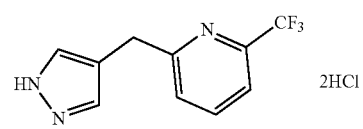 [SMILES: FC(F)(F)c1cccc(Cc2cn[nH]c2)n1]

¹H NMR (400 MHz, DMSO-d₆) δ 12.11 (br, 2H), 8.00 (tt, J=7.8, 0.9 Hz, 1H), 7.83 (s, 2H), 7.72 (d, J=8.0, 2.4 Hz, 1H), 7.58 (dd, J=8.0, 2.4 Hz, 1H), 4.06 (s, 2H). ¹⁹F NMR (376 MHz, DMSO-d₆) δ −66.47. LCMS: Purity 96%, MS (m/e) 228 (M+H)⁺.

tert-Butyl 4-(pyridin-3-ylmethyl)-1H-pyrazole-1-carboxylate

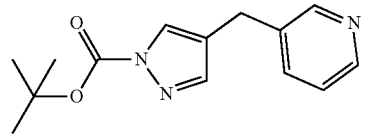 [SMILES: CC(C)(C)OC(=O)n1cc(Cc2cccnc2)cn1]

LC/MS: Purity 95%, MS (m/e) 260 (M+H)⁺.

2-((1H-Pyrazol-4-yl)methyl)pyridine dihydrochloride

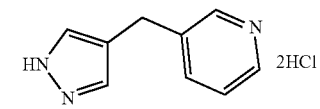 [SMILES: c1cncc(Cc2cn[nH]c2)c1]

¹H NMR (400 MHz, DMSO-d₆) δ 10.5 (br s, 3H), 8.88-8.83 (m, 1H), 8.79 (d, J=5.2 Hz, 1H), 8.47 (ddd, J=8.1, 2.0, 1.3 Hz, 1H), 8.00 (ddd, J=8.1, 5.7, 0.7 Hz, 1H), 7.74 (s, 2H), 4.06 (2H). LCMS: Purity 95%, MS (m/e) 160 (M−2HCl+H)⁺.

106 tert-Butyl 4-(pyridin-4-ylmethyl)-1H-pyrazole-1-carboxylate

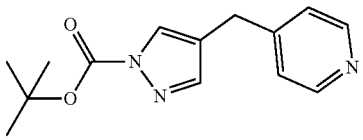 [SMILES: CC(C)(C)OC(=O)n1cc(Cc2ccncc2)cn1]

LC/MS: Purity 97%, MS (m/e) 260(M+H)⁺.

4-((1H-pyrazol-4-yl)methyl)pyridine dihydrochloride

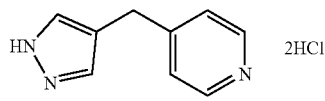 [SMILES: c1cc(Cc2cn[nH]c2)ccn1]

¹H NMR (400 MHz, Methanol-d₄) δ 8.82-8.72 (m, 2H), 8.16 (s, 2H), 8.04-7.98 (m, 2H), 4.36 (s, 2H). LCMS: Purity 98%, MS (m/e) 160 (M−2HCl+H)⁺.

Example 7

Scheme 11 provides a method for making 4-((6-methylpyridin-3-yl)oxy)picolinic acid.

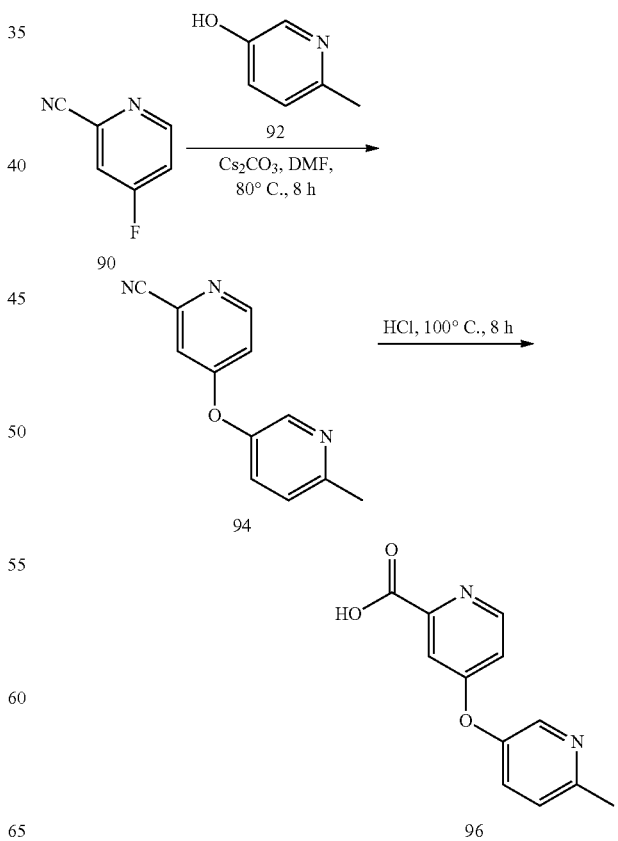

With reference to Scheme 11, cesium carbonate (1.1 eq) is added to a solution of 4-fluoropicolinonitrile 90 (1.0 eq) and 6-methylpyridin-3-ol 92 (1.05 eq) in dimethylformamide. The reaction is heated to 80° C. for 8 hours and cooled. The reaction is poured into ice-water and 4-((6-methylpyridin-3-yl)oxy)picolinonitrile 94 is isolated.

A mixture of 4-((6-methylpyridin-3-yl)oxy)picolinonitrile 94 in hydrochloric acid (6M) is heated to 100° C. for 8 hours. The reaction is cooled to room temperature and 4-((6-methylpyridin-3-yl)oxy)picolinic acid 96 is isolated.

Example 8

This example concerns a method for making (S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-3-yl)oxy)picolinamide according to Scheme 12.

Scheme 12

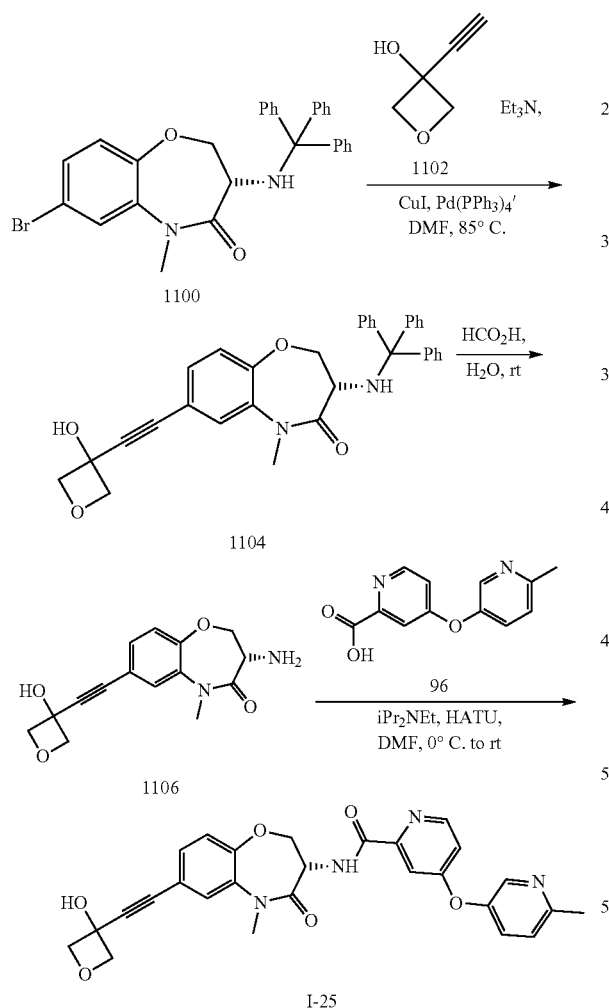

Dimethylformamide (80 mL) was added to a mixture of bromooxobenzoxazapine 1100 (8.36 g, 16.3 mmol, 1.0 eq) and copper iodide (0.31 g, 1.6 mmol, 0.1 eq). The mixture was degassed by bubbling argon through for five minutes. Triethylamine (11.4 mL, 81.6 mmol, 5.0 eq) was added followed by the hydroxyethynyloxetane 1102 (3.20 g, 32.7 mmol, 2.0 eq) and tetrakis(triphenylphosphine)palladium (0.94 g, 0.8 mmol, 0.05 eq). The resulting brown solution was heated to 80° C. for 4 hours. The reaction was cooled and partitioned between EtOAc (200 mL) and water (200 mL). The organics were washed with brine (150 mL), water (200 mL) and brine (150 mL), dried (Na$_2$SO$_4$) and concentrated under reduced pressure. MPLC (10 to 70% EtOAc-hexane) yielded compound 1104 (6.18 g, 72%) as a yellow solid. 1H nmr (400 MHz, CD3Cl) δ 7.41-7.39 (6H, m, 6H of C(C6H5)3), 7.25-7.15 (10H, m, 9H of C(C6H5)3, oxobenzoxazapineH-8), 7.00-6.98 (2H, m, oxobenzoxazapineH-6, H-9), 4.94 (2H, d, J 7.0 Hz, 2H of oxetaneH-2, H-4), 4.80 (2H, d, J 7.5 Hz, 2H of oxetaneH-2, H-4), 4.50 (1H, dd, J 10.0, 7.0 Hz, 1H of oxobenzoxazapineH-2), 4.39 (1H, dd, J 11.5, 10.0 Hz, 1H of oxobenzoxazapineH-2), 3.59-3.52 (1H, m, oxobenzoxazapineH-3), 3.29 (1H, d, J 9.0 Hz, NH), 2.89 (3H, s, NCH3).

Formic acid (50 mL) was added to the trityl protected amine 1104 (7.49 g, 14.1 mmol, 1 eq) and the mixture stirred at room temperature for 4 hours. Water (50 mL) was added and the reaction stirred at room temperature for 15 hours. The reaction was concentrated to remove some of the formic acid before diluting with water (100 mL). The organics were extracted with EtOAc (50 mL) and set aside. The aqueous phase was neutralized by the addition of NaOH (5M, portionwise to approximately 40 mL). The organics were extracted with EtOAc (4×150 mL). The combined neutralized organics were dried (Na2SO4) and concentrated under reduced pressure to obtain (S)-3-amino-7-((3-hydroxyoxetan-3-yl)ethynyl)-5-methyl-2,3-dihydrobenzo[b][1,4]oxazepin-4(5H)-one 1106 (3.78 g, 93%) as a yellow solid which was used without further purification. 1H nmr (400 MHz, D6-DMSO) δ 7.51 (1H, d, J 2.0 Hz, oxobenzoxazapineH-6), 7.29 (1H, dd, J 8.0, 2.0 Hz, oxobenzoxazapineH-8), 7.14 (1H, d, J 8.0 Hz, oxobenoxazapineH-9), 4.74 (2H, d, J 7.0 Hz, 2H of oxetaneH-2, H-4), 4.58 (2H, d, J 7.0 Hz, 2H of oxetaneH-2, H-4), 4.25 (1H, dd, J 10.0, 7.5 Hz, 1H of oxobenzoxazapineH-2), 4.01 (1H, dd, J 11.5, 10.0 Hz, 1H of oxobenzoxazapineH-2), 3.59 (1H, dd, J 11.5, 7.5 Hz, oxobenzoxazapineH-3), 3.28 (3H, s, NCH3); 13C nmr (100 MHz, D6-DMSO) δ 173.7, 150.7, 137.7, 130.2, 126.2, 126.6, 123.3, 119.1, 90.9, 84.5, 83.7, 80.3, 66.3, 51.1, 35.1; m/z: 289 [M+H]$^+$.

A solution of the aminooxobenzoxazapine 1106 (1.0 eq) in dimethylformamide is degassed by bubbling nitrogen through for five minutes. 4-((6-methylpyridin-3-yl)oxy)picolinic acid 96 (1.0 eq) is added and the solution cooled to 0° C. before adding diisopropylethylamine (2.5 eq). HATU (1.1 eq) is added portionwise and the reaction stirred at 0° C. for 1 hour and room temperature for 15 hours. The reaction is poured into ice-water and the product is isolated.

Example 9

Exemplary compounds and characterization data are provided below.

(S)-3-amino-7-(3-hydroxy-3-methylbut-1-yn-1-yl)-5-methyl-2,3-dihydrobenzo[b][1,4]oxazepin-4(5H)-one

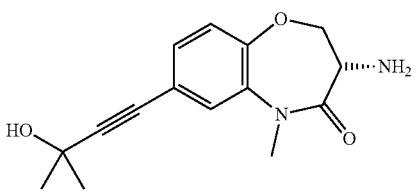

¹H nmr (400 MHz, CDCl₃) δ 7.24 (1H, d, J 2.0 Hz, oxobenzoxazapineH-6), 7.22 (1H, dd, J 8.0, 2.0 Hz, oxobenzoxazapineH-8), 7.06 (1H, d, J 8.0 Hz, oxobenzoxazapineH-9), 4.41 (1H, dd, J 10.0, 7.5 Hz, 1H of oxobenzoxazapineH-2), 4.12 (1H, dd, J 11.5, 10.0 Hz, 1H of oxobenzoxazapineH-2), 3.72 (1H, dd, J 11.5, 7.5 Hz, oxobenzoxazapineH-3); m/z: 275 [M+H]⁺ (found [M+H]⁺, 275.1390, C₁₅H₁₈N₂O₃ requires [M+H]⁺ 275.1404).

(S)-4-((6-Fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide (I-1)

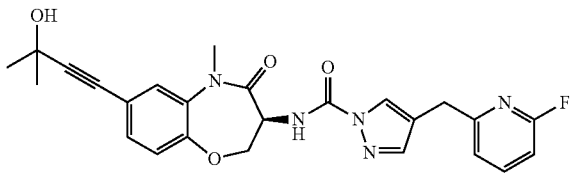 [SMILES: CN1C(=O)[C@@H](NC(=O)n2cc(Cc3cccc(F)n3)cn2)COc2ccc(C#CC(C)(C)O)cc21]

Route 3. ¹H NMR (400 MHz, Chloroform-d) δ 7.99-7.93 (m, 2H), 7.68 (td, J=8.2, 7.3 Hz, 1H), 7.55 (d, J=0.8 Hz, 1H), 7.32-7.23 (m, 2H), 7.11 (d, J=8.8 Hz, 1H), 7.02-6.95 (m, 1H), 6.76 (dd, J=8.2, 2.8 Hz, 1H), 4.86 (dt, J=11.3, 7.2 Hz, 1H), 4.68 (dd, J=9.8, 7.3 Hz, 1H), 4.29 (dd, J=11.3, 9.8 Hz, 1H), 3.91 (s, 2H), 3.41 (s, 3H), 1.61 (s, 6H). ¹⁹F NMR (376 MHz, Chloroform-d) δ –66.98 (d, J=8.2 Hz). LC/MS: Purity 98%, MS (m/e) 478 (M+H)⁺.

(S)—N-(7-(3-Hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)-1H-pyrazole-1-carboxamide (I-2)

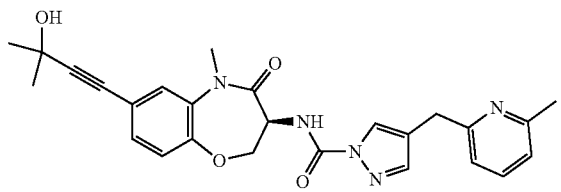 [SMILES: Cc1cccc(Cc2cnn(C(=O)N[C@H]3COc4ccc(C#CC(C)(C)O)cc4N(C)C3=O)c2)n1]

Route 3. ¹H NMR (400 MHz, Chloroform-d) 67.95 (d, J=7.2 Hz, 1H), 7.92 (d, J=0.9 Hz, 1H), 7.54 (d, J=0.8 Hz, 1H), 7.46 (t, J=7.7 Hz, 1H), 7.30-7.23 (m, 2H), 7.14-7.07 (m, 1H), 6.98 (d, J=7.7 Hz, 1H), 6.89 (d, J=7.7 Hz, 1H), 5.28 (s, 1H), 4.86 (dt, J=11.3, 7.3 Hz, 1H), 4.67 (dd, J=9.8, 7.3 Hz, 1H), 4.29 (dd, J=11.3, 9.8 Hz, 1H), 3.93 (s, 2H), 3.40 (s, 3H), 2.52 (s, 3H), 1.61 (s, 6H). LC/MS: Purity 98%, MS (m/e) 474 (M+H)⁺.

(S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-3-yl)oxy)picolinamide (I-3)

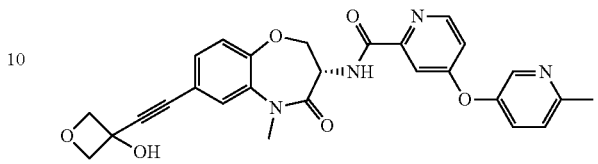

¹H nmr (400 MHz, CDCl₃) δ 8.87 (1H, d, J 7.5 Hz, NH), 8.47 (1H, d, J 5.5 Hz, pyH-6), 8.33 (1H, d, J 2.5 Hz, Me-pyH-2), 7.58 (1H, d, J 2.5 Hz, pyH-3), 7.34-7.26 (3H, m, oxobenzoxazapineH-6, H-8, Me-pyH-4), 7.23 (1H, d, J 8.5 Hz, Me-pyH-5), 7.15 (1H, d, J 9.0 Hz, oxobenzoxazapineH-9), 6.70 (1H, dd, J 5.5, 2.5 Hz, pyH-5), 5.02 (1H, dt, J 11.0, 7.5 Hz, oxobenzoxazapineH-3), 4.93 (2H, d, J 5.0 Hz, 2H of oxetaneH-2, H-4), 4.80 (2H, d, J 6.5 Hz, 2H of oxetaneH-2, H-4), 4.71 (1H, dd, J 9.5, 7.5 Hz, 1H of oxobenzoxazapineH-2), 4.31 (1H, t, J 10.5 Hz, 1H of oxobenzoxazapineH-2), 3.42 (3H, s, NCH₃), 2.59 (3H, s, pyCH₃); m/z: 501 [M+H]⁺ (found [M+H]⁺, 501.1776, C₂₇H₂₄N₄O₆ requires [M+H]⁺ 501.1769).

(S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)oxy)picolinamide (I-4)

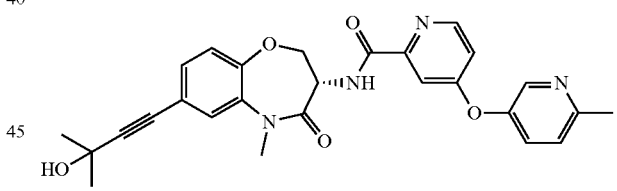

¹H nmr (400 MHz, CDCl₃) δ 8.87 (1H, d, J 7.5 Hz, NH), 8.47 (1H, d, J 5.5 Hz, pyH-6), 8.33 (1H, d, J 2.5 Hz, Me-pyH-2), 7.58 (1H, d, J 2.5 Hz, pyH-3), 7.32 (1H, dd, J 8.5, 3.0 Hz, Me-pyH-4), 7.29-7.26 (2H, m, oxobenzoxazapineH-6, H-8), 7.22 (1H, d, J 8.5 Hz, Me-pyH-5), 7.12 (1H, d, J 9.0 Hz, oxobenzoxazapineH-9), 6.97 (1H, dd, J 5.5, 2.5 Hz, pyH-5), 5.02 (1H, dt, J 11.0, 7.5 Hz, oxobenzoxazapineH-3), 4.71 (1H, dd, J 9.5, 7.5 Hz, 1H of oxobenzoxazapineH-2), 4.30 (1H, dd, J 11.0, 9.5 Hz, 1H of oxobenzoxazapineH-2), 3.43 (3H, s, NCH₃), 2.59 (3H, s, pyCH₃), 1.63 (6H, s, C(CH₃)₂OH); m/z: 487 [M+H]⁺, 469 [M+H–H₂O]⁺ (found [M+H]⁺, 487.1991, C₂₇H₂₆N₄O₅ requires [M+H]⁺ 487.1976).

111

(S)-4-((6-fluoropyridin-3-yl)oxy)-N-(7-((3-hydroxyoxetan-3-yl)ethynyl)-5-methyl-4-oxo-2,3,4,5-tetrahydrobenzo[b][1,4]oxazepin-3-yl)picolinamide (I-5)

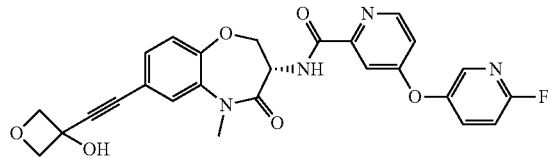 [SMILES: CN1C(=O)[C@@H](NC(=O)c2cc(Oc3ccc(F)nc3)ccn2)COc2ccc(C#CC3(O)COC3)cc21]

$^1$H nmr (400 MHz, CDCl$_3$) δ 8.87 (1H, d, J 7.5 Hz, NH), 8.50 (1H, d, J 5.5 Hz, pyH-6), 8.05 (1H, dd, J 2.5, 1.0 Hz, F-pyH-2), 7.58 (1H, d, J 2.5 Hz, pyH-3), 7.54 (1H, ddd, J 9.0, 6.0, 3.0 Hz, F-pyH-4), 7.33-7.30 (2H, m, oxobenzoxazapineH-6, H-8), 7.16 (1H, d, J 9.0 Hz, oxobenzoxazapineH-9), 7.02 (1H, dd, J 9.0, 3.5 Hz, F-pyH-5), 6.98 (1H, dd, J 5.5, 2.5 Hz, pyH-5), 5.03 (1H, dt, J 11.5, 7.5 Hz, oxobenzoxazapineH-3), 4.94-4.92 (2H, m, 2H of oxetaneH-2, H-4), 4.79 (2H, d, J 7.0 Hz, 2H of oxetaneH-2, H-4), 4.71 (1H, dd, J 10.0, 7.5 Hz, 1H of oxobenzoxazapineH-2), 4.31 (1H, dd, J 11.5, 10.0 Hz, 1H of oxobenzoxazapineH-2), 3.43 (3H, s, NCH3), 2.95 (1H, s, OH); $^{19}$F nmr (380 MHz, CDCl$_3$) δ −70.4; m/z: 505 [M+H]$^+$ (found [M+H]$^+$, 505.1516, C$_{26}$H$_{21}$FN$_4$O$_6$ requires [M+H]$^+$ 505.1518).

(S)-4-((6-fluoropyridin-3-yl)oxy)-N-(7-(3-hydroxy-3-methylbut-1-yn-1-yl)-5-methyl-4-oxo-2,3,4,5-tetrahydrobenzo[b][1,4]oxazepin-3-yl)picolinamide (I-6)

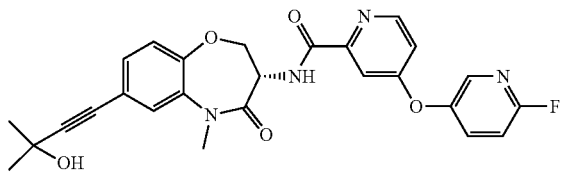 [SMILES: CN1C(=O)[C@@H](NC(=O)c2cc(Oc3ccc(F)nc3)ccn2)COc2ccc(C#CC(C)(C)O)cc21]

$^1$H nmr (400 MHz, CDCl$_3$) δ 8.86 (1H, d, J 7.5 Hz, NH), 8.50 (1H, d, J 5.5 Hz, pyH-3), 8.05 (1H, dd, J 3.0, 1.0 Hz, F-pyH-2), 7.58 (1H, d, J 2.5 Hz, pyH-3), 7.53 (1H, ddd, J 9.0, 6.0, 3.0 Hz, F-pyH-4), 7.29-7.26 (2H, m, oxobenzoxazapineH-6, H-8), 7.13 (1H, d, J 9.0 Hz, oxobenzoxazapineH-9), 7.02 (1H, dd, J 9.0, 3.0 Hz, F-pyH-5), 6.98 (1H, dd, J 5.5, 2.5 Hz, pyH-5), 5.01 (1H, dt, J 11.5, 7.5 Hz, oxobenzoxazapineH-3), 4.71 (1H, dd, J 10.0, 7.5 Hz, 1H of oxobenzoxazapineH-2), 4.29 (1H, dd, J 11.5, 10.0 Hz, 1H of oxobenzoxazapineH-2), 3.43 (3H, s, NCH$_3$), 1.62 (6H, s, C(CH$_3$)$_2$OH); $^{19}$F nmr (380 MHz, CDCl$_3$) δ −70.4; m/z: 491 [M+H]$^+$, 473 [M+H−H$_2$O]$^+$ (found [M+H]$^+$, 491.1722, C$_{26}$H$_{23}$FN$_4$O$_5$ requires [M+H]$^+$ 491.1725).

112

(S)-4-((6-fluoropyridin-2-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide (I-7)

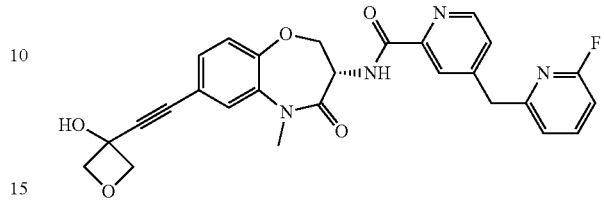

$^1$H nmr (400 MHz, CDCl$_3$) δ 8.87 (1H, d, J 7.5 Hz, NH), 8.51 (1H, dd, J 5.0, 1.0 Hz, pyH-6), 7.95 (1H, d, J 1.0 Hz, pyH-3), 7.70 (1H, m, F-pyH-4), 7.36 (1H, dd, J 5.0, 2.0 Hz, pyH-5), 7.31-7.28 (2H, m, oxobenzoxazapineH-6, H-8), 7.15 (1H, d, J 9.0 Hz, oxobenzoxazapineH-9), 7.00 (1H, dd, J 7.5, 2.0 Hz, F-pyH-3 or H-5), 6.79 (1H, dd, J 8.0, 2.5 Hz, F-pyH-3 or H-5), 5.05 (1H, dt, J 11.5, 7.5 Hz, oxobenzoxazapineH-3), 4.92 (2H, dd, J 6.5, 4.0 Hz, 2H of oxetaneH-2, H-4), 4.79 (2H, ddd, J 7.0, 2.0, 1.0 Hz, 2H of oxetaneH-2, H-4), 4.71 (1H, dd, J 9.5, 7.5 Hz, 1H of oxobenzoxazapineH-2), 4.30 (1H, dd, J 11.0, 9.5 Hz, 1H of oxobenzoxazapineH-2), 4.11 (2H, s, pyCH$_2$py), 3.41 (3H, s, NCH$_3$); $^{19}$F nmr (380 MHz, CDCl$_3$) δ −66.6 (d, J 8.0 Hz); m/z: 503 [M+H]$^+$ (found [M+H]$^+$, 503.1724, C$_{27}$H$_{23}$FN$_4$O requires [M+H]$^+$ 503.1725).

(S)—N-(7-(3-Hydroxy-3-methylbut-1-yn-1-yl)-5-methyl-4-oxo-2,3,4,5-tetrahydrobenzo[b][1,4]oxazepin-3-yl)-4-(pyridin-2-ylmethyl)-1H-pyrazole-1-carboxamide (I-8)

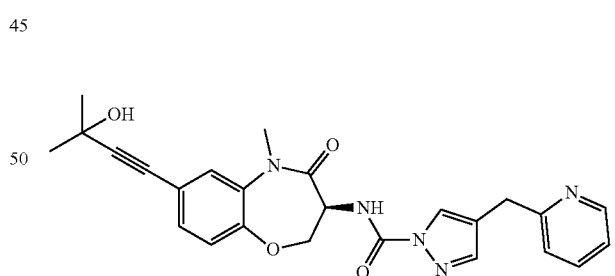

Route 3. $^1$H NMR (400 MHz, Chloroform-d) δ 8.54 (d, J=4.9 Hz, 1H), 7.97 (d, J=7.0 Hz, 1H), 7.96 (s, 1H), 7.60 (td, J=7.7, 1.9 Hz, 1H), 7.55 (s, 1H), 7.27 (d, J=9.5 Hz, 1H), 7.25 (s, 1H), 7.13 (dt, J=9.0, 5.0 Hz, 3H), 4.87 (dt, J=11.2, 7.2 Hz, 1H), 4.68 (dd, J=9.8, 7.3 Hz, 1H), 4.30 (dd, J=11.3, 9.8 Hz, 1H), 3.99 (s, 2H), 3.41 (s, 3H), 2.10 (s, 1H), 1.62 (s, 6H). LC/MS: Purity 97%, MS (m/e) 460 (M+H)$^+$.

113

(S)—N-(7-(3-Hydroxy-3-methylbut-1-yn-1-yl)-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide (I-9)

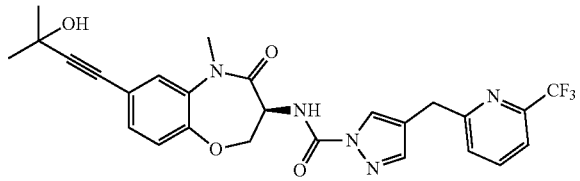

Route 3. $^1$H NMR (400 MHz, Methylene Chloride-$d_2$) δ 8.00 (q, J=0.8 Hz, 1H), 7.91 (d, J=7.1 Hz, 1H), 7.82 (td, J=7.8, 0.7 Hz, 1H), 7.62 (d, J=0.9 Hz, 1H), 7.58-7.53 (m, 1H), 7.37 (d, J=7.9 Hz, 1H), 7.33 (d, J=1.9 Hz, 1H), 7.30 (dd, J=8.2, 2.0 Hz, 1H), 7.16 (d, J=8.3 Hz, 1H), 4.86 (dt, J=11.2, 7.2 Hz, 1H), 4.71 (dd, J=9.8, 7.3 Hz, 1H), 4.31 (dd, J=11.3, 9.8 Hz, 1H), 4.08 (s, 2H), 3.41 (s, 3H), 1.60 (s, 6H). $^{19}$F NMR (376 MHz, Methylene Chloride-$d_2$) δ −68.40. LC/MS: Purity 95%, MS (m/e) 528 (M+H)$^+$.

(S)—N-(7-((3-hydroxyoxetan-3-yl)ethynyl)-5-methyl-4-oxo-2,3,4,5-tetrahydrobenzo[b][1,4]oxazepin-3-yl)-4-((6-hydroxypyridin-2-yl)methyl)picolinamide (I-10)

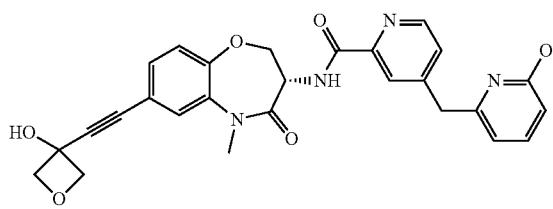 [SMILES: CN1C(=O)[C@@H](NC(=O)c2cc(Cc3cccc(F)n3)ccn2)COc2ccc(C#CC3(O)COC3)cc21]

$^1$H nmr (400 MHz, CD$_3$OD) δ 8.54 (1H, d, J 5.0 Hz, pyH-3), 7.51 (1H, d, J 2.0 Hz, oxobenzoxazapineH-6), 7.49 (1H, dd, J 9.0, 7.0 Hz, (OH)-pyH-4), 7.42 (1H, dd, J 5.0, 2.0 Hz, pyH-5), 7.37 (1H, dd, J 8.0, 2.0 Hz, oxobenzoxazapineH-8), 7.93 (1H, br d, J 1.0 Hz, pyH-3), 7.20 (1H, d, J 8.5 Hz, oxobenzoxazapineH-9), 6.40 (1H, d, J 9.0 Hz, (OH)-pyH-3 or H-5), 6.20 (1H, d, J 7.0 Hz, (OH)-pyH-3 or H-5), 5.01 (1H, dd, J 11.5, 7.5 Hz, oxobenzoxazapineH-3), 4.89-4.87 (2H, m, 2H of oxetaneH-2, H-4), 4.71 (2H, d, J 6.5 Hz, 2H of oxetaneH-2, H-4), 4.63 (1H, dd, J 9.5, 7.5 Hz, 1H of oxobenzoxazapineH-2), 4.41 (1H, dd, J 11.5, 10.0 Hz, 1H of oxobenzoxazapineH-2), 3.98 (2H, s, pyCH$_2$(OH)-py), 3.41 (3H, s, NCH$_3$); m/z: 501 [M+H]+(found [M+H]$^+$, 501.1776, C$_{27}$H$_{24}$N$_4$O$_6$ requires [M+H]$^+$ 501.1769).

114

(S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)picolinamide (I-11)

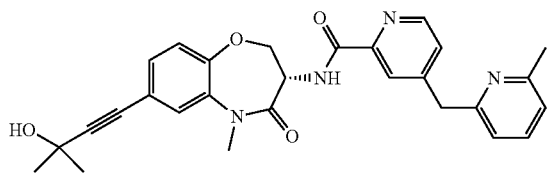 [SMILES: Cc1cccc(Cc2ccnc(C(=O)N[C@H]3COc4ccc(C#CC(C)(C)O)cc4N(C)C3=O)c2)n1]

$^1$H nmr (400 MHz, CDCl$_3$) δ 8.86 (1H, d, J 7.5 Hz, NH), 8.49 (1H, d, J 5.0 Hz, pyH-6), 7.97 (1H, d, J 1.0 Hz, pyH-3), 7.48 (1H, t, J 8.0 Hz, Me-pyH-4), 7.33 (1H, dd, J 5.0, 1.5 Hz, pyH-5), 7.29-7.26 (2H, m, oxobenzoxazapineH-6, H-8), 7.12 (1H, d, J 9.0 Hz, oxobenzoxazapineH-9), 7.01 (1H, d, J 8.0 Hz, Me-pyH-3 or H-5), 6.88 (1H, d, J 8.0 Hz, Me-pyH-3 or H-5), 5.05 (1H, dt, J 11.5, 7.5 Hz, oxobenzoxazapineH-3), 4.71 (1H, dd, J 10.0, 7.5 Hz, 1H of oxobenzoxazapineH-2), 4.29 (1H, dd, J 11.0, 10.0 Hz, 1H of oxobenzoxazapineH-2), 4.16 (2H, s, pyCH$_2$py), 3.42 (3H, s, NCH$_3$), 2.53 (3H, s, pyCH$_3$), 1.62 (6H, s, C(CH$_3$)$_2$OH); m/z: 485 [M+H]$^+$, 467 [M+H−H$_2$O]$^+$ (found [M+H]$^+$, 485.2182, C$_{28}$H$_{28}$N$_4$O$_4$ requires [M+H]$^+$ 485.2183).

(S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-2-yl)methyl)picolinamide (I-12)

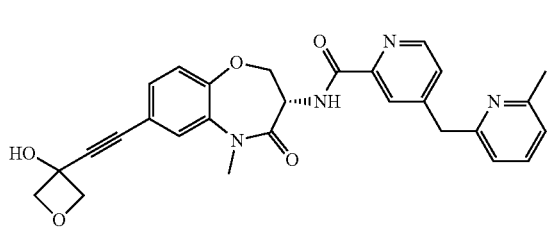 [SMILES: Cc1cccc(Cc2ccnc(C(=O)N[C@H]3COc4ccc(C#CC5(O)COC5)cc4N(C)C3=O)c2)n1]

$^1$H nmr (400 MHz, CDCl$_3$) δ 8.86 (1H, d, J 7.5 Hz, NH), 8.49 (1H, d, J Hz, pyH-6), 7.96 (1H, br d, J 1.0 Hz, pyH-3), 7.49 (1H, t, J 7.5 Hz, MepyH-4), 7.33 (1H, dd, J 5.0, 2.0 Hz, pyH-5), 7.31-7.29 (2H, m, oxobenzoxazapineH-6, H-8), 7.15 (1H, d, J 9.0 Hz, oxobenzoxazapineH-9), 7.01 (1H, d, J 7.5 Hz, MepyH-3 or H-5), 6.89 (1H, d, J 7.5 Hz, MepyH-3 or H-5), 5.06 (1H, dt, J 11.0, 7.5 Hz, oxobenzoxazapineH-3), 4.94-4.92 (2H, m, 2H of oxetaneH-2, H-4), 4.80 (2H, d, J 7.0 Hz, 2H of oxetaneH-2, H-4), 4.71 (1H, dd, J 9.5, 7.5 Hz, 1H of oxobenzoxazapineH-2), 4.31 (1H, dd, J 11.0, 9.5 Hz, 1H of oxobenzoxazapineH-2), 4.16 (2H, s, pyCH$_2$py), 3.42 (3H, s, NCH$_3$), 2.53 (3H, s, pyCH$_3$); m/z: 499 [M+H]$^+$ (found [M+H]$^+$, 499.1972, C$_{28}$H$_{26}$N$_4$O$_5$ requires [M+H]$^+$ 499.1976).

(S)-4-((6-fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide (I-13)

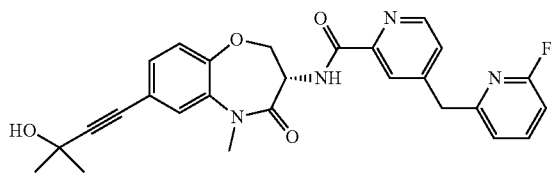 [SMILES: CN1C(=O)[C@@H](NC(=O)c2cc(Cc3cccc(F)n3)ccn2)COc2ccc(C#CC(C)(C)O)cc21]

¹H nmr (400 MHz, CDCl₃) δ 8.86 (1H, d, J 7.0 Hz, NH), 8.52 (1H, d, J 5.0 Hz, pyH-6), 7.96 (1H, d, J 1.0 Hz, pyH-3), 7.70 (1H, q, J 8.0 Hz, F-pyH-4), 7.36 (1H, dd, J 5.0, 3.0 Hz, pyH-5), 7.29-7.26 (2H, m, oxobenzoxazapineH-6, H-8), 7.13 (1H, d, J 9.0 Hz, oxobenzoxazapineH-9), 7.00 (1H, dd, J 7.5, 2.5 Hz, F-pyH-3 or H-5), 6.80 (1H, dd, J 8.0, 3.0 Hz, F-pyH-3 or H-5), 5.04 (1H, dt, J 11.0, 7.5 Hz, oxobenzoxazapineH-3), 4.71 (1H, dd, J 9.5, 7.5 Hz, 1H of oxobenzoxazapineH-2), 4.29 (1H, dd, J 11.0, 9.5 Hz, 1H of oxobenzoxazapineH-2), 4.13, 10 (2H, 2d AB system, J 11.0 Hz, pyCH₂py), 3.42 (3H, s, NCH₃), 1.62 (6H, s, C(CH₃)₂OH); m/z: 489 [M+H]⁺ (found [M+H]⁺, 489.1944, C₂₇H₂₅FN₄O₄ requires [M+H]⁺ 489.1933).

(S)—N-(7-(3-Hydroxy-3-methylbut-1-yn-1-yl)-5-methyl-4-oxo-2,3,4,5-tetrahydrobenzo[b][1,4]oxazepin-3-yl)-4-(pyridin-3-ylmethyl)-1H-pyrazole-1-carboxamide (I-14)

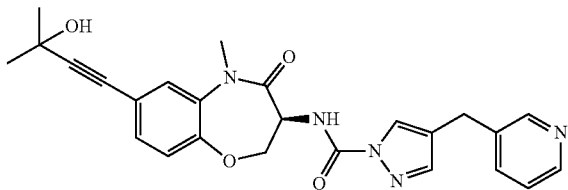

Route 3. ¹H NMR (400 MHz, Methylene Chloride-d₂) δ 8.53-8.42 (app m, 2H), 7.95-7.87 (m, 2H), 7.56-7.49 (m, 2H), 7.32 (d, J=1.9 Hz, 1H), 7.31-7.22 (m, 2H), 7.14 (d, J=8.2 Hz, 1H), 4.86 (dt, J=11.2, 7.2 Hz, 1H), 4.70 (dd, J=9.8, 7.3 Hz, 1H), 4.31 (dd, J=11.2, 9.8 Hz, 1H), 3.84 (s, 2H), 3.40 (s, 3H), 1.60 (s, 6H). LC/MS: Purity 98%, MS (m/e) 442 (M−H₂O+H)⁺.

(S)—N-(7-(3-Hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)methyl)-1H-pyrazole-1-carboxamide (I-15)

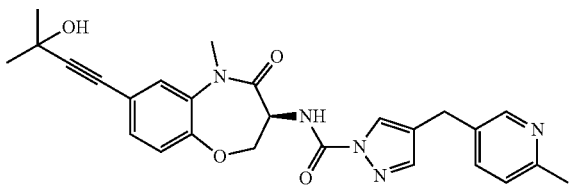 [SMILES: Cc1ccc(Cc2cnn(C(=O)N[C@H]3COc4ccc(C#CC(C)(C)O)cc4N(C)C3=O)c2)cn1]

¹H NMR (400 MHz, Methylene Chloride-d₂) δ 8.34 (d, J=2.4 Hz, 1H), 7.89 (d, J=7.1 Hz, 1H), 7.87 (q, J=0.9 Hz, 1H), 7.50 (d, J=0.9 Hz, 1H), 7.39 (dd, J=8.0, 2.4 Hz, 1H), 7.33 (dd, J=2.0, 0.4 Hz, 1H), 7.30 (dd, J=8.2, 2.0 Hz, 1H), 7.16 (dd, J=8.2, 0.4 Hz, 1H), 7.09 (d, J=7.9 Hz, 1H), 4.86 (dt, J=11.2, 7.2 Hz, 1H), 4.70 (dd, J=9.8, 7.3 Hz, 1H), 4.31 (dd, J=11.2, 9.8 Hz, 1H), 3.79 (s, 2H), 3.41 (s, 3H), 2.49 (s, 3H), 1.60 (s, 6H). LCMS: Purity 97%, MS (m/e) 474 (M+H)⁺.

(S)-4-((6-Fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide (I-16)

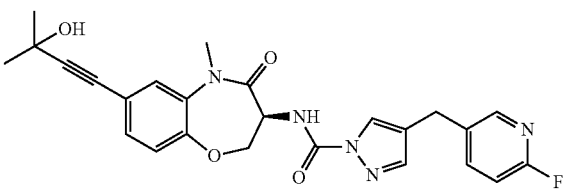 [SMILES: CN1C(=O)[C@@H](NC(=O)n2cc(Cc3ccc(F)nc3)cn2)COc2ccc(C#CC(C)(C)O)cc21]

¹H NMR (400 MHz, Chloroform-d) δ 8.08-8.03 (m, 1H), 7.97 (d, J=7.2 Hz, 1H), 7.87 (q, J=0.9 Hz, 1H), 7.60-7.50 (m, 1H), 7.45 (d, J=0.9 Hz, 1H), 7.31-7.24 (m, 2H), 7.12 (d, J=8.7 Hz, 1H), 6.86 (ddd, J=8.4, 3.0, 0.6 Hz, 1H), 4.86 (dt, J=11.3, 7.2 Hz, 1H), 4.68 (dd, J=9.8, 7.3 Hz, 1H), 4.30 (dd, J=11.3, 9.8 Hz, 1H), 3.80 (s, 2H), 3.41 (s, 3H), 2.02 (s, 1H), 1.61 (s, 6H). ¹⁹F NMR (376 MHz, Chloroform-d) δ −70.88 (d, J=5.9 Hz). LCMS: Purity 96%, MS (m/e) 478 (M+H)⁺.

(S)—N-(7-(3-Hydroxy-3-methylbut-1-yn-1-yl)-5-methyl-4-oxo-2,3,4,5-tetrahydrobenzo[b][1,4]oxazepin-3-yl)-4-(pyridazin-3-ylmethyl)-1H-pyrazole-1-carboxamide (I-17)

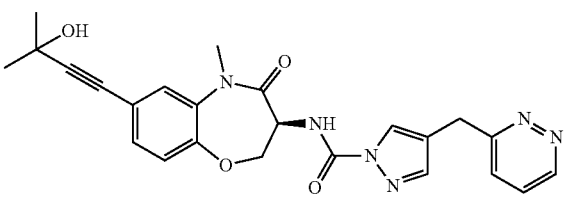 [SMILES: CN1C(=O)[C@@H](NC(=O)n2cc(Cc3cccnn3)cn2)COc2ccc(C#CC(C)(C)O)cc21]

Route 3. ¹H NMR (400 MHz, Methylene Chloride-d₂) δ 9.07 (d, J=4.8 Hz, 1H), 8.01 (s, 1H), 7.91 (d, J=7.1 Hz, 1H), 7.61 (s, 1H), 7.45 (dd, J=8.9, 4.8 Hz, 1H), 7.39-7.27 (m, 3H), 7.15 (d, J=8.2 Hz, 1H), 4.86 (dt, J=10.8, 7.1 Hz, 1H), 4.70 (dd, J=9.7, 7.3 Hz, 1H), 4.31 (t, J=10.5 Hz, 1H), 4.22 (s, 2H), 3.41 (s, 3H), 1.60 (s, 6H). LC/MS: Purity 95%, MS (m/e) 443 (M−H₂O+H)⁺.

(S)—N-(7-Bromo-5-methyl-4-oxo-2,3,4,5-tetrahydrobenzo[b][1,4]oxazepin-3-yl)-4-(pyridin-2-ylmethyl)-1H-pyrazole-1-carboxamide (I-18)

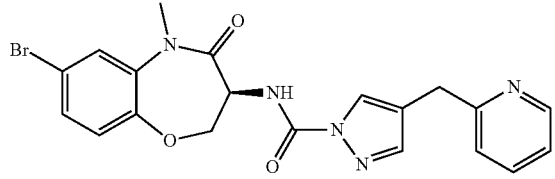 [SMILES: CN1C(=O)[C@@H](NC(=O)n2cc(Cc3ccccn3)cn2)COc2ccc(Br)cc21]

Route 2. $^1$H NMR (400 MHz, Chloroform-d) δ 8.54 (dt, J=4.6, 1.6 Hz, 1H), 7.99-7.92 (m, 2H), 7.60 (td, J=7.7, 1.9 Hz, 1H), 7.55 (d, J=0.8 Hz, 1H), 7.39-7.31 (m, 2H), 7.14 (t, J=6.2 Hz, 2H), 7.07 (dd, J=8.2, 0.6 Hz, 1H), 4.89 (dt, J=11.2, 7.3 Hz, 1H), 4.67 (dd, J=9.8, 7.3 Hz, 1H), 4.30 (dd, J=11.3, 9.8 Hz, 1H), 3.99 (s, 2H), 3.41 (s, 3H). LC/MS: Purity 98%, MS (m/e) 457 (M+H)$^+$.

(S)—N-(7-Bromo-5-methyl-4-oxo-2,3,4,5-tetrahydrobenzo[b][1,4]oxazepin-3-yl)-4-((6-methylpyridin-2-yl)methyl)-1H-pyrazole-1-carboxamide (I-19)

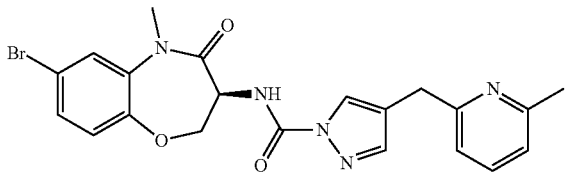 [SMILES: Cc1cccc(Cc2cnn(C(=O)N[C@H]3COc4ccc(Br)cc4N(C)C3=O)c2)n1]

Route 2. $^1$H NMR (400 MHz, Methanol-d$_4$) δ 8.33 (t, J=8.0 Hz, 1H), 8.16 (q, J=0.8 Hz, 1H), 7.72 (d, J=8.6, 2.3 Hz, 1H), 7.69 (d, J=0.8 Hz, 1H), 7.63 (d, J=8.0 Hz, 1H), 7.61 (d, J=2.3 Hz, 1H), 7.42 (dd, J=8.6, 2.3 Hz, 1H), 7.14 (d, J=8.6 Hz, 1H), 4.86 (dd, J=7.9, 3.5 Hz, 1H), 4.58 (dd, J=9.9, 7.5 Hz, 1H), 4.45 (ddd, J=11.1, 9.9, 1.1 Hz, 1H), 4.26 (s, 2H), 3.38 (s, 3H), 2.75 (s, 3H). LC/MS: Purity 98%, MS (m/e) 471 (M+H)$^+$.

(S)—N-(7-Bromo-5-methyl-4-oxo-2,3,4,5-tetrahydrobenzo[b][1,4]oxazepin-3-yl)-4-((6-fluoropyridin-2-yl)methyl)-1H-pyrazole-1-carboxamide (I-20)

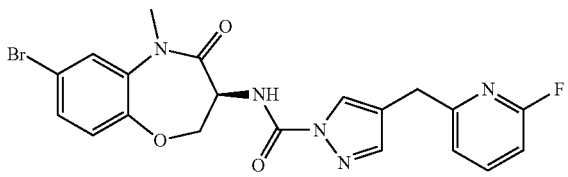 [SMILES: CN1C(=O)[C@@H](NC(=O)n2cc(Cc3cccc(F)n3)cn2)COc2ccc(Br)cc21]

Route 2. $^1$H NMR (400 MHz, Chloroform-d) δ 7.97 (d, J=1.0 Hz, 1H), 7.94 (d, J=7.3 Hz, 1H), 7.68 (td, J=8.2, 7.3 Hz, 1H), 7.55 (d, J=0.8 Hz, 1H), 7.38-7.30 (m, 2H), 7.06 (dd, J=8.1, 0.6 Hz, 1H), 6.98 (dd, J=7.4, 2.4 Hz, 1H), 6.76 (dd, J=8.2, 2.8 Hz, 1H), 4.87 (dt, J=11.2, 7.3 Hz, 1H), 4.66 (dd, J=9.8, 7.4 Hz, 1H), 4.29 (dd, J=11.3, 9.8 Hz, 1H), 3.91 (s, 2H), 3.40 (s, 3H). $^{19}$F NMR (376 MHz, Chloroform-d) δ −66.96 (d, J=8.0 Hz). LC/MS: Purity 98%, MS (m/e) 475 (M+H)$^+$.

(S)—N-(7-Bromo-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide (I-21)

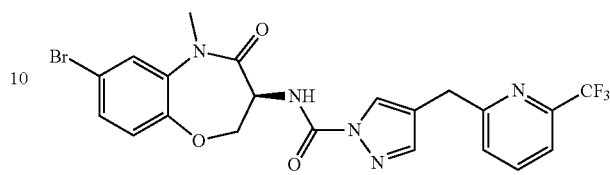

Route 2. $^1$H NMR (400 MHz, Methylene Chloride-d$_2$) δ 8.00 (q, J=0.9 Hz, 1H), 7.89 (d, J=7.1 Hz, 1H), 7.82 (td, J=7.8, 0.7 Hz, 1H), 7.62 (d, J=0.8 Hz, 1H), 7.59-7.53 (m, 1H), 7.42 (d, J=2.3 Hz, 1H), 7.42-7.34 (m, 2H), 7.11 (d, J=8.5 Hz, 1H), 4.88 (dt, J=11.2, 7.3 Hz, 1H), 4.70 (dd, J=9.8, 7.3 Hz, 1H), 4.30 (dd, J=11.3, 9.8 Hz, 1H), 4.08 (s, 2H), 3.41 (s, 3H). $^{19}$F NMR (376 MHz, Methylene Chloride-d$_2$) δ −68.40. LC/MS: Purity 95%, MS (m/e) 525 (M+H)$^+$.

(S)—N-(7-Bromo-5-methyl-4-oxo-2,3,4,5-tetrahydrobenzo[b][1,4]oxazepin-3-yl)-4-(pyridin-3-ylmethyl)-1H-pyrazole-1-carboxamide (I-22)

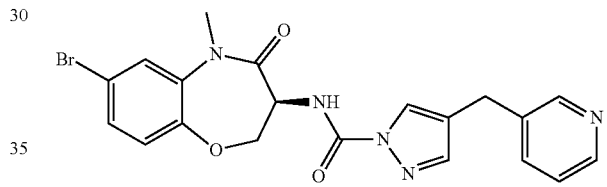

Route 2. $^1$H NMR (400 MHz, Methylene Chloride-d$_2$) δ 8.49 (d, J=2.3 Hz, 1H), 8.47 (dd, J=4.9, 1.6 Hz, 1H), 7.93-7.84 (m, 2H), 7.58-7.53 (m, 1H), 7.52 (d, J=0.9 Hz, 1H), 7.43 (d, J=2.3 Hz, 1H), 7.38 (dd, J=8.5, 2.3 Hz, 1H), 7.27 (ddd, J=7.9, 4.9, 0.9 Hz, 1H), 7.11 (d, J=8.5 Hz, 1H), 4.87 (dt, J=11.3, 7.3 Hz, 1H), 4.70 (dd, J=9.8, 7.4 Hz, 1H), 4.30 (dd, J=11.3, 9.8 Hz, 1H), 3.86 (s, 2H), 3.41 (s, 3H). LC/MS: Purity 98%, MS (m/e) 457 (M+H)$^+$.

(S)—N-(7-Bromo-5-methyl-4-oxo-2,3,4,5-tetrahydrobenzo[b][1,4]oxazepin-3-yl)-4-((6-methylpyridin-3-yl)methyl)-1H-pyrazole-1-carboxamide (I-23)

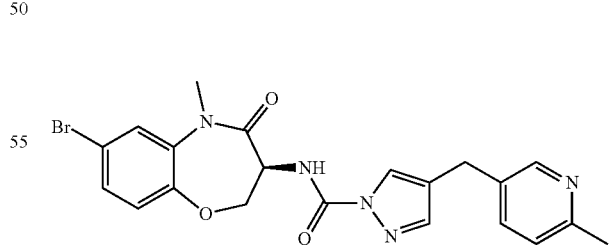

$^1$H NMR (400 MHz, Chloroform-d) δ 8.35 (d, J=2.1 Hz, 1H), 7.94 (d, J=7.2 Hz, 1H), 7.85 (app q, J=0.9 Hz, 1H), 7.45 (d, J=0.9 Hz, 1H), 7.38-7.31 (m, 3H), 7.07 (app dd, J=7.9, 0.9 Hz, 2H), 4.87 (dt, J=11.3, 7.3 Hz, 1H), 4.66 (dd, J=9.8, 7.4 Hz, 1H), 4.29 (dd, J=11.3, 9.8 Hz, 1H), 3.76 (s, 2H), 3.40 (s, 3H), 2.51 (s, 3H). LC/MS: Purity 94%, MS (m/e) 472 (M+H)$^+$.

(S)—N-(7-Bromo-5-methyl-4-oxo-2,3,4,5-tetrahydrobenzo[b][1,4]oxazepin-3-yl)-4-((6-fluoropyridin-3-yl)methyl)-1H-pyrazole-1-carboxamide (I-24)

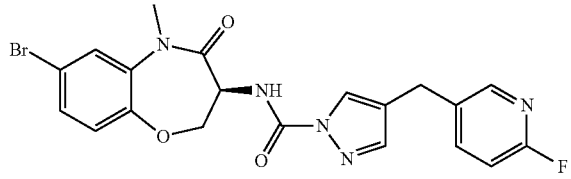 [SMILES: CN1C(=O)[C@@H](NC(=O)n2cc(Cc3ccc(F)nc3)cn2)COc2ccc(Br)cc21]

¹H NMR (400 MHz, Chloroform-d) δ 8.06 (ddd, J=2.6, 1.2, 0.6 Hz, 1H), 7.95 (d, J=7.2 Hz, 1H), 7.87 (q, J=0.9 Hz, 1H), 7.60-7.51 (m, 1H), 7.45 (d, J=0.9 Hz, 1H), 7.38-7.31 (m, 2H), 7.11-7.03 (m, 1H), 6.86 (ddd, J=8.3, 3.0, 0.7 Hz, 1H), 4.87 (dt, J=11.3, 7.3 Hz, 1H), 4.67 (dd, J=9.8, 7.4 Hz, 1H), 4.29 (dd, J=11.3, 9.8 Hz, 1H), 3.81 (s, 2H), 3.41 (s, 3H). ¹⁹F NMR (376 MHz, Chloroform-d) δ −70.85 (d, J=5.7 Hz). LCMS: Purity 96%, MS (m/e) 475 (M+H)⁺.

(S)—N-(7-Bromo-5-methyl-4-oxo-2,3,4,5-tetrahydrobenzo[b][1,4]oxazepin-3-yl)-4-(pyridazin-3-ylmethyl)-1H-pyrazole-1-carboxamide (I-25)

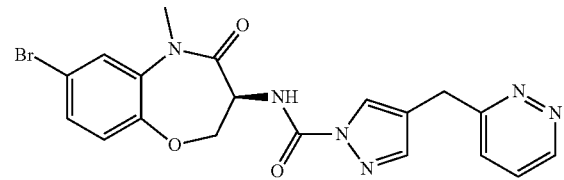 [SMILES: CN1C(=O)[C@@H](NC(=O)n2cc(Cc3cccnn3)cn2)COc2ccc(Br)cc21]

Route 2. ¹H NMR (400 MHz, Methylene Chloride-d₂) δ 9.06 (dd, J=4.8, 1.7 Hz, 1H), 8.02 (q, J=0.9 Hz, 1H), 7.89 (d, J=7.2 Hz, 1H), 7.61 (d, J=0.9 Hz, 1H), 7.48-7.31 (m, 4H), 7.11 (d, J=8.6 Hz, 1H), 4.88 (dt, J=11.2, 7.3 Hz, 1H), 4.70 (dd, J=9.8, 7.3 Hz, 1H), 4.30 (dd, J=11.3, 9.8 Hz, 1H), 4.22 (d, J=0.8 Hz, 2H), 3.41 (s, 3H). LC/MS: Purity 97%, MS (m/e) 458 (M+H)⁺.

(S)-4-((2-fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide (I-26)

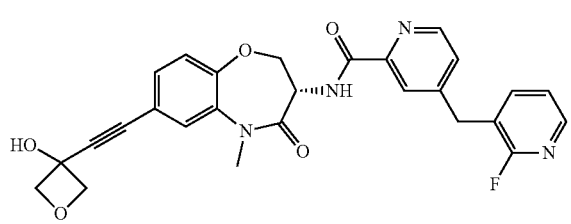 [SMILES: CN1C(=O)[C@@H](NC(=O)c2cc(Cc3cccnc3F)ccn2)COc2ccc(C#CC3(O)COC3)cc21]

¹H nmr (400 MHz, CDCl₃) δ 8.87 (1H, d, J 7.5 Hz, NH), 8.52 (1H, dd, J 5.0, 0.5 Hz, pyH-6), 8.11 (1H, dt, J 5.0, 1.0 Hz, FpyH-4), 7.92 (1H, br s, pyH-3), 7.55 (1H, ddd, J 9.5, 7.5, 2.0 Hz, FpyH-6), 7.31-7.26 (3H, m, pyH-5, oxobenzoxazapineH-6, H-8), 7.14 (1H, d, J 9.0 Hz, oxobenzoxazapineH-9), 7.15-7.12 (1H, m, FpyH-5), 5.04 (1H, dt, J 11.0, 7.5 Hz, oxobenzoxazapineH-3), 4.92 (2H, dd, J 6.5, 4.0 Hz, 2H of oxetaneH-2, H-4), 4.80-4.48 (2H, m, 2H of oxetaneH-2, H-4), 4.71 (1H, dd, J 9.5, 7.5 Hz, 1H of oxobenzoxazapineH-2), 4.30 (1H, dd, J 11.0, 9.5 Hz, 1H of oxobenzoxazapineH-2), 4.02 (2H, s, pyCH₂Fpy), 3.41 (3H, s, NCH₃); 19F nmr (380 MHz, CDCl₃) δ −71.1 (d, J 9.5 Hz); m/z: 503 [M+H]⁺ (found [M+H]⁺, 503.1746, C₂₇H₂₃FN₄O₅ requires [M+H]⁺ 503.1725).

(S)-4-((2-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide (I-27)

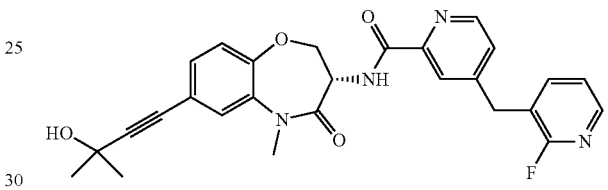

¹H nmr (400 MHz, CDCl₃) δ 8.86 (1H, d, J 7.5 Hz, NH), 8.52 (1H, d, J 5.0 Hz, pyH-6), 8.11 (1H, br d, J 4.5 Hz, FpyH-6), 7.92 (1H, d, J 1.0 Hz, pyH-3), 7.54 (1H, ddd, J 9.5, 7.5, 2.0 Hz, FpyH-4), 7.28-7.25 (3H, m, pyH-5, oxobenzoxazapineH-6, H-8), 7.15-7.11 (2H, m, FpyH-5, oxobenzoxazapineH-9), 5.03 (1H, dt, J 11.0, 7.5 Hz, oxobenzoxazapineH-3), 4.70 (1H, dd, J 9.5, 7.5 Hz, 1H of oxobenzoxazapineH-2), 4.28 (1H, dd, J 11.0, 9.5 Hz, 1H of oxobenzoxazapineH-2), 4.02 (2H, s, pyCH₂Fpy), 3.41 (3H, s, NCH₃), 1.61 (6H, s, C(CH₃)₂OH); 19F nmr (380 MHz, CDCl₃) δ −71.1 (d, J 9.5 Hz); m/z: 489 [M+H]⁺, 471 [M+H−H₂O]⁺ (found [M+H]⁺, 489.1938, C₂₇H₂₅FN₄O₄ requires [M+H]⁺ 489.1933).

(S)—N-(7-Bromo-5-methyl-4-oxo-2,3,4,5-tetrahydrobenzo[b][1,4]oxazepin-3-yl)-4-(pyridin-4-ylmethyl)-1H-pyrazole-1-carboxamide (I-28)

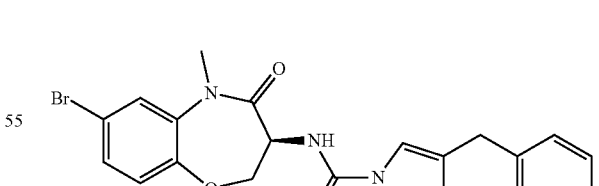

¹H NMR (400 MHz, Methylene Chloride-d₂) δ 8.52-8.46 (m, 2H), 7.93 (q, J=0.9 Hz, 1H), 7.90 (d, J=7.4 Hz, 1H), 7.52 (d, J=0.9 Hz, 1H), 7.43 (d, J=2.3 Hz, 1H), 7.39 (dd, J=8.5, 2.3 Hz, 1H), 7.17-7.13 (m, 2H), 7.12 (d, J=8.5 Hz, 1H), 4.88 (dt, J=11.1, 7.2 Hz, 1H), 4.70 (dd, J=9.8, 7.4 Hz, 1H), 4.31 (dd, J=11.3, 9.8 Hz, 1H), 3.85 (s, 2H), 3.41 (s, 3H). LC/MS: Purity 99%, MS (m/e) 457 (M+H)⁺.

(S)—N-(7-(3-Hydroxy-3-methylbut-1-yn-1-yl)-5-methyl-4-oxo-2,3,4,5-tetrahydrobenzo[b][1,4]oxazepin-3-yl)-4-(pyridin-4-ylmethyl)-1H-pyrazole-1-carboxamide (I-29)

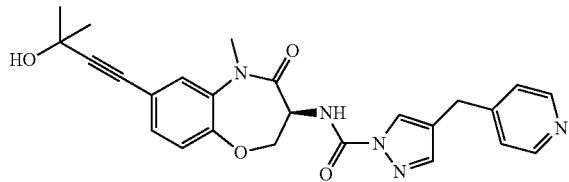 [SMILES: CN1C(=O)[C@@H](NC(=O)n2cc(Cc3ccncc3)cn2)COc2ccc(C#CC(C)(C)O)cc21]

$^1$H NMR (400 MHz, Methylene Chloride-d$_2$) δ 8.53 (s, 2H), 7.96-7.90 (m, 2H), 7.51 (d, J=0.8 Hz, 1H), 7.32 (d, J=1.9 Hz, 1H), 7.28 (dd, J=8.3, 1.9 Hz, 1H), 7.18-7.11 (m, 3H), 4.87 (dt, J=11.2, 7.2 Hz, 1H), 4.71 (dd, J=9.7, 7.3 Hz, 1H), 4.32 (dd, J=11.3, 9.8 Hz, 1H), 3.84 (s, 2H), 3.40 (s, 3H), 1.60 (s, 6H). LC/MS: Purity 98%, MS (m/e) 460 (M+H)$^+$.

(S)—N-(7-Bromo-5-methyl-4-oxo-2,3,4,5-tetrahydrobenzo[b][1,4]oxazepin-3-yl)-4-(pyrimidin-2-ylmethyl)-1H-pyrazole-1-carboxamide (I-30)

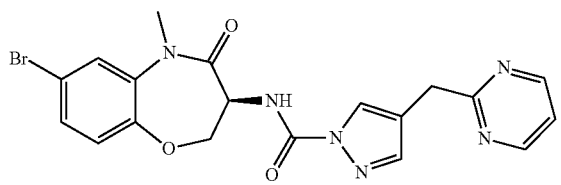 [SMILES: CN1C(=O)[C@@H](NC(=O)n2cc(Cc3ncccn3)cn2)COc2ccc(Br)cc21]

$^1$H NMR (400 MHz, Methylene Chloride-d$_2$) δ 8.65 (d, J=4.9 Hz, 2H), 8.04 (app q, J=0.9 Hz, 1H), 7.89 (d, J=7.2 Hz, 1H), 7.65 (d, J=0.8 Hz, 1H), 7.41 (d, J=2.3 Hz, 1H), 7.36 (dd, J=8.5, 2.3 Hz, 1H), 7.15 (t, J=4.9 Hz, 1H), 7.09 (d, J=8.5 Hz, 1H), 4.87 (dt, J=11.2, 7.3 Hz, 1H), 4.68 (dd, J=9.8, 7.4 Hz, 1H), 4.30 (dd, J=11.3, 9.8 Hz, 1H), 4.13 (s, 2H), 3.39 (s, 3H). LCMS: Purity 96%, MS (m/e) 457/459 (M+H)$^+$.

(S)—N-(7-(3-Hydroxy-3-methylbut-1-yn-1-yl)-5-methyl-4-oxo-2,3,4,5-tetrahydrobenzo[b][1,4]oxazepin-3-yl)-4-(pyrimidin-2-ylmethyl)-1H-pyrazole-1-carboxamide (I-31)

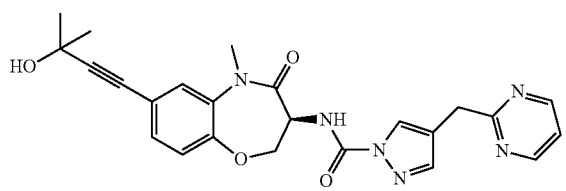 [SMILES: CN1C(=O)[C@@H](NC(=O)n2cc(Cc3ncccn3)cn2)COc2ccc(C#CC(C)(C)O)cc21]

$^1$H NMR (400 MHz, Chloroform-d) δ 8.66 (d, J=4.9 Hz, 2H), 8.05 (app q, J=0.8 Hz, 1H), 7.95 (d, J=7.2 Hz, 1H), 7.62 (d, J=0.8 Hz, 1H), 7.25 (dd, J=4.8, 1.9 Hz, 2H), 7.14 (t, J=4.9 Hz, 1H), 7.12-7.08 (m, 1H), 4.85 (dt, J=11.3, 7.3 Hz, 1H), 4.66 (dd, J=9.8, 7.3 Hz, 1H), 4.28 (dd, J=11.3, 9.8 Hz, 1H), 4.13 (s, 2H), 3.39 (s, 3H), 2.02 (s, 1H), 1.60 (s, 6H). LCMS: Purity 99%, MS (m/e) 461 (M+H)$^+$.

(S)-4-((6-Fluoropyridin-2-yl)methyl)-N-(7-((3-hydroxyoxetan-3-yl)ethynyl)-5-methyl-4-oxo-2,3,4,5-tetrahydrobenzo[b][1,4]oxazepin-3-yl)-1H-pyrazole-1-carboxamide (I-32)

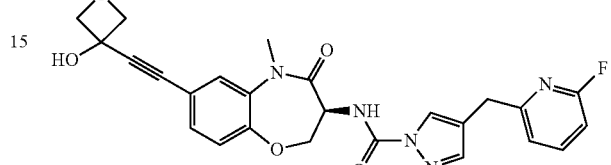

$^1$H NMR (400 MHz, Methylene Chloride-d$_2$) δ 7.97 (app q, J=0.9 Hz, 1H), 7.90 (d, J=7.0 Hz, 1H), 7.72 (td, J=8.3, 7.4 Hz, 1H), 7.59 (d, J=0.8 Hz, 1H), 7.38 (d, J=1.9 Hz, 1H), 7.35 (dd, J=8.2, 2.0 Hz, 1H), 7.18 (d, J=8.2 Hz, 1H), 7.05 (ddd, J=7.4, 2.6, 0.7 Hz, 1H), 6.78 (app dd, J=8.1, 2.9 Hz, 1H), 4.93-4.82 (m, 3H), 4.76-4.67 (m, 3H), 4.32 (dd, J=11.3, 9.8 Hz, 1H), 3.93 (s, 2H), 3.41 (s, 3H), 2.71 (s, 1H). $^{19}$F NMR (376 MHz, Methylene Chloride-d$_2$) δ −68.27 (d, J=8.2 Hz). LCMS: Purity 98%, MS (m/e) 492 (M+H)$^+$.

(S)-4-((6-Fluoropyridin-2-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide (I-33)

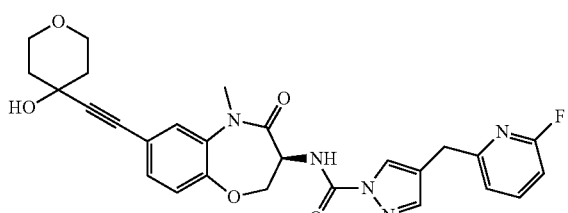

$^1$H NMR (400 MHz, Methylene Chloride-d$_2$) 7.97 (app q, J=0.8 Hz, 1H), 7.89 (d, J=7.1 Hz, 1H), 7.72 (td, J=8.3, 7.4 Hz, 1H), 7.58 (d, J=0.8 Hz, 1H), 7.35-7.31 (m, 2H), 7.16 (dd, J=8.2, 0.5 Hz, 1H), 7.05 (ddd, J=7.4, 2.5, 0.7 Hz, 1H), 6.82-6.73 (app m, 1H), 4.86 (dt, J=11.3, 7.2 Hz, 1H), 4.70 (dd, J=9.8, 7.3 Hz, 1H), 4.31 (dd, J=11.3, 9.8 Hz, 1H), 3.93 (s, 2H), 3.92-3.86 (m, 2H), 3.68 (ddd, J=11.8, 9.0, 2.9 Hz, 2H), 3.41 (s, 3H), 2.22 (s, 1H), 2.04-1.98 (m, 2H), 1.84 (ddd, J=13.0, 9.1, 4.0 Hz, 2H). $^{19}$F NMR (376 MHz, Methylene Chloride-d2) δ −68.27 (d, J=8.2 Hz). LCMS: Purity 97%, MS (m/e) 520 (M+H)$^+$.

(S)-4-((6-Fluoropyridin-2-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide (I-34)

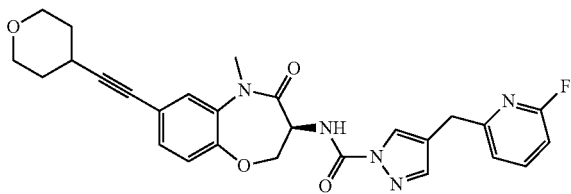 [SMILES: CN1C(=O)[C@@H](NC(=O)n2cc(Cc3cccc(F)n3)cn2)COc2ccc(C#CC3CCOCC3)cc21]

¹H NMR (400 MHz, Methylene Chloride-d2) δ 7.97 (q, J=0.9 Hz, 1H), 7.89 (d, J=7.1 Hz, 1H), 7.72 (td, J=8.2, 7.4 Hz, 1H), 7.58 (d, J=0.8 Hz, 1H), 7.33-7.24 (m, 2H), 7.13 (dd, J=8.2, 0.4 Hz, 1H), 7.05 (ddd, J=7.4, 2.5, 0.7 Hz, 1H), 6.78 (ddd, J=8.2, 2.8, 0.7 Hz, 1H), 4.85 (dt, J=11.2, 7.2 Hz, 1H), 4.69 (dd, J=9.8, 7.3 Hz, 1H), 4.29 (dd, J=11.2, 9.8 Hz, 1H), 3.92 (s, 2H), 3.92-3.88 (m, 2H), 3.50 (ddd, J=11.7, 8.9, 2.9 Hz, 2H), 3.40 (s, 3H), 2.84 (tt, J=8.7, 4.1 Hz, 1H), 1.93-1.86 (m, 2H), 1.79-1.67 (m, 2H). ¹⁹F NMR (376 MHz, Methylene Chloride-d2) δ −68.27 (d, J=8.2 Hz). LCMS: Purity 91%, MS (m/e) 504 (M+H)⁺.

(S)—N-(8-Bromo-1-methyl-2-oxo-2,3,4,5-tetrahydro-1H-benzo[b]azepin-3-yl)-4-((6-fluoropyridin-2-yl)methyl)-1H-pyrazole-1-carboxamide (I-35)

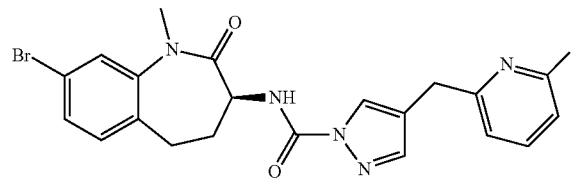

¹H NMR (400 MHz, Methylene Chloride-d2) δ 7.97 (app q, J=0.8 Hz, 1H), 7.86 (d, J=7.5 Hz, 1H), 7.71 (td, J=8.2, 7.4 Hz, 1H), 7.56 (d, J=0.9 Hz, 1H), 7.41-7.33 (m, 2H), 7.17 (d, J=8.0 Hz, 1H), 7.04 (ddd, J=7.4, 2.5, 0.7 Hz, 1H), 6.78 (ddd, J=8.2, 2.8, 0.7 Hz, 1H), 4.40 (dt, J=11.4, 7.4 Hz, 1H), 3.92 (s, 2H), 3.39 (s, 3H), 2.91-2.76 (m, 1H), 2.78-2.52 (m, 2H), 2.12-2.00 (m, 1H). ¹⁹F NMR (376 MHz, Methylene Chloride-d2) δ −68.34 (d, J=8.2 Hz). LCMS: Purity 94%, MS (m/e) 472/474 (M+H)⁺.

(S)-4-((6-Fluoropyridin-2-yl)methyl)-N-(8-((3-hydroxyoxetan-3-yl)ethynyl)-1-methyl-2-oxo-2,3,4,5-tetrahydro-1H-benzo[b]azepin-3-yl)-1H-pyrazole-1-carboxamide (I-36)

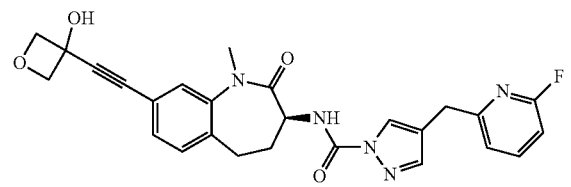 [SMILES: CN1C(=O)[C@@H](NC(=O)n2cc(Cc3cccc(F)n3)cn2)CCc2ccc(C#CC3(O)COC3)cc21]

¹H NMR (400 MHz, Chloroform-d) δ 7.97 (q, J=0.9 Hz, 1H), 7.95 (s, 1H), 7.68 (td, J=8.2, 7.4 Hz, 1H), 7.53 (d, J=0.8 Hz, 1H), 7.30-7.25 (m, 2H), 7.25-7.18 (m, 1H), 7.04-6.94 (m, 1H), 6.76 (ddd, J=8.1, 2.8, 0.7 Hz, 1H), 4.93 (dd, J=6.6, 0.8 Hz, 2H), 4.79 (dd, J=6.6, 0.9 Hz, 2H), 4.45 (dt, J=11.4, 7.4 Hz, 1H), 3.91 (s, 2H), 3.41 (s, 3H), 2.95-2.80 (m, 1H), 2.75-2.60 (m, 2H), 2.14-2.04 (m, 1H), 2.03 (s, 1H). ¹⁹F NMR (376 MHz, Chloroform-d) δ −67.08 (d, J=8.2 Hz). LCMS: Purity 97%, MS (m/e) 490 (M+H)⁺.

(S)-4-((6-Fluoropyridin-2-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide (I-37)

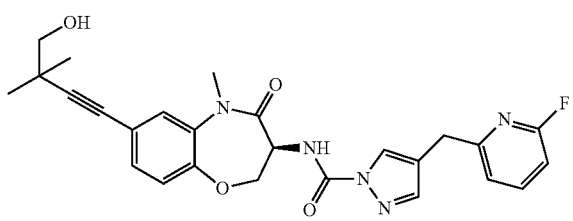 [SMILES: CN1C(=O)[C@@H](NC(=O)n2cc(Cc3cccc(F)n3)cn2)COc2ccc(C#CC(C)(C)CO)cc21]

¹H NMR (400 MHz, Methylene Chloride-d2) δ 7.98 (app q, J=0.9 Hz, 1H), 7.89 (d, J=7.1 Hz, 1H), 7.72 (app td, J=8.3, 7.4 Hz, 1H), 7.58 (d, J=0.8 Hz, 1H), 7.33-7.22 (m, 2H), 7.16-7.06 (m, 1H), 7.05 (ddd, J=7.4, 2.5, 0.7 Hz, 1H), 6.78 (ddd, J=8.2, 2.8, 0.7 Hz, 1H), 4.84 (dt, J=11.2, 7.2 Hz, 1H), 4.69 (dd, J=9.8, 7.3 Hz, 1H), 4.29 (dd, J=11.3, 9.8 Hz, 1H), 3.93 (s, 2H), 3.48 (d, J=5.9 Hz, 2H), 3.40 (s, 3H), 1.83 (t, J=6.8 Hz, 1H), 1.29 (s, 6H). ¹⁹F NMR (376 MHz, Methylene Chloride-d2) δ −68.27 (d, J=8.2 Hz). LCMS: Purity 98%, MS (m/e) 492 (M+H)⁺.

(S)-4-((6-Fluoropyridin-2-yl)methyl)-N-(8-(3-hydroxy-3-methylbut-1-yn-1-yl)-1-methyl-2-oxo-2,3,4,5-tetrahydro-1H-benzo[b]azepin-3-yl)-1H-pyrazole-1-carboxamide (I-38)

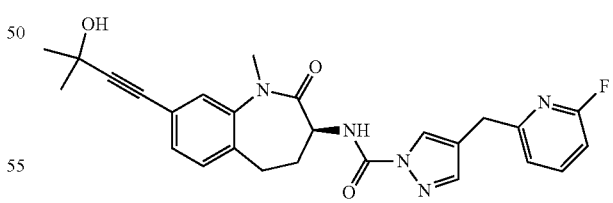

¹H NMR (400 MHz, Methylene Chloride-d2) δ 7.97 (t, J=0.9 Hz, 1H), 7.88 (d, J=7.4 Hz, 1H), 7.71 (td, J=8.2, 7.4 Hz, 1H), 7.55 (d, J=0.8 Hz, 1H), 7.28-7.23 (m, 3H), 7.04 (ddd, J=7.4, 2.5, 0.6 Hz, 1H), 6.77 (ddd, J=8.2, 2.9, 0.6 Hz, 1H), 4.39 (dt, J=11.4, 7.4 Hz, 1H), 3.92 (s, 2H), 3.39 (s, 3H), 2.96-2.81 (m, 1H), 2.75-2.60 (m, 2H), 2.12-1.98 (m, 1H), 1.59 (s, 6H). ¹⁹F NMR (376 MHz, Methylene Chloride-d2) δ −68.35 (d, J=8.1 Hz). LCMS: Purity 95%, MS (m/e) 476 (M+H)⁺.

(S)-4-((6-fluoropyridin-2-yl)methyl)-N-(8-(4-hydroxy-3,3-dimethylbut-1-yn-1-yl)-1-methyl-2-oxo-2,3,4,5-tetrahydro-1H-benzo[b]azepin-3-yl)-1H-pyrazole-1-carboxamide (I-39)

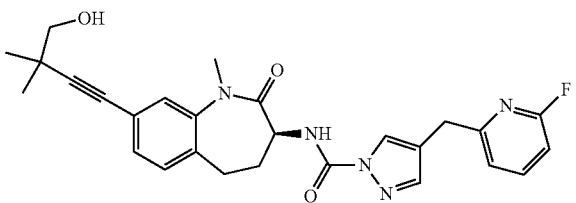 [SMILES: CN1C(=O)[C@@H](NC(=O)n2cc(Cc3cccc(F)n3)cn2)CCc2ccc(C#CC(C)(C)CO)cc21]

¹H NMR (400 MHz, Methylene Chloride-d2) δ 7.97 (q, J=0.9 Hz, 1H), 7.87 (d, J=7.4 Hz, 1H), 7.71 (td, J=8.2, 7.4 Hz, 1H), 7.55 (d, J=0.8 Hz, 1H), 7.28-7.18 (m, 3H), 7.04 (ddd, J=7.4, 2.6, 0.7 Hz, 1H), 6.77 (ddd, J=8.1, 2.8, 0.7 Hz, 1H), 4.38 (dt, J=11.5, 7.4 Hz, 1H), 3.92 (s, 2H), 3.48 (d, J=6.8 Hz, 2H), 3.39 (s, 3H), 2.95-2.81 (m, 1H), 2.73-2.58 (m, 2H), 2.09-2.01 (m, 1H) (td, J=11.5, 8.0 Hz, 1H), 1.82 (t, J=6.9 Hz, 1H), 1.29 (s, 6H). ¹⁹F NMR (376 MHz, Methylene Chloride-d₂) δ −68.35 (d, J=8.3 Hz). LCMS: Purity 94%, MS (m/e) 490 (M+H)⁺.

(S)-4-((6-Fluoropyridin-2-yl)methyl)-N-(8-((4-hydroxytetrahydro-2H-pyran-4-yl)ethynyl)-1-methyl-2-oxo-2,3,4,5-tetrahydro-1H-benzo[b]azepin-3-yl)-1H-pyrazole-1-carboxamide (I-40)

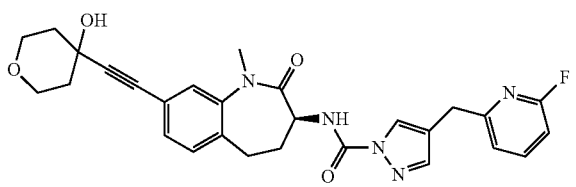 [SMILES: CN1C(=O)[C@@H](NC(=O)n2cc(Cc3cccc(F)n3)cn2)CCc2ccc(C#CC3(O)CCOCC3)cc21]

¹H NMR (400 MHz, Methylene Chloride-d2) δ 7.97 (d, J=1.0 Hz, 1H), 7.88 (d, J=7.4 Hz, 1H), 7.76-7.67 (m, 1H), 7.56 (app m, 1H), 7.32-7.20 (m, 3H), 7.04 (dd, J=7.4, 2.5 Hz, 1H), 6.77 (dd, J=8.2, 2.8 Hz, 1H), 4.39 (dt, J=11.5, 7.3 Hz, 1H), 3.92 (s, 2H), 3.90-3.86 (m, 1H), 3.68 (ddd, J=11.8, 9.1, 2.9 Hz, 2H), 3.39 (s, 3H), 2.94-2.84 (m, 1H), 2.72-2.61 (m, 3H), 2.13-1.95 (m, 3H), 1.90-1.82 (m, 2H). ¹⁹F NMR (376 MHz, Methylene Chloride-d2) δ −68.30 (d, J=8.5 Hz). LCMS: Purity 97%, MS (m/e) 518 (M+H)⁺.

(S)-4-((6-Fluoropyridin-2-yl)methyl)-N-(8-((1-hydroxycyclobutyl)ethynyl)-1-methyl-2-oxo-2,3,4,5-tetrahydro-1H-benzo[b]azepin-3-yl)-1H-pyrazole-1-carboxamide (I-41)

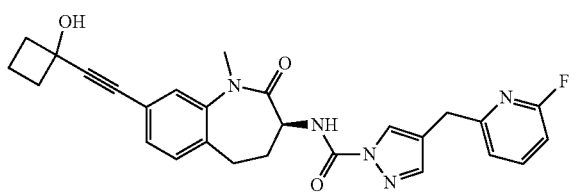 [SMILES: CN1C(=O)[C@@H](NC(=O)n2cc(Cc3cccc(F)n3)cn2)CCc2ccc(C#CC3(O)CCC3)cc21]

¹H NMR (400 MHz, Chloroform-d) δ 7.97 (q, J=0.9 Hz, 1H), 7.95 (s, 1H), 7.67 (td, J=8.2, 7.4 Hz, 1H), 7.53 (d, J=0.9 Hz, 1H), 7.27 (d, J=6.9 Hz, 2H), 7.22-7.15 (m, 1H), 6.98 (dd, J=7.5, 2.4 Hz, 1H), 6.76 (dd, J=8.2, 2.9 Hz, 1H), 4.45 (dt, J=11.0, 7.3 Hz, 1H), 3.91 (s, 2H), 3.41 (s, 3H), 2.94-2.81 (m, 1H), 2.75-2.59 (m, 2H), 2.59-2.44 (m, 2H), 2.40-2.24 (m, 2H), 2.23 (s, 1H), 2.11-2.03 (m, 1H) 1.94-1.81 (m, 2H). ¹⁹F NMR (376 MHz, Chloroform-d) δ −67.09 (d, J=8.1 Hz). LCMS: Purity 96%, MS (m/e) 488 (M+H)⁺.

(S)—N-(7-Bromo-5-methyl-4-oxo-2,3,4,5-tetrahydrobenzo[b][1,4]oxazepin-3-yl)-4-((2-fluoropyridin-3-yl)methyl)-1H-pyrazole-1-carboxamide (I-42)

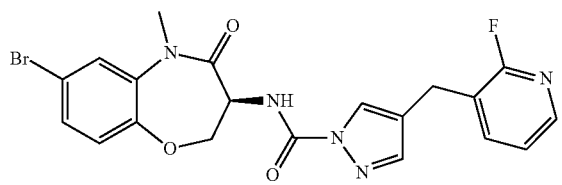 [SMILES: CN1C(=O)[C@@H](NC(=O)n2cc(Cc3cccnc3F)cn2)COc2ccc(Br)cc21]

¹H NMR (400 MHz, Chloroform-d) 68.09 (d, J=5.0 Hz, 1H), 7.97 (d, J=7.3 Hz, 1H), 7.93 (s, 1H), 7.55 (ddd, J=9.7, 7.4, 1.9 Hz, 1H), 7.51 (s, 1H), 7.39-7.31 (m, 2H), 7.12 (ddd, J=7.1, 4.9, 1.7 Hz, 1H), 4.88 (dt, J=11.3, 7.3 Hz, 1H), 4.67 (dd, J=9.8, 7.4 Hz, 1H), 4.30 (dd, J=11.3, 9.8 Hz, 1H), 3.83 (s, 2H), 3.41 (s, 3H). ¹³C NMR (101 MHz, Chloroform-d) δ 168.47, 162.93, 149.10 (d, J=14.4 Hz), 146.01 (d, J=14.6 Hz), 143.07, 140.69 (d, J=5.3 Hz), 137.52, 130.71, 127.14, 126.49, 124.57, 121.99 (d, J=30.7 Hz), 121.78 (d, J=4.4 Hz), 121.30, 118.23, 77.27, 50.16, 35.65, 23.71. ¹⁹F NMR (376 MHz, Chloroform-d) δ −71.94. LCMS: Purity 96%, MS (m/z) 474/476 (M+H)⁺.

(S)-4-((2-Fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide (I-43)

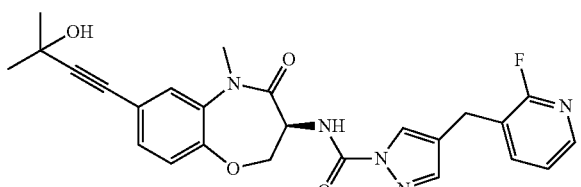

¹H NMR (400 MHz, Chloroform-d) δ 8.06 (d, J=4.7 Hz, 1H), 7.97 (d, J=7.2 Hz, 1H), 7.91 (s, 1H), 7.52 (t, J=8.5 Hz, 1H), 7.48 (s, 1H), 7.26-7.20 (m, 2H), 7.12-7.05 (m, 2H), 4.84 (dt, J=11.2, 7.2 Hz, 1H), 4.65 (dd, J=9.8, 7.3 Hz, 1H), 4.29 (dd, J=11.3, 9.8 Hz, 1H), 3.79 (s, 2H), 3.37 (s, 3H), 1.58 (s, 6H). ¹³C NMR (101 MHz, Chloroform-d) δ 168.40, 162.80, 160.42, 149.79, 148.93, 145.81 (d, J=14.4 Hz), 142.96, 140.69 (d, J=5.0 Hz), 135.98, 130.94, 127.09, 126.52, 123.06, 121.95 (d, J=30.6 Hz), 121.72 (d, J=4.2 Hz), 121.16, 120.58, 94.89, 80.41, 77.11, 65.42, 50.03, 35.55, 31.42, 23.57. ¹⁹F NMR (376 MHz, Chloroform-d) δ −72.07. LCMS: Purity 97%, MS (m/z) 478 (M+H)⁺.

127

(S)-4-((2-Fluoropyridin-3-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide (I-44)

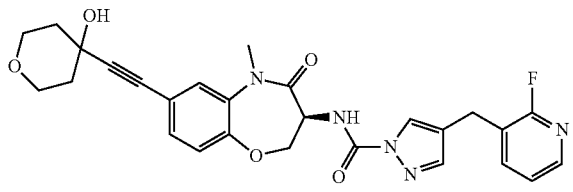 [SMILES: CN1C(=O)[C@@H](NC(=O)n2cc(Cc3cccnc3F)cn2)COc2ccc(C#CC3(O)CCOCC3)cc21]

¹H NMR (400 MHz, Chloroform-d) δ 8.05 (d, J=4.8 Hz, 1H), 7.95 (d, J=7.3 Hz, 1H), 7.90 (d, J=1.0 Hz, 1H), 7.52 (ddd, J=9.5, 7.3, 2.0 Hz, 1H), 7.48 (s, 1H), 7.29-7.23 (m, 2H), 7.14-7.05 (m, 2H), 6.19 (d, J=16.0 Hz, 1H), 5.77 (d, J=16.0 Hz, 1H), 4.84 (dt, J=11.3, 7.3 Hz, 1H), 4.64 (dd, J=9.8, 7.3 Hz, 1H), 4.29 (dd, J=11.3, 9.8 Hz, 1H), 3.96-3.82 (m, 2H), 3.79 (s, 2H), 3.76-3.56 (m, 4H), 3.38 (s, 3H). ¹³C NMR (101 MHz, Chloroform-d) δ 168.47, 162.88, 160.50, 150.08 (d, J=15.7 Hz), 149.03, 145.88 (d, J=14.5 Hz), 143.04, 140.74 (d, J=5.4 Hz), 136.19, 131.13, 127.12, 126.65, 123.25, 121.99 (d, J=30.5 Hz), 121.76 (d, J=4.4 Hz), 121.29, 120.24, 107.45, 92.79, 92.55, 83.34, 82.77, 77.19, 69.29, 66.07, 64.87, 63.47, 50.10, 39.99, 37.35, 35.62, 23.66. ¹⁹F NMR (376 MHz, Chloroform-d) δ −72.03. LCMS: Purity 95%, MS (m/z) 520 (M+H)⁺.

(S)-4-((2-Fluoropyridin-3-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide (I-45)

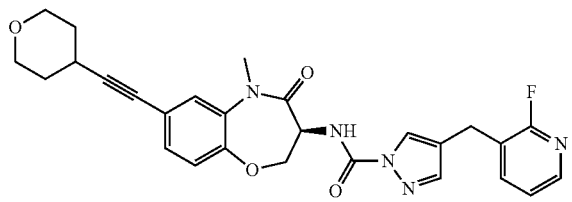 [SMILES: CN1C(=O)[C@@H](NC(=O)n2cc(Cc3cccnc3F)cn2)COc2ccc(C#CC3CCOCC3)cc21]

¹H NMR (400 MHz, Chloroform-d) δ 8.07 (s, 1H), 7.96 (d, J=7.2 Hz, 1H), 7.91 (s, 1H), 7.52 (t, J=9.9 Hz, 1H), 7.49 (s, 1H), 7.28-7.21 (m, 2H), 7.13-7.05 (m, 2H), 4.85 (dt, J=11.2, 7.3 Hz, 1H), 4.66 (dd, J=9.8, 7.3 Hz, 1H), 4.28 (dd, J=11.3, 9.8 Hz, 1H), 3.92 (ddd, J=11.6, 5.4, 3.7 Hz, 2H), 3.80 (s, 2H), 3.52 (ddd, J=11.7, 8.8, 2.9 Hz, 2H), 3.40 (s, 3H), 2.82 (tt, J=8.5, 4.1 Hz, 1H), 1.96-1.83 (m, 2H), 1.74 (dtd, J=12.8, 8.8, 3.7 Hz, 2H). ¹³C NMR (101 MHz, Chloroform-d) δ 168.37, 162.79, 160.41, 149.51, 145.82 (d, J=14.5 Hz), 142.87, 140.52 (d, J=5.3 Hz), 135.94, 130.91, 126.99, 126.40, 122.96, 122.05, 121.72-121.49 (m), 121.36, 121.11, 93.17, 79.97, 77.13, 66.38, 50.03, 35.45, 32.13, 26.81, 23.55. ¹⁹F NMR (376 MHz, Chloroform-d) δ −71.95. LCMS: Purity 98%, MS (m/z) 504 (M+H)⁺.

128

(S)-4-((2-Fluoropyridin-3-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide (I-46)

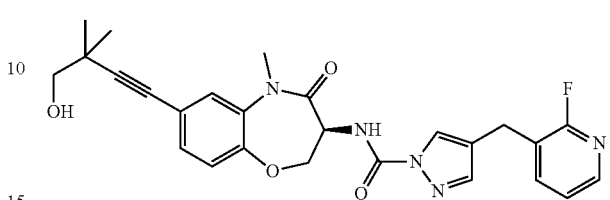

¹H NMR (400 MHz, Chloroform-d) δ 8.10-8.03 (m, 1H), 7.96 (d, J=7.2 Hz, 1H), 7.91 (s, 1H), 7.52 (ddd, J=9.6, 7.3, 1.9 Hz, 1H), 7.49 (s, 1H), 7.28-7.18 (m, 2H), 7.12-7.06 (m, 2H), 4.84 (dt, J=11.2, 7.3 Hz, 1H), 4.66 (dd, J=9.7, 7.3 Hz, 1H), 4.28 (dd, J=11.3, 9.8 Hz, 1H), 3.80 (s, 2H), 3.49 (s, 2H), 3.40 (s, 3H), 1.29 (s, 6H). ¹³C NMR (101 MHz, Chloroform-d) δ 168.50, 162.92, 160.54, 149.64, 149.01, 145.95 (d, J=14.5 Hz), 143.00, 140.65 (d, J=5.3 Hz), 136.07, 131.04, 127.12, 126.53, 123.09, 122.18, 121.83-121.65 (m), 121.49, 121.24, 93.30, 80.10, 77.26, 66.51, 50.16, 35.58, 32.26, 26.94, 23.68. ¹⁹F NMR (376 MHz, Chloroform-d) δ−71.97. LCMS: Purity 96%, MS (m/z) 492 (M+H)⁺.

(S)-4-((2-Fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)-1H-pyrazole-1-carboxamide (I-47)

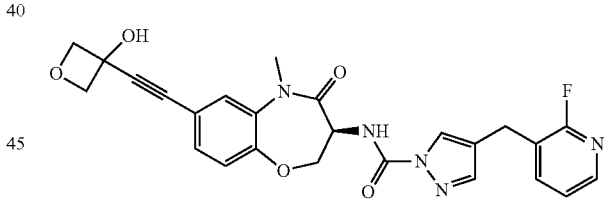

¹H NMR (400 MHz, Chloroform-d) δ 8.10-8.03 (m, 1H), 7.98 (d, J=7.2 Hz, 1H), 7.92 (s, 1H), 7.58-7.51 (m, 1H), 7.50 (s, 1H), 7.43 (s, 1H), 7.29-7.24 (m, 1H), 7.16-7.08 (m, 2H), 4.94-4.90 (m, 2H), 4.87 (dt, J=11.3, 7.3 Hz, 1H), 4.81-4.77 (m, 2H), 4.67 (dd, J=9.7, 7.3 Hz, 1H), 4.32 (dd, J=11.3, 9.8 Hz, 1H), 3.85 (s, 1H), 3.81 (s, 2H), 3.40 (s, 3H). ¹³C NMR (101 MHz, Chloroform-d) δ 168.37, 162.80, 160.42, 150.35, 148.95, 145.81 (d, J=14.5 Hz), 145.37 (d, J=14.3 Hz), 142.96, 140.64 (d, J=5.3 Hz), 136.17, 133.20, 131.00, 127.03, 126.58, 123.28, 121.90 (d, J=30.5 Hz), 121.67 (d, J=4.4 Hz), 121.57 (d, J=4.4 Hz), 121.20, 119.58, 88.93, 84.60, 77.11, 67.38, 50.02, 35.54, 23.58. ¹⁹F NMR (376 MHz, Chloroform-d) δ −72.04. LCMS: Purity 95%, MS (m/z) 492.6 (M+H)⁺.

129

(S)-4-((2-Fluoropyridin-3-yl)methyl)-N-(7-(((1-hydroxycyclobutyl)ethynyl)-5-methyl-4-oxo-2,3,4,5-tetrahydrobenzo[b][1,4]oxazepin-3-yl)-1H-pyrazole-1-carboxamide (I-48)

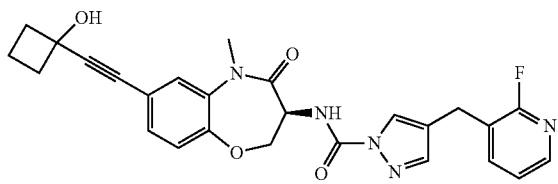 [SMILES: CN1C(=O)[C@@H](NC(=O)n2cc(Cc3cccnc3F)cn2)COc2ccc(C#CC3(O)CCC3)cc21]

$^1$H NMR (400 MHz, Chloroform-d) δ 8.07 (d, J=5.0 Hz, 1H), 7.97 (d, J=7.2 Hz, 1H), 7.92 (s, 1H), 7.53 (ddd, J=9.5, 7.3, 2.0 Hz, 1H), 7.50 (s, 1H), 7.30-7.26 (m, 2H), 7.13-7.08 (m, 2H), 4.86 (dt, J=11.2, 7.2 Hz, 1H), 4.67 (dd, J=9.8, 7.3 Hz, 1H), 4.30 (dd, J=11.3, 9.8 Hz, 1H), 3.81 (s, 2H), 3.40 (s, 3H), 2.58-2.45 (m, 2H), 2.40-2.26 (m, 2H), 1.94-1.80 (m, 2H). $^{13}$C NMR (101 MHz, Chloroform-d) δ 168.37, 162.80, 160.42, 149.90, 148.91, 145.83 (d, J=14.6 Hz), 142.91, 140.58 (d, J=5.3 Hz), 136.01, 130.98, 127.02, 126.54, 123.07, 121.89 (d, J=30.7 Hz), 121.63 (d, J=4.4 Hz), 121.14, 120.52, 93.47, 81.79, 77.12, 68.19, 50.03, 38.55, 35.50, 23.55, 12.98. $^{19}$F NMR (376 MHz, Chloroform-d) δ− 71.98. LCMS: Purity 98%, MS (m/z) 490.6 (M+H)$^+$.

(S)—N-(7-Bromo-5-methyl-4-oxo-2,3,4,5-tetrahydrobenzo[b][1,4]oxazepin-3-yl)-4-((2,6-difluoropyridin-3-yl)methyl)-1H-pyrazole-1-carboxamide (I-49)

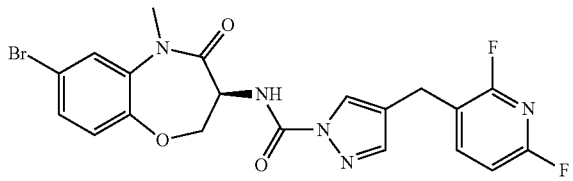

$^1$H NMR (400 MHz, DMSO-d6) δ 8.54-8.47 (m, 1H), 8.09 (s, 1H), 8.02 (dt, J=9.9, 8.0 Hz, 1H), 7.73 (d, J=2.4 Hz, 1H), 7.71 (s, 1H), 7.43 (dd, J=8.6, 2.4 Hz, 1H), 7.17 (d, J=8.5 Hz, 1H), 7.11-7.07 (m, 1H), 4.74-4.61 (m, 2H), 4.48-4.35 (m, 1H), 3.82 (s, 2H), 3.27 (s, 3H). $^{13}$C NMR (101 MHz, DMSO-d6) δ 168.76, 161.97-159.22 (m), 158.38 (d, J=13.7 Hz), 149.36, 149.18, 147.11 (dd, J=7.8, 5.5 Hz), 143.27, 138.48, 130.33, 127.88, 126.75, 124.93, 121.79, 119.49 (dd, J=28.0, 5.5 Hz), 117.79, 107.19 (dd, J=34.3, 5.4 Hz), 76.09, 50.62, 35.27, 22.24. $^{19}$F NMR (376 MHz, DMSO-d6) δ −72.95 (ddd, J=10.9, 7.9, 2.5 Hz), −73.77 (t, J=11.0 Hz). LCMS: Purity 97%, MS (m/z) 492/494 (M+H)$^+$.

130

(S)-4-((2,6-Difluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide (I-50)

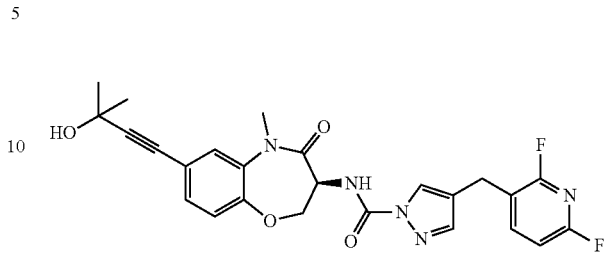

$^1$H NMR (400 MHz, Chloroform-d) δ 7.98 (d, J=7.2 Hz, 1H), 7.92 (s, 1H), 7.63 (dt, J=9.5, 7.8 Hz, 1H), 7.48 (s, 1H), 7.28-7.22 (m, 2H), 7.14-7.07 (m, 1H), 6.75 (dd, J=8.0, 2.9 Hz, 1H), 4.85 (dt, J=11.2, 7.2 Hz, 1H), 4.67 (dd, J=9.8, 7.3 Hz, 1H), 4.30 (dd, J=11.3, 9.8 Hz, 1H), 3.79 (s, 2H), 3.40 (s, 3H), 1.61 (s, 6H). $^{13}$C NMR (101 MHz, Chloroform-d) δ 168.36, 160.80 (dd, J=122.8, 13.8 Hz), 158.35 (dd, J=123.2, 14.0 Hz), 149.83, 148.86, 144.76 (dd, J=7.6, 5.3 Hz), 142.75, 135.97, 132.09 (d, J=10.0 Hz), 130.94, 128.51 (d, J=12.1 Hz), 126.98, 126.51, 123.03, 121.04, 120.54, 118.19 (dd, J=28.4, 6.0 Hz), 106.23 (dd, J=34.4, 5.7 Hz), 94.74, 80.48, 77.09, 65.51, 50.04, 35.50, 31.39, 22.67. $^{19}$F NMR (376 MHz, Chloroform-d) δ −71.01 (t, J=9.7 Hz), −71.98 (t, J=10.5 Hz).). LCMS: Purity 97%, MS (m/z) 496 (M+H)$^+$.

Example 10

In this example, compounds of the disclosure were evaluated using a biochemical assay using the ADP-Glo™ technology.

ADP-Glo™ (Promega, Madison, Wis., USA) reagents were thawed at ambient temperature. Kinase Detection Reagent was prepared by mixing kinase detection buffer with the lyophilized kinase detection substrate.

A 500 ml stock volume of 5× Reaction Kinase Buffer was made by mixing 1000 μl of 1M MgCl$_2$, 500 μl of 1M Tris-HCL pH7.4, 0.5 mg/ml (25 mg) of BSA, and 3475 μl of distilled H$_2$O. A 3 ml 2× working stock volume of Reaction Kinase Buffer was made containing a final concentration of 100 μM DTT and 4 mM MnCl$_2$.

Components of RIPK1 enzyme (Rigel Pharmaceuticals, South San Francisco, Calif., USA) were thawed on ice. Diluted RIPK1 was prepared in 1× Kinase Reaction Buffer (diluted from 2× buffer) to 31 ng/well. A 166 M working stock ATP assay solution was prepared in 1× Kinase Reaction Buffer (diluted from 2× buffer).

Compounds were serially diluted in DMSO from 250 uM in 4-fold dilutions then diluted 1:5 in 2× Reaction Buffer in a 96 well plate. 1.0 ul of diluted compound was added to a 384 well plate in duplicate. 2 μl of diluted Active RIPK1 was added to 384 well plate (do not add to column1) add 2× rxn buffer to column 1. AKT (Anaspec, Fremont, Calif., USA) at 150 nM was combined with ATP working stock at equal volume and 2 ul/well were added to the 384 well plate. The final reaction volume was 5.0 μl.

The plate was quickly centrifuged and the reaction was incubated at 30° C. for 30 minutes. Adding 5 μl of ADP-Glo™ terminated the reaction. The plate was quickly centrifuged and the reaction was incubated at room temperature for 40 minutes. Kinase Detection Reagent was then added and incubated at room temperature for 30 minutes. The relative light unit (RLU) of kinase reaction was determined by luminescent (Luminescence 0.1 s) using a Wallac Victor2 Luminometer (PerkinElmer, Waltham, Mass., USA). $IC_{50}$ values obtained from this example are provided by Table 1.

TABLE 1

| Compound | RIPK1 ADP-Glo Kinase ($IC_{50}$) |
|---|---|
| I-1 | 0.0206 |
| I-2 | 0.0422 |
| I-3 | 0.0289 |
| I-4 | 0.0553 |
| I-5 | 0.0246 |
| I-6 | 0.0409 |
| I-7 | 0.0186 |
| I-8 | 0.0264 |
| I-9 | 0.0643 |
| I-10 | 0.3035 |
| I-11 | 0.1203 |
| I-12 | 0.0252 |
| I-13 | 0.0212 |
| I-14 | 0.0176 |
| I-15 | 0.0194 |
| I-16 | 0.0379 |
| I-17 | 0.111 |
| I-18 | 0.0652 |
| I-19 | 0.1045 |
| I-20 | 0.0217 |
| I-21 | 0.168 |
| I-22 | 0.0083 |
| I-23 | 0.0257 |
| I-24 | 0.0403 |
| I-25 | 0.83 |
| I-26 | 0.0355 |
| I-27 | 0.0193 |
| I-28 | 0.1019 |
| I-29 | 0.0694 |
| I-30 | 0.4798 |
| I-31 | 0.1057 |
| I-32 | 0.0162 |
| I-33 | 0.0171 |
| I-34 | 0.0153 |
| I-35 | 0.0194 |
| I-36 | 0.0118 |
| I-37 | 0.0162 |
| I-38 | 0.0194 |
| I-39 | 0.0283 |
| I-40 | 0.0129 |
| I-41 |  |
| I-42 | 0.0182 |
| I-43 | 0.0177 |
| I-44 | 0.0629 |
| I-45 | 0.045 |
| I-46 | 0.0375 |
| I-47 | 0.0175 |
| I-48 | 0.6455 |
| I-49 | 0.2067 |
| I-50 | 0.1806 |

Example 11

In this example, U937 and L929 cells were exposed to compounds of the present disclosure and a cell necroptosis assay was conducted to evaluate the compounds' activity against human RIP1 and murine RIP1.

U937 and L929 cells were obtained from the American Type Culture Collection (Manassa, Va., USA). Both cells were maintained in logarithmic growth phase in complete RPMI 1640 media (Sigma, ST Louis, Mo., USA) supplemented with 10% fetal bovine serum (Sigma, ST Louis, Mo., USA) at 37° C. with 5% $CO_2$. For necroptosis assay, L929 cells were plated for 18 h in 100 µL/well medium at 10K cells/well in Costar 96-well black clear-bottom plates (Fisher Scientific, Hampton, N.H., USA); U937 cells were plated on the day of the assay in 50 µL/well medium containing 60 uM zVAD-fmk (Lonza, Basel, Switzerland) at 50K cells/well. Medium from L929 cells were removed from the 96-well plates and replaced with 50 µL/well new medium containing 40 uM zVAD-fmk. Each compound of the present disclosure evaluated in this example was serially diluted in DMSO from 2.5 mM in 4-fold dilutions, and then diluted 1:125 in complete medium. 50 µL/well 2× of the compound was then added to the cells in the plates. The cells were pre-incubated with the compound for 1 hour at 37° C. with 5% $CO_2$ and before addition of 10 µL/well 11×TNFa (Peprotech, Rocky Hill, N.J., USA) to give a final concentration of 2 ng/mL for TNFa. The relative amount of necroptosis cells was determined by luminescent using a Wallac Victor2 Luminometer (PerkinElmer, Waltham, Mass., USA) and a CellTiter-Glo® Luminescent Cell Viability Reagent Assay (Promega, Madison, Wis., USA) added per manufacturer instructions after 18 hours of TNFa stimulation at 37° C. with 5% $CO_2$. Results from this example are summarized in Table 2. This example establishes that embodiments of the compounds described herein have unexpectedly potent activity against human RIP1 and murine RIP1, which allows their assessment in in vivo mouse models of disease. These results are useful in determining safe and effective doses for humans.

TABLE 2

| Compound | L929-CTG-recovery, L929, TNFa + zVAD ($IC_{50}$) | U937 Zvad TNF CTG Recovery, U937, TNFa + zVAD ($IC_{50}$) |
|---|---|---|
| I-1 | 2.303 | 0.0114 |
| I-2 | 1.801 | 0.0497 |
| I-3 | 3.847 | 0.1523 |
| I-4 | 7.062 | 0.3612 |
| I-5 | 2.016 | 0.0349 |
| I-6 | 3.425 | 0.0496 |
| I-7 | 0.4492 | 0.0148 |
| I-8 | 0.1072 | 0.009 |
| I-8 | 2.334 | 0.0492 |
| I-9 | 2.693 | 0.1631 |
| I-10 | ND* | 2.831 |
| I-11 | 7.431 | 0.1263 |
| I-12 | 3.471 | 0.0734 |
| I-13 | 1.312 | 0.042 |
| I-14 | 1.174 | 0.0143 |
| I-15 | 1.683 | 0.0275 |
| I-16 | 2.39 | 0.0172 |
| I-17 | ND | 0.7147 |
| I-18 | 5013 | 0.2858 |
| I-19 | ND | 0.2639 |
| I-20 | 5004 | 0.0502 |
| I-21 | 30.42 | 1.37 |
| I-22 | 5004 | 0.0351 |
| I-23 | 5000 | 0.0818 |
| I-24 | ND | 0.0698 |
| I-25 | ND | 4.119 |
| I-26 | 0.4069 | 0.0053 |
| I-27 | 0.6218 | 0.0097 |
| I-28 | 5027 | 0.2353 |
| I-29 | 1.724 | 0.0472 |
| I-30 | ND | 7.21 |
| I-31 | ND | 1.977 |
| I-32 | 0.6825 | 0.0163 |
| I-33 | 1.127 | 0.0116 |
| I-34 | 0.0681 | 0.0013 |
| I-35 | 6.859 | 0.07 |
| I-36 | 0.037 | 0.0013 |
| I-37 | 0.6966 | 0.004 |
| I-38 | 0.0512 | 0.001 |
| I-39 | 0.0385 | 0.0005 |
| I-40 | 0.0694 | 0.0005 |
| I-41 | 0.0131 | 0.0012 |
| I-42 | 28.38 | 0.0586 |
| I-43 | 2.519 | 0.0179 |
| I-44 | 4.115 | 0.018 |

TABLE 2-continued

| Compound | L929-CTG-recovery, L929, TNFa + zVAD (IC$_{50}$) | U937 Zvad TNF CTG Recovery, U937, TNFa + zVAD (IC$_{50}$) |
|---|---|---|
| I-45 | 0.5123 | 0.0052 |
| I-46 | 2.369 | 0.0097 |
| I-47 | 2.895 | 0.0408 |
| I-48 | 1.466 | 0.0249 |
| I-49 | ND | 0.1696 |
| I-50 | 17.65 | 0.0623 |

*ND indicates that no activity was detected or that the inhibition curve showed artifacts. This value does not necessarily indicate an inactive compound, but indicates that the experiment failed to yield data for some reason. By way of example, an insoluble compound or other experimental artifact can result in a "ND" value.

Example 12

In this example, an acute hypothermia mouse model assay was used to evaluate the ability of compounds disclosed herein to inhibit TNF-alpha induced hypothermia.

Female C57BL/6 mice are randomly grouped and weighed on Day −1. On the day of the study (Day 0), mice are administered vehicle or test article by oral gavage. Fifteen minutes after oral administration of test agents, each mouse is administered an intraperitoneal (IP) injection of solution containing recombinant human tumor necrosis factor alpha (TNF-a, 25.0 µg) and zVAD-FMK (200 µg). Body temperature is measured at 0 hours (before IP injections) and every hour via rectal probe temperature measuring device. Three (3) hours after IP injections of TNF-a and zVAD/FMK, mice are euthanized by CO$_2$ asphyxiation and blood is collected via cardiac puncture. Serum and plasma are harvested for determination of cytokine and compound levels, respectively. Separate groups of mice (satellite mice) are included for the determination of compound levels in plasma at the time of administration of TNFa/zVAD-FMK.

Certain embodiments of the invention provide for compound, compounds or compositions thereof to traverse the blood-brain barrier. Disclosed compound and composition embodiments exhibit sufficient brain penetration as potential therapeutics in neurological diseases. Brain penetration may be assessed by evaluating free brain/plasma ratio (Bu/Pu) as measured in vivo pharmacokinetic studies in rodents. Other methods for assessing brain penetration are known to persons of ordinary skill in the art. See, for example, Liu, X. et al., J. Pharmacol. Exp. Therap., 325:349-56, 2008.

Example 13

2-((Trimethylsilyl)ethynyl)spiro[3.3]heptan-2-ol

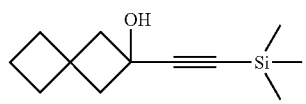

A two neck flask containing a stir bar was heated, cooled to room temperature under vacuum and back filled with argon by balloon. Trimethylsilylacetylene (1.4 mL, 1.0 g, 10.2 mmol) followed by dry THF were transferred to flask and cooled to −78° C. n-BuLi (1.6 M solution in hexanes, 7.0 mL, 11.2 mmol) was added dropwise for a period of 15 min to the above stirring solution. After 30 min, reaction solution was added spiro[3.3]heptanone (1.0 mL, 1.0 g, 9.09 mmol) for 15 min, stirred for 1 h at the same temperature and at ° C. for 1 h. Reaction solution was quenched with ice cold aq. NH$_4$Cl (5 mL) slowly, concentrated to remove volatiles diluted with Et$_2$O (30 mL) and H$_2$O (10 mL). Upon separating organic layer, aqueous layer was extracted with additional Et$_2$O (2×20 mL). Combined organic layers were washed with brine (15 mL), stirred over anhydrous Na$_2$SO$_4$, polish filtered and concentrated. Upon drying the crude concentrate under high vacuum provided 2-((trimethylsilyl)ethynyl)spiro[3.3]heptan-2-ol (1.71 g, 81%) as a white solid which was used in the next step with no further purification. $^1$H NMR (400 MHz, Chloroform-d) δ 2.54-2.43 (m, 2H), 2.26-2.19 (m, 2H), 2.12 (s, 1H), 2.12-2.07 (m, 2H), 2.04-1.93 (m, 2H), 1.88-1.75 (m, 2H), 0.15 (s, 9H). (PMA, KMnO$_4$ and ammonium molybdate stains were used to know progress of reaction)

2-Ethynylspiro[3.3]heptan-2-ol

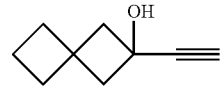

Stirring solution of 2-((trimethylsilyl)ethynyl)spiro[3.3]heptan-2-ol (1.71 g, 8.2 mmol) in dry Et$_2$O (30 mL) at 0° C. under nitrogen was added solid n-Bu$_4$NF.3H$_2$O all at once. After 2 h, clear pale brown reaction solution was quenched with saturated aqueous aq. NH$_4$Cl (10 mL) slowly over a period of 10 min, warmed to room temperature, diluted with H$_2$O (6 mL) and Et$_2$O (20 mL). Upon separating the organic layer, aqueous layer was extracted with additional Et$_2$O (3×20 mL). Upon washing combined organic layers with water (10 mL), aqueous NaHCO$_3$ (10 mL) and brine successively, organic layer was separated, stirred over anhydrous Na$_2$SO$_4$, polish filtered, concentrated and obtained ethynylspiro[3.3]heptan-2-ol (1.11 g, 99%) as a faint brown liquid. The title compound thus obtained was used in the next step with no further purification. $^1$H NMR (400 MHz, Chloroform-d) δ 2.58-2.46 (m, 3H), 2.43 (br s, 1H), 2.30-2.21 (m, 2H), 2.16-2.06 (m, 2H), 2.09-1.95 (m, 2H), 1.89-1.76 (m, 2H). (PMA, KMnO$_4$ and ammonium molybdate stains were used to know progress of reaction)

6-((Trimethylsilyl)ethynyl)-2-oxaspiro[3.3]heptan-6-ol

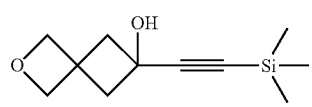

Analogous to the preparation of 2-((trimethylsilyl)ethynyl)spiro[3.3]heptan-2-ol, 6-((trimethylsilyl)ethynyl)-2-oxaspiro[3.3]heptan-6-ol was obtained by the reaction of trimethylsilyl lithium acetylide with 2-oxaspiro[3.3]heptan-6-one as a crude pale brown solid and used in the next step with no further purification. $^1$H NMR (400 MHz, Chloroform-d) δ 4.75-4.62 (m, 4H)), 2.77-2.60 (m, 2H), 2.47-2.36 (m, 2H), 2.23 (s, 1H), 0.14 (s, 9H).

6-Ethynyl-2-oxaspiro[3.3]heptan-6-ol

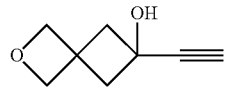

6-Ethynyl-2-oxaspiro[3.3]heptan-6-ol was prepared in the similar manner to the preparation of 2-ethynylspiro[3.3]heptan-2-ol and obtained as a pale brown solid and used in the next step with further purification. ¹H NMR (400 MHz, Chloroform-d) δ 4.74 (s, 2H), 4.66 (s, 2H), 2.76-2.67 (m, 2H), 2.50 (s, 1H), 2.48-2.39 (m, 2H), 2.24 (s, 1H).

1-Methyl-4-(2-methylbut-3-yn-2-yl)piperazine

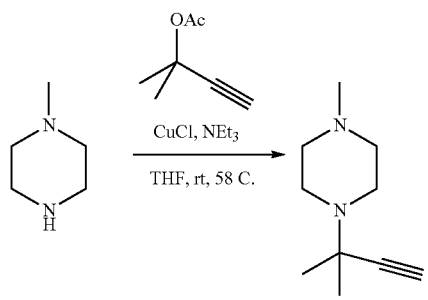

1-Methyl-4-(2-methylbut-3-yn-2-yl)piperazine was prepared by modified procedure of Imada, Y.; Yurasa, M.; Nakamura, I.; Murahashi, S.-i. *J. Org. Chem.* 1998, 63, 2342-2347. To a stirring pale green solution of CuCl (0.10 g, 10 mmol) in dry THF under argon at room temperature, 1-methylpiperazine (1.10 g, 1.22 mL, 11 mmol) NEt₃ (1.11 g, 1.53 mL 11 mmol) were added successively over a period of 20 min. After stirring the blue heterogeneous mixture for 10 min, 2-methylbut-3-yn-2-yl acetate (1.27 g, 10 mmol) (Lepronier, A.; Achard, T.; Giordano, L.; Tenaglia, A.; Buono, G.; Clavier, H. *Adv. Synth. Catal.* 2016. 358 (4), 631-642. Bartoli, G.; Bosco, M.; Dalpozzo, R.; Marcantoni, E.; Massaccesi, M.; Rinaldi, S.; Sambri, L. *Synlett* 2003, 39-42.) in dry THF (5 mL) was added slowly over a period of 20 min and observed a mild exotherm. Reaction mixture was continued to stir for 30 min, heated at 58° C. for 7 h and cooled. Brownish red reaction mixture was diluted with Et₂O (70 mL) and aqueous NaHCO₃ (40 mL). Upon separating organic layer, red colored heterogeneous aqueous layer was extracted with Et₂O (3×75 mL). Combined pale green organic layers were washed with aqueous NaHCO₃ (40 mL) followed by aqueous NaCl successively, stirred over anhydrous Na₂SO₄ and filtered through Celite®. Filtrate was concentrated and obtained the title compound as a crude yellow solid (1.16 g). Further purification by silica gel chromatography (Combiflash® Teledyne RediSep® 12G gold column. A: CH₂Cl₂ B B: 20% MeOH/CH₂Cl₂ @15% B/A. Detection λ 220 and 230 nm) provided an off-white solid (0.54 g, yield 33%). ¹H NMR (400 MHz, Chloroform-d) δ 2.67 (br s, 4H), 2.46 (br s, 4H), 2.26 (app s, 4H), 1.37 (s, 6H). ¹³C NMR (101 MHz, Chloroform-d) δ 85.55, 71.50, 55.45, 53.82, 46.64, 45.88, 27.71.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound wherein the compound is:
I-1:    (S)-4-((6-fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide;
I-2:    (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)-1H-pyrazole-1-carboxamide;
I-3:    (S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-3-yl)oxy)picolinamide;
I-4:    (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)oxy)picolinamide;
I-5:    (S)-4-((6-fluoropyridin-3-yl)oxy)-N-(7-((3-hydroxyoxetan-3-yl)ethynyl)-5-methyl-4-oxo-2,3,4,5-tetrahydrobenzo[b][1,4]oxazepin-3-yl)picolinamide;
I-6:    (S)-4-((6-fluoropyridin-3-yl)oxy)-N-(7-(3-hydroxy-3-methylbut-1-yn-1-yl)-5-methyl-4-oxo-2,3,4,5-tetrahydrobenzo[b][1,4]oxazepin-3-yl)picolinamide;
I-7:    (S)-4-((6-fluoropyridin-2-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide;
I-8:    (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-2-ylmethyl)-1H-pyrazole-1-carboxamide;
I-9:    (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide;
I-10:   (S)—N-(7-((3-hydroxyoxetan-3-yl)ethynyl)-5-methyl-4-oxo-2,3,4,5-tetrahydrobenzo[b][1,4]oxazepin-3-yl)-4-((6-hydroxypyridin-2-yl)methyl)picolinamide;
I-11:   (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-2-yl)methyl)picolinamide;
I-12:   (S)—N-(7-((3-hydroxyoxetan-3-yl)ethynyl)-5-methyl-4-oxo-2,3,4,5-tetrahydrobenzo[b][1,4]oxazepin-3-yl)-4-((6-methylpyridin-2-yl)methyl)picolinamide;
I-13:   (S)-4-((6-fluoropyridin-2-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide;
I-14:   (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-3-ylmethyl)-1H-pyrazole-1-carboxamide;
I-15:   (S)—N-(7-(3-hydroxy-3-methylbut-1-yn-1-yl)-5-methyl-4-oxo-2,3,4,5-tetrahydrobenzo[b][1,4]oxazepin-3-yl)-4-((6-methylpyridin-3-yl)methyl)-1H-pyrazole-1-carboxamide;
I-16:   (S)-4-((6-fluoropyridin-3-yl)methyl)-N-(7-(3-hydroxy-3-methylbut-1-yn-1-yl)-5-methyl-4-oxo-2,3,4,5-tetrahydrobenzo [b][1,4]oxazepin-3-yl)-1H-pyrazole-1-carboxamide;

I-17: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridazin-3-ylmethyl)-1H-pyrazole-1-carboxamide;

I-18: (S)—N-(7-bromo-5-methyl-4-oxo-2,3,4,5-tetrahydrobenzo[b][1,4]oxazepin-3-yl)-4-(pyridin-2-ylmethyl)-1H-pyrazole-1-carboxamide;

I-19: (S)—N-(7-bromo-5-methyl-4-oxo-2,3,4,5-tetrahydrobenzo[b][1,4]oxazepin-3-yl)-4-((6-methylpyridin-2-yl)methyl)-1H-pyrazole-1-carboxamide;

I-20: (S)—N-(7-bromo-5-methyl-4-oxo-2,3,4,5-tetrahydrobenzo[b][1,4]oxazepin-3-yl)-4-((6-fluoropyridin-2-yl)methyl)-1H-pyrazole-1-carboxamide;

I-21: (S)—N-(7-bromo-5-methyl-4-oxo-2,3,4,5-tetrahydrobenzo[b][1,4]oxazepin-3-yl)-4-((6-(trifluoromethyl)pyridin-2-yl)methyl)-1H-pyrazole-1-carboxamide;

I-22: (S)—N-(7-bromo-5-methyl-4-oxo-2,3,4,5-tetrahydrobenzo[b][1,4]oxazepin-3-yl)-4-(pyridin-3-ylmethyl)-1H-pyrazole-1-carboxamide;

I-23: (S)—N-(7-bromo-5-methyl-4-oxo-2,3,4,5-tetrahydrobenzo[b][1,4]oxazepin-3-yl)-4-((6-methylpyridin-3-yl)methyl)-1H-pyrazole-1-carboxamide;

I-24: (S)—N-(7-bromo-5-methyl-4-oxo-2,3,4,5-tetrahydrobenzo[b][1,4]oxazepin-3-yl)-4-((6-fluoropyridin-3-yl)methyl)-1H-pyrazole-1-carboxamide;

I-25: (S)—N-(7-bromo-5-methyl-4-oxo-2,3,4,5-tetrahydrobenzo[b][1,4]oxazepin-3-yl)-4-(pyridazin-3-ylmethyl)-1H-pyrazole-1-carboxamide;

I-26: (S)-4-((2-fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)picolinamide;

I-27: (S)-4-((2-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)picolinamide;

I-28: (S)—N-(7-bromo-5-methyl-4-oxo-2,3,4,5-tetrahydrobenzo[b][1,4]oxazepin-3-yl)-4-(pyridin-4-ylmethyl)-1H-pyrazole-1-carboxamide;

I-29: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyridin-4-ylmethyl)-1H-pyrazole-1-carboxamide;

I-30: (S)—N-(7-bromo-5-methyl-4-oxo-2,3,4,5-tetrahydrobenzo[b][1,4]oxazepin-3-yl)-4-(pyrimidin-2-ylmethyl)-1H-pyrazole-1-carboxamide;

I-31: (S)—N-(7-(3-hydroxy-3-methylbut-1-yn-1-yl)-5-methyl-4-oxo-2,3,4,5-tetrahydrobenzo[b][1,4]oxazepin-3-yl)-4-(pyrimidin-2-ylmethyl)-1H-pyrazole-1-carboxamide;

I-32: (S)-4-((6-fluoropyridin-2-yl)methyl)-N-(7-(3-hydroxyoxetan-3-yl)ethynyl)-5-methyl-4-oxo-2,3,4,5-tetrahydrobenzo[b][1,4]oxazepin-3-yl)-1H-pyrazole-1-carboxamide;

I-33: (S)-4-((6-fluoropyridin-2-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide;

I-34: (S)-4-((6-fluoropyridin-2-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide;

I-35: (S)—N-(8-bromo-1-methyl-2-oxo-2,3,4,5-tetrahydro-1H-benzo[b]azepin-3-yl)-4-((6-fluoropyridin-2-yl)methyl)-1H-pyrazole-1-carboxamide;

I-36: (S)-4-((6-fluoropyridin-2-yl)methyl)-N-(8-((3-hydroxyoxetan-3-yl)ethynyl)-1-methyl-2-oxo-2,3,4,5-tetrahydro-1H-benzo[b]azepin-3-yl)-1H-pyrazole-1-carboxamide;

I-37: (S)-4-((6-fluoropyridin-2-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide;

I-38: (S)-4-((6-fluoropyridin-2-yl)methyl)-N-(8-(3-hydroxy-3-methylbut-1-yn-1-yl)-1-methyl-2-oxo-2,3,4,5-tetrahydro-1H-benzo[b]azepin-3-yl)-1H-pyrazole-1-carboxamide;

I-39: (S)-4-((6-fluoropyridin-2-yl)methyl)-N-(8-(4-hydroxy-3,3-dimethylbut-1-yn-1-yl)-1-methyl-2-oxo-2,3,4,5-tetrahydro-1H-benzo[b]azepin-3-yl)-1H-pyrazole-1-carboxamide;

I-40: (S)-4-((6-fluoropyridin-2-yl)methyl)-N-(8-((4-hydroxytetrahydro-2H-pyran-4-yl)ethynyl)-1-methyl-2-oxo-2,3,4,5-tetrahydro-1H-benzo[b]azepin-3-yl)-1H-pyrazole-1-carboxamide;

I-41: (S)-4-((6-fluoropyridin-2-yl)methyl)-N-(8-((1-hydroxycyclobutyl)ethynyl)-1-methyl-2-oxo-2,3,4,5-tetrahydro-1H-benzo[b]azepin-3-yl)-1H-pyrazole-1-carboxamide;

I-42: (S)—N-(7-bromo-5-methyl-4-oxo-2,3,4,5-tetrahydrobenzo[b][1,4]oxazepin-3-yl)-4-((2-fluoropyridin-3-yl)methyl)-1H-pyrazole-1-carboxamide;

I-43: (S)-4-((2-fluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide;

I-44: (S)-4-((2-fluoropyridin-3-yl)methyl)-N-(7-((4-hydroxytetrahydro-2H-pyran-4-yl)ethynyl)-5-methyl-4-oxo-2,3,4,5-tetrahydrobenzo[b][1,4]oxazepin-3-yl)-1H-pyrazole-1-carboxamide;

I-45: (S)-4-((2-fluoropyridin-3-yl)methyl)-N-(5-methyl-4-oxo-7-((tetrahydro-2H-pyran-4-yl)ethynyl)-2,3,4,5-tetrahydrobenzo[b][1,4]oxazepin-3-yl)-1H-pyrazole-1-carboxamide;

I-46: (S)-4-((2-fluoropyridin-3-yl)methyl)-N-(7-(4-hydroxy-3,3-dimethylbut-1-yn-1-yl)-5-methyl-4-oxo-2,3,4,5-tetrahydrobenzo[b][1,4]oxazepin-3-yl)-1H-pyrazole-1-carboxamide;

I-47: (S)-4-((2-fluoropyridin-3-yl)methyl)-N-(7-((3-hydroxyoxetan-3-yl)ethynyl)-5-methyl-4-oxo-2,3,4,5-tetrahydrobenzo[b][1,4]oxazepin-3-yl)-1H-pyrazole-1-carboxamide;

I-48: (S)-4-((2-fluoropyridin-3-yl)methyl)-N-(7-((1-hydroxycyclobutyl)ethynyl)-5-methyl-4-oxo-2,3,4,5-tetrahydrobenzo[b][1,4]oxazepin-3-yl)-1H-pyrazole-1-carboxamide;

I-49: (S)—N-(7-bromo-5-methyl-4-oxo-2,3,4,5-tetrahydrobenzo[b][1,4]oxazepin-3-yl)-4-((2,6-difluoropyridin-3-yl)methyl)-1H-pyrazole-1-carboxamide; or I-50: (S)-4-((2,6-difluoropyridin-3-yl)methyl)-N-(7-(3-hydroxy-3-methylbut-1-yn-1-yl)-5-methyl-4-oxo-2,3,4,5-tetrahydrobenzo[b][1,4]oxazepin-3-yl)-1H-pyrazole-1-carboxamide.

2. A pharmaceutical composition, comprising a compound according to claim 1 and a pharmaceutically acceptable excipient.

3. The composition according to claim 2 further comprising a therapeutic agent.

* * * * *

UNITED STATES PATENT AND TRADEMARK OFFICE
CERTIFICATE OF CORRECTION

PATENT NO. : 11,479,543 B2
APPLICATION NO. : 17/013034
DATED : October 25, 2022
INVENTOR(S) : Simon Shaw, Somasekhar Bhamidipati and Vanessa Taylor It is certified that error appears in the above-identified patent and that said Letters Patent is hereby corrected as shown below:

In the Claims

Column 136, Line 66, Claim 1, delete "tetrahydrobenzo [b]" and insert -- tetrahydrobenzo[b] --.

Column 137, Lines 36-37, Claim 1, delete "tetrahydrobenzo [b]" and insert -- tetrahydrobenzo[b] --.

Column 137, Lines 43-44, Claim 1, delete "tetrahydrobenzo [b]" and insert -- tetrahydrobenzo[b] --.

Column 137, Line 50, Claim 1, delete "-(3-" and insert -- -((3- --.

Column 138, Line 59, Claim 2, delete "according" and insert -- according to --.

Signed and Sealed this
Twenty-first Day of February, 2023

Katherine Kelly Vidal
Director of the United States Patent and Trademark Office